US 8,741,309 B2

(12) United States Patent
Mengeling et al.

(10) Patent No.: US 8,741,309 B2
(45) Date of Patent: *Jun. 3, 2014

(54) PORCINE REPRODUCTIVE AND RESPIRATORY SYNDROME VACCINE BASED ON ISOLATE JA-142

(75) Inventors: William L. Mengeling, Ames, IA (US); Ann Vorwald, Ames, IA (US); Kelly Lager, Neveda, IA (US); Mike Roof, Ames, IA (US); Kelly Burkhart, Radcliffe, IA (US); David E. Gorcyca, St. Joseph, MO (US)

(73) Assignees: The United States of America as represented by the Secretary of Agriculture, Washington, DC (US); Boehringer Ingelheim Vetmedica, Inc., St. Joseph, MO (US)

( * ) Notice: Subject to any disclaimer, the term of this patent is extended or adjusted under 35 U.S.C. 154(b) by 215 days.

This patent is subject to a terminal disclaimer.

(21) Appl. No.: 11/459,542

(22) Filed: Jul. 24, 2006

(65) Prior Publication Data
US 2007/0042000 A1 Feb. 22, 2007

Related U.S. Application Data

(60) Division of application No. 10/654,545, filed on Sep. 3, 2003, now Pat. No. 7,081,342, which is a continuation of application No. 09/981,282, filed on Oct. 18, 2001, now Pat. No. 6,641,819, which is a continuation-in-part of application No. 09/461,879, filed on Dec. 15, 1999, now abandoned, which is a continuation-in-part of application No. 09/298,110, filed on Apr. 22, 1999, now abandoned.

(51) Int. Cl.
*A61K 39/12* (2006.01)
*C07H 21/04* (2006.01)
*C12N 7/00* (2006.01)
*C12N 15/86* (2006.01)

(52) U.S. Cl.
USPC ............... 424/204.1; 435/456; 435/235.1; 536/23.72

(58) Field of Classification Search
USPC .......................... 435/235.1, 236, 237
See application file for complete search history.

(56) References Cited

U.S. PATENT DOCUMENTS

| | | |
|---|---|---|
| 3,080,291 A | 3/1963 | Sinha et al. |
| 3,137,631 A | 6/1964 | Soloway |
| 3,959,457 A | 5/1976 | Speaker et al. |
| 4,015,100 A | 3/1977 | Gnanamuthu et al. |
| 4,122,167 A | 10/1978 | Buynak et al. |
| 4,205,060 A | 5/1980 | Monsimer et al. |
| 4,224,412 A | 9/1980 | Dorofeev et al. |
| 4,452,747 A | 6/1984 | Gersonde et al. |
| 4,468,346 A | 8/1984 | Paul et al. |
| 4,554,159 A | 11/1985 | Roizman et al. |
| 4,606,940 A | 8/1986 | Frank et al. |
| 4,636,485 A | 1/1987 | van der Smissen |
| 4,744,933 A | 5/1988 | Rha et al. |
| 4,753,884 A | 6/1988 | Kit et al. |
| 4,810,493 A | 3/1989 | Patrick et al. |
| 4,921,706 A | 5/1990 | Roberts et al. |
| 4,927,637 A | 5/1990 | Morano et al. |
| 4,944,948 A | 7/1990 | Uster et al. |
| 5,008,050 A | 4/1991 | Cullis et al. |
| 5,009,956 A | 4/1991 | Baumann |
| 5,132,117 A | 7/1992 | Speaker et al. |
| 5,206,163 A | 4/1993 | Renard et al. |
| 5,213,759 A | 5/1993 | Castberg et al. |
| 5,419,907 A | 5/1995 | Paul et al. |
| 5,476,778 A | 12/1995 | Chladek et al. |
| 5,510,258 A | 4/1996 | Sanderson et al. |
| 5,587,164 A | 12/1996 | Sanderson et al. |
| 5,597,721 A | 1/1997 | Brun et al. |
| 5,620,691 A | 4/1997 | Wensvoort et al. |
| 5,674,500 A | 10/1997 | Peeters et al. |
| 5,677,429 A | 10/1997 | Benfield |
| 5,683,865 A | 11/1997 | Collins et al. |
| 5,690,940 A | 11/1997 | Joo |

(Continued)

FOREIGN PATENT DOCUMENTS

| | | |
|---|---|---|
| CA | 2103460 A1 | 12/1992 |
| DE | 145705 A1 | 1/1981 |

(Continued)

OTHER PUBLICATIONS

Mardassim H., Samir Mounir, and S. Dea, Structural gene analysis of a Quebec reference strain of porcine reproductive and respiratory syndrome virus (PRRSV), Springer US, 1995.*

(Continued)

*Primary Examiner* — Shanon A Foley
(74) *Attorney, Agent, or Firm* — Michael P. Morris; Joyce L. Morrison

(57) ABSTRACT

Substantially avirulent forms of atypical porcine reproductive and respiratory syndrome (PRRS) virus and corresponding vaccines are provided which result from cell culture passaging of virulent forms of PRRS. The resultant avirulent atypical PRRS virus is useful as a vaccine in that PRRS specific antibody response is elicited by inoculation of host animals, thereby conferring effective immunity against both previously known strains of PRRS virus and newly isolated atypical PRRS virus strains. The preferred passaging technique ensures that the virus remains in a logarithmic growth phase substantially throughout the process, which minimizes the time required to achieve attenuation. The present invention also provides diagnostic testing methods which can differentiate between animals infected with field strains and attenuated strains of PRRSV.

10 Claims, 2 Drawing Sheets

(56) References Cited

U.S. PATENT DOCUMENTS

| | | | |
|---|---|---|---|
| 5,695,766 A | 12/1997 | Paul et al. | |
| 5,698,203 A | 12/1997 | Visser et al. | |
| 5,789,388 A | 8/1998 | Visser et al. | |
| 5,840,563 A | 11/1998 | Chladek et al. | |
| 5,846,805 A * | 12/1998 | Collins et al. | 435/235.1 |
| 5,858,729 A | 1/1999 | Van Woensel et al. | |
| 5,866,401 A | 2/1999 | Hesse | |
| 5,888,513 A | 3/1999 | Plana Duran et al. | |
| 5,910,310 A | 6/1999 | Heinen et al. | |
| 5,925,359 A | 7/1999 | Van Woensel et al. | |
| 5,968,525 A | 10/1999 | Fitzgerald et al. | |
| 5,976,537 A * | 11/1999 | Mengeling et al. | 424/184.1 |
| 5,989,563 A | 11/1999 | Chladek et al. | |
| 5,998,601 A | 12/1999 | Murtaugh et al. | |
| 6,001,370 A | 12/1999 | Burch et al. | |
| 6,015,663 A | 1/2000 | Wesley et al. | |
| 6,042,830 A | 3/2000 | Chladek et al. | |
| 6,080,570 A | 6/2000 | Chladek et al. | |
| 6,110,467 A | 8/2000 | Paul et al. | |
| 6,110,468 A | 8/2000 | Collins et al. | |
| 6,197,310 B1 | 3/2001 | Wensvoort et al. | |
| 6,241,990 B1 | 6/2001 | Collins et al. | |
| 6,251,397 B1 | 6/2001 | Paul et al. | |
| 6,251,404 B1 | 6/2001 | Paul et al. | |
| 6,268,199 B1 | 7/2001 | Meulenberg et al. | |
| 6,380,376 B1 | 4/2002 | Paul et al. | |
| 6,391,314 B1 | 5/2002 | Allan et al. | |
| 6,455,245 B1 | 9/2002 | Wensvoort et al. | |
| 6,495,138 B1 | 12/2002 | van Nieuwstadt et al. | |
| 6,498,008 B2 | 12/2002 | Collins et al. | |
| 6,500,662 B1 * | 12/2002 | Calvert et al. | 435/235.1 |
| 6,592,873 B1 | 7/2003 | Paul et al. | |
| 6,641,819 B2 * | 11/2003 | Mengeling et al. | 424/204.1 |
| 6,660,513 B2 | 12/2003 | Mengeling et al. | |
| 6,773,908 B1 | 8/2004 | Paul et al. | |
| 6,806,086 B2 | 10/2004 | Wensvoort et al. | |
| 6,841,364 B2 | 1/2005 | Yuan et al. | |
| 6,855,315 B2 | 2/2005 | Collins et al. | |
| 6,982,160 B2 * | 1/2006 | Collins et al. | 435/235.1 |
| 7,018,638 B2 | 3/2006 | Chu et al. | |
| 7,081,342 B2 | 7/2006 | Mengeling et al. | |
| 7,109,025 B1 | 9/2006 | Eloit et al. | |
| 7,122,347 B2 | 10/2006 | Verheije et al. | |
| 7,132,106 B2 * | 11/2006 | Calvert et al. | 424/205.1 |
| 7,169,394 B2 | 1/2007 | Chu et al. | |
| 7,211,379 B2 | 5/2007 | Ellis et al. | |
| 7,232,680 B2 * | 6/2007 | Calvert et al. | 435/235.1 |
| 7,264,804 B2 | 9/2007 | Collins et al. | |
| 7,273,617 B2 | 9/2007 | Yuan et al. | |
| 7,312,030 B2 | 12/2007 | van Rijn et al. | |
| 7,335,361 B2 | 2/2008 | Liao et al. | |
| 7,335,473 B2 | 2/2008 | Wensvoort et al. | |
| 7,368,117 B2 | 5/2008 | Fetzer et al. | |
| 7,618,797 B2 | 11/2009 | Calvert et al. | |
| 7,632,636 B2 | 12/2009 | Roof et al. | |
| 7,691,389 B2 | 4/2010 | Calvert et al. | |
| 7,722,878 B2 | 5/2010 | Vaughn et al. | |
| 7,897,343 B2 | 3/2011 | Wensvoort et al. | |
| 2002/0012670 A1 | 1/2002 | Elbers et al. | |
| 2002/0098573 A1 | 7/2002 | Meulenberg et al. | |
| 2002/0172690 A1 | 11/2002 | Calvert et al. | |
| 2003/0049274 A1 | 3/2003 | Meulenberg et al. | |
| 2003/0118608 A1 | 6/2003 | Wensvoort et al. | |
| 2003/0157689 A1 | 8/2003 | Calvert et al. | |
| 2003/0219732 A1 | 11/2003 | van Rijn et al. | |
| 2004/0009190 A1 | 1/2004 | Elbers et al. | |
| 2004/0132014 A1 | 7/2004 | Wensvoort et al. | |
| 2004/0197872 A1 | 10/2004 | Meulenberg et al. | |
| 2004/0213805 A1 | 10/2004 | Verheije | |
| 2004/0224327 A1 | 11/2004 | Meulenberg et al. | |
| 2004/0253270 A1 | 12/2004 | Meng et al. | |
| 2006/0063151 A1 | 3/2006 | Roof et al. | |
| 2006/0205033 A1 | 9/2006 | Meulenberg et al. | |
| 2006/0240041 A1 | 10/2006 | Meulenberg et al. | |
| 2006/0286123 A1 | 12/2006 | Fetzer et al. | |
| 2007/0003570 A1 | 1/2007 | Murtaugh et al. | |
| 2007/0042000 A1 * | 2/2007 | Mengeling et al. | 424/204.1 |
| 2009/0148474 A1 | 6/2009 | Roof et al. | |
| 2010/0003278 A1 | 1/2010 | Roof et al. | |
| 2010/0028860 A1 | 2/2010 | Roof et al. | |
| 2010/0129398 A1 | 5/2010 | Klinge et al. | |
| 2011/0104201 A1 | 5/2011 | Mengeling et al. | |
| 2011/0117129 A1 | 5/2011 | Roof et al. | |
| 2011/0195088 A1 | 8/2011 | Roof et al. | |
| 2012/0189655 A1 | 7/2012 | Wu et al. | |

FOREIGN PATENT DOCUMENTS

| | | |
|---|---|---|
| EP | 208672 A1 | 1/1987 |
| EP | 0440219 A1 | 8/1991 |
| EP | 0529584 A2 | 3/1993 |
| EP | 587780 A1 | 3/1994 |
| EP | 0595436 A2 | 5/1994 |
| EP | 0610250 A1 | 8/1994 |
| EP | 676467 A2 | 10/1995 |
| EP | 732340 A2 | 9/1996 |
| EP | 0835929 A1 | 4/1998 |
| EP | 0835930 A1 | 4/1998 |
| EP | 0839912 A1 | 5/1998 |
| EP | 1018557 A2 | 7/2000 |
| FR | 2602791 A1 | 2/1988 |
| GB | 2282811 A | 4/1995 |
| GB | 2289279 A | 11/1995 |
| JP | 62/198626 A | 9/1987 |
| WO | 8803410 A1 | 5/1988 |
| WO | 8908701 A1 | 9/1989 |
| WO | 9221375 A1 | 12/1992 |
| WO | 9303760 A1 | 3/1993 |
| WO | 9306211 A1 | 4/1993 |
| WO | 9307898 A1 | 4/1993 |
| WO | 9314196 A1 | 7/1993 |
| WO | 9418311 A1 | 8/1994 |
| WO | 9528227 A1 | 10/1995 |
| WO | 9531550 A1 | 11/1995 |
| WO | 9604010 A1 | 2/1996 |
| WO | 9606619 A1 | 3/1996 |
| WO | 9636356 A1 | 11/1996 |
| WO | 9640932 A1 | 12/1996 |
| WO | 9700696 A1 | 1/1997 |
| WO | 9731651 A1 | 9/1997 |
| WO | 9731652 A1 | 9/1997 |
| WO | 9818933 A1 | 5/1998 |
| WO | 9835023 A1 | 8/1998 |
| WO | 9850426 A1 | 11/1998 |
| WO | 9855625 A1 | 12/1998 |
| WO | 9855626 A2 | 12/1998 |
| WO | 0053787 A1 | 9/2000 |
| WO | 0065032 A1 | 11/2000 |
| WO | 0159077 A1 | 8/2001 |
| WO | 0190363 A1 | 11/2001 |
| WO | 02095040 A1 | 11/2002 |
| WO | 03062407 A1 | 7/2003 |
| WO | 2006002193 A2 | 1/2006 |
| WO | 2006034319 A2 | 3/2006 |
| WO | 2006074986 A2 | 7/2006 |
| WO | 2007064742 A2 | 6/2007 |
| WO | 2008109237 A2 | 9/2008 |
| WO | 2008121958 A1 | 10/2008 |
| WO | 2010025109 A1 | 3/2010 |
| WO | 2011128415 A1 | 10/2011 |

OTHER PUBLICATIONS

Greiner et al., Quantitative Effect of Porcine Reproductive Respiratory Syndrome Virus on Pig Growth and Immune Response (1999); (Iowa State University Digital Repository @ Iowa State Univversity; Swine Research Report, 1998.*
Greiner 1999 Swine Research Report Citation.*
Office Action in CA 2,650,236, dated Feb. 9, 2011.
Wensvoort et al., "Bovine viral diarrhoea virus infections in piglets born to sows vaccinated against swine fever with contaminated vaccine". Research in Veterinary Science, vol. 45, 1988, pp. 143-148.

(56) References Cited

OTHER PUBLICATIONS

Wensvoort et al., "Characterization of Porcine and Some Ruminant Pestiviruses by Cross-neutralization" vol. 20, 1989, pp. 291-306.
Wensvoort et al., "Lelystad virus, the cause of porcine epidemic abortion and respiratory syndrome: a review of mystery swine disease research in Lelystad". Veterinary Microbiology, vol. 33, Nos. 1-4, Nov. 1992, pp. 185-193.
Wensvoort et al., "Mystery Swine Disease in the Netherlands the Isolation of Lelystad Virus". The Veterinary Quarterly, vol. 13, No. 3, 1991, pp. 121-130.
Wensvoort et al., "Production of Monoclonal Antibodies Against Swine Fever Virus and Their Use in Laboratory Diagnosis". Veterinary Microbiology, vol. 12, 1986, pp. 101-108.
Wensvoort et al., "The Porcine Reproductive and Respiratory Syndrome; Characteristics and diagnosis of the causative virus". Veterinary Biotechnology Newsletter, vol. 3, 1993, pp. 113-120.
Wesley et al., "Differentiation of vaccine (strain RespPRRS) and field strains of porcine reproductive and respiratory syndrome virus by restriction enzyme analysis". Proceedings of the American Association on Swine Practitioners, Nashville, TN, USA, 1996, pp. 141-143.
Westenbrink et al., "An enzyme-linked immunosorbent assay for detection of antibodies to porcine parvovirus". Journal of Virological Methods, vol. 23, 1989, pp. 169-178.
Wieczorek-Krohmer et al., "Porcine reproductive and respiratory syndrome virus (PRRSV): Monoclonal antibodies detect common epitopes on two viral proteins of European and U.S. isolates". Veterinary Microbiology, vol. 51, Nos. 3-4, Aug. 1996, pp. 257-266.
Witte, K.H. "The Situation of 'Epidemic Late Abortion of Swine' in the State of Northrhine-Westphalia". Workshop Seminar, Apr. 1991.
Woode, et al., "Porcine Rotavirus Infection". Diseases of Swine, Fifth Edition, Chapter 26, 1958, pp. 310-322.
Woods et al., "Antigenicity of Inactivated Swine Influenza Virus Concentrated by Centrifugation". Research Communications in Chemical Pathology and Pharmacology, vol. 13, No. 1, 1976, pp. 787-795.
Woods et al., "Experimental challenge of pregnant gilts with swine influenza virus after vaccination". Research Communications in Chemical Pathology and Pharmacology, vol. 15, No. 4, Dec. 1976, pp. 787-95.
Woods et al., "Investigation of Four Outbreaks of Acute Respiratory Disease in Swine and Isolation of Swine Influenza Virus". Health Laboratory Science, vol. 5, No. 4, Oct. 198, pp. 218-224.
Wootton et al., "Structure-function of the ORF7 protein of porcine reproductive and respiratory syndrome virus in the viral capsid assembly". Proceedings of the International Symposium on PRRS and Aujeszky's Disease, Ploufragan, France, pp. 37-38.
Yamane et al., "Annual Examination of Influenza Virus Infection Among Pigs in Miyagi Prefecture, Japan: The Appearance of Hsw1N1 Virus". Acta Virologica, vol. 23, 1979, pp. 240-248.
Yang et al., "Comparative sequence analysis of open reading frames 2 to 7 of the modified live vaccine virus and other North American isolates of the porcine reproductive and respiratory syndrome virus". Archives of Virology, vol. 143, 1998, pp. 601-612.
Yoon et al., "A modified serum neutralization test for the detection of antibody to porcine reproductive and respiratory syndrome virus in swine sera". Journal of Veterinary Diagnostic Investigation, vol. 6, No. 3, Jul. 1994, pp. 289-292.
Yoon et al., "Failure to Consider the Antigenic Diversity of Porcine Reproductive and Respiratory Syndrome (PRRS) Virus Isolates May Lead to Misdiagnosis". Journal of Veterinary Diagnostic Investigation, vol. 7, Jul. 1995, pp. 386-387.
Yoon et al., "Isolation of a Cytopathic Virus from Weak Pigs on Farms with a History of Swine Infertility and Respiratory Syndrome". Journal of Veterinary Diagnostic Investigation, vol. 4, Apr. 1992, pp. 139-143.
Yu et al., "Specific Binding of Host Cellular Proteins to Multiple Sites within the 39 End of Mouse Hepatitis Virus Genomic RNA". Journal of Virology, vol. 69, No. 4, Apr. 1995, pp. 2016-2023.
Yuan et al., "Complete genome comparison of porcine reproductive and respiratory syndrome virus parental and attenuated strains". Virus Research, vol. 74, 2001, pp. 99-110.
Yuan et al., "Erratum to 'Complete genome comparison of porcine reproductive and respiratory syndrome virus parental and attenuated strains' [Virus Research 74 (2001) 99-110]". Virus Research, Vol. 79, 2001, p. 187.
Yuan et al., "Molecular characterization of a highly pathogenic strain of PRRSV associated with porcine High Fever syndrome in China". 2007 International Porcine Reproductive and Respiratory Syndrome (PRRS) Symposium, Chicago, Illinois, Nov.-Dec. 2007, Poster 70.
Yuan et al., American Society for Virology, 16th Annual Meeting, Bozeman, Montana, Jul. 19-23, 1997.
Zeijst, et al., "The Genome of Equine Arteritis Virus". Virology, vol. 68, 1975, pp. 418-425.
Zhou et al., "Generation of cytotoxic and humoral immune responses by nonreplicative recombinant Semliki Forest virus". Proceedings of the National Academy of Sciences, vol. 92, Mar. 1995, pp. 3009-3013.
Zimmerman et al., "General overview of PRRSV: A perspective from the United States". Veterinary Microbiology, vol. 55, Nos. 1-4, Apr. 1997, pp. 187-196.
"Diseases of Swine", Sixth Edition, Iowa State University Press, 1986, pp. 244-315.
"Dutch Team Isolates Mystery Pig Disease Agent", Animal Pharm, vol. 230, Jun. 21, 1991, p. 21.
"Dutch Team Isolates Pig Disease Agent". Animal Pharm. vol. 230, Jun. 21, 1991, p. 21.
"For purification of viral RNA from Plasma, Serum, Cell-free body fluids, Cell-Culture supernatants". QIAamp® Viral RNA Mini Kit Handbook, QIAGEN, Jan. 1999, Cat #52906, pp. 1-35.
"Revision of the taxonomy of the Coronavirus, Torovirus, and Arterivirus genera". Archives of Virology, vol. 135, 1994, pp. 227-239.
Abstracts of Papers Presented at the 71st Annual Meeting of the Conference of Research Workers in Animal Disease, No.'s 1-6, Nov. 5-6, 1990, 2 pages.
Albina et al., "Immune responses in pigs infected with porcine reproductive and respiratory syndrome virus (PRRSV)". Veterinary Immunology and Immunopathology, vol. 61, 1998, pp. 49-66.
Allan et al., "Experimental Infection of Colostrum Deprived Piglets with Porcine Circovirus 2 (PCV2) and Porcine Reproductive and Respiratory Syndrome Virus (PRRSV) Potentiates PCV2 Replication". Archives of Virology, vol. 145, 2000, pp. 2421-2429.
Allende et al., "Mutations in the genome of porcine reproductive and respiratory syndrome virus responsible for the attenuated phenotype". Archives of Virology, vol. 145, No. 6, Jun. 2000, pp. 1149-1161.
Allende et al., "North American and European porcine reproductive and respiratory syndrome viruses differ in nonstructural protein coding regions". Journal of General Virology, vol. 80, 1999, pp. 307-315.
Altschul et al., "Basic Local Alignment Search Tool". Journal of Molecular Biology, vol. 215, 1990, pp. 403-410.
Andreyev et al., "Genetic variation and phylogenetic relationships of 22 porcine reproductive and respiratory syndrome virus (PRRSV) field strains based on sequence analysis of open reading frame 5". Archives of Virology, vol. 142, 1997, pp. 993-1001.
Animal Pharm., No. 228, May 24, 1991, p2.
Ashworth et al., "Antibody-dependent cell-mediated cytotoxicity (ADCC) in Aujeszky's disease". Archives of Virology, vol. 59, No. 4, 1979, pp. 307-318.
Axenova, T.A., "Propagation of Rabies Vaccine Virus in Continuous Green Monkey Kidney Cells". Vopr. Virusol., vol. 2, 1985, p. 182.
Backstrom et al., "Respiratory Diseases of Swine". Veterinary Clinics of North America: Large Animal Practice, vol. 4, 1982, pp. 259-276.
Barfoed et al., "DNA vaccination of pigs with open reading frame 1-7 of PRRS virus". Vaccine, vol. 22, 2004, pp. 3628-3641.
Baric et al., "Interactions between Coronavirus Nucleocapsid Protein and Viral RNAs: Implications for Viral Transcription". Journal of Virology, vol. 62, No. 11, Nov. 1988, pp. 4280-4287.
Baric et al., "Subgenomic Negative-Strand RNA Function during Mouse Hepatitis Virus Infection". Journal of Virology, vol. 74, No. 9, May 2000, pp. 4039-4046.

(56) References Cited

OTHER PUBLICATIONS

Bautista et al., "Comparison of Porcine Alveolar Macrophages and CL 2621 for the Detection of Porcine Reproductive and Respiratory Syndrome (PRRS) Virus and Anti-Prrs Antibody". Journal of Veterinary Diagnostic Investigation, vol. 5, No. 2, Apr. 1993, pp. 163-165.
Bautista et al., "Serologic Survey for Lelystad and VR-2332 Strains of Porcine Respiratory and Reproductive Syndrome (PRRS) Virus in US Swine Herds". Journal of Veterinary Diagnostic Investigation, vol. 5, No. 4, Oct. 1992, pp. 612-614.
Beale, Aj, "Vaccines and antiviral drugs". Principles of bacteriology, virology and immunity, vol. 3, Ch. 86, 1984, pp. 147-161.
Beare et al., "Further Studies in Man of Man of HSw1N1 Influenza Viruses". Journal of Medical Virology, vol. 5, 1980, pp. 33-38.
Beghi et al., "Guillain-Barré Syndrome: Clinicoepidemiologic Features and Effect of Influenza Vaccine". Archives of Neurology, vol. 42, No. 11, 1985, pp. 1053-1057.
Benfield et al., "Characterization of swine infertility and respiratory syndrome (SIRS) virus (isolate ATCC VR-2332)". Journal of Veterinary Diagnostic Investigation, vol. 4, 1992, pp. 127-133.
Benfield et al., "Etiologic Agent of Swine Infertility and Respiratory Syndrome in the United States". 72st Annual Meeting of the Conference of Research Workers in Animal Disease, Chicago, II, Nov. 11-12, 1991, p.48, Abstract No. 268.
Benfield et al., "Properties of SIRS Virus Isolate ATCC VR-2332 in the United States and Preliminary Characterization of a Monoclonal Antibody to this Virus". American Association of Swine Practitioners Newsletter, vol. 4, No. 4, Jul./Aug. 1992, pp. 19-20.
Berendt et al., "Evaluation of Commercially Prepared Vaccines for Experimentally Induced Type/A/New Jersey/8/76 Influenza Virus Infections in Mice and Squirrel Monkeys". The Journal of Infection of Infectious Diseases, vol. 136, 1977, pp. S712-S718.
Berendt et al., "Reaction of Squirrel Monkeys to Intratracheal Inoculation with Influenza/A/New Jersey/76 (Swine) Virus". Infection and Immunity, vol. 16, No. 2, May 1977, pp. 476-479.
Bilodeau et al., "Porcine Reproductive and Respiratory Syndrome' in Quebec". The Veterinary Record, Aug. 3, 1991, p. 102.
Blackburn et al., "Use of human influenza vaccine to protect against blue-eared pig disease". Veterinary Record, vol. 129, No. 1, Jul. 1991, p. 19.
Bohl et al., "Isolation and Serotyping of Porcine Rotaviruses and Antigenic Comparison with Other Rotaviruses". Journal of Clinical Microbiology, vol. 19, No. 2, Feb. 1984, pp. 105-111.
Bouillant et al., "Viral Susceptibility of a Cell Line Derived from the Pig Oviduct". Canadian Journal of Comparative Medicine, vol. 39, 1975, pp. 450-456.
Boursnell et al., "Sequence of the membrane protein gene from avian coronavirus IBV". Virus Research, vol. 1, 1984, pp. 303-313.
Boursnell et all., "Completion of the Sequence of the Genome of the Coronavirus Avian Infectious Bronchitis Virus". Journal of General Virology, vol. 68, 1987, pp. 57-77.
Bowie et al., "Deciphering the Message of Protein Sequences: Tolerance to Amino Acid Substitutions". Science, vol. 247, 1990, pp. 1306-1310.
Boyer et al., "Infectious Transcripts and cDNA Clones of RNA Viruses". Virology, vol. 198, No. 2, Feb. 1994, pp. 415-426.
Bramel-Verheije et al., "Expression of a Foreign Epitope by Porcine Reproductive and Respiratory Syndrome Virus". Virology, vol. 278, 2000, pp. 380-389.
Bredenbeek et al., "The primary structure and expression of the second open reading frame of the polymerase gene of the coronavirus MHV-A59; a highly conserved polymerase is expressed by an efficient ribosomal frameshifting mechanism". Nucleic Acids Research, vol. 18, No. 7, 1990, pp. 1825-1832.
Brenner et al., "A Negative Staining Method for High Resolution Electron Microscopy of Viruses". Biochimica Et Biophysica Acta, vol. 34, 1959, pp. 103-110.
Brinton-Darnell et al., "Structure and chemical-physical characteristics of lactate dehydrogenase-elevating virus and its RNA". Journal of Virology, vol. 16, No. 2, Aug. 1975, pp. 420-433.
Brinton-Darnell, M. "Lactate Dehydrogenase-Elevating, Equine Arteritis and Lelystad Viruses". Encyclopedia of Virology, vol. 2, 1999, pp. 763-771.
Bruner et al., "Hagan's Infectious Diseases of Domestic Animals". Cornell University Press, Table XXXII, 1973.
Bruggemann et al., "Immunoglobulin V region variants in hybridoma cells. I. Isolation of a variant with altered idiotypic and antigen binding specificity". The EMBO Journal, vol. 1, No. 5, 1982, pp. 629-634.
Buck, K. W., "Comparison of the Replication of Positive-Stranded RNA Viruses of Plants and Animals". Advances in Virus Research, vol. 47, 1996, pp. 159-251.
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue". The Journal of Cell Biology, vol. 111, 1990, pp. 2129-2138.
Burroughs, et al., "Relationship of San Miguel Sea Lion Virus to Other Members of the Calicivirus Group". Intervirology, vol. 10, 1978, pp. 51-59.
Cabasso et al., "Propagation of Infectious Canine Hepatitis Virus in Tissue Culture". Proceedings of the Society for Experimental Biology and Medicine, vol. 85, 1954, pp. 239-245.
Caeiro et al., "In vitro DNA replication by cytoplasmic extracts from cells infected with African swine fever virus". Virology, vol. 179, No. 1, Nov. 1990, pp. 87-94.
Callebaut et al., "Antigenic Differentiation between Transmissible Gastroenteritis Virus of Swine and a Related Porcine Respiratory Coronavirus". Journal of General Virology, vol. 69, 1988, pp. 1725-1730.
Carrascosa et al., "Relationship of San Miguel Sea Lion Virus to Other Members of the Calicivirus Group". Journal of Virological Methods, vol. 3, No. 6, Jan. 1982, pp. 303-310.
Carvajal et al., "Evaluation of a Blocking ELISA Using Monoclonal Antibodies for the Detection of Porcine Epidemic Diarrhea Virus and Its Antibodies". Journal of Veterinary Diagnostic Investigation, vol. 7, No. 1, Jan. 1995, pp. 60-64.
Cavanagh, D., "Nidovirales: a new order comprising Coronaviridae and Arteriviridae". Archives of Virology, vol. 142, No. 3, 1997, pp. 629-633.
Chang et al., "A cis-Acting Function for the Coronavirus Leader in Defective Interfering RNA Replication". Journal of Virology, vol. 68, No. 12, Dec. 1994, pp. 8223-8231.
Chang et al., "Evolution of Porcine Reproductive and Respiratory Syndrome Virus during Sequential Passages in Pigs". Journal of Virology, vol. 76, No. 10, May 2002, pp. 4750-4763.
Chao et al., "Monoclonal Antibodies to Metacyclic Stage Antigens of Trypanosoma Cruzi" The American Journal of Tropical Medicine and Hygiene, vol. 34, No. 4, Jul. 1985, pp. 694-701.
Charley, B., "Interaction of influenza virus with swine alveolar macrophages: Influence of anti-virus antibodies and cytochalasin B". Annales de l'Instiut Pasteur. Virologie, vol. 134, No. 1, Jan. 1983, pp. 51-59.
Chasey et al., "Replication of Atypical Ovine Rotavirus in Small Intestine and Cell Culture". Journal of General Virology, vol. 67, No. 3, Mar. 1986, pp. 567-576.
Chen et al., "Determination of the 5' end of the lactate dehydrogenase-elevating virus genome by two independent approaches". Journal of General Virology, vol. 75, 1994, pp. 925-930.
Christianson et al., "Experimental Reproduction of a Newly Described Viral Disease, Swine Infertility and Respiratory Syndrome (SIRS), in Pregnant Sows". 72st Annual Meeting of the Conference of Research Workers in Animal Disease, Chicago, IL, Nov. 11 & 12, 1991, p. 48, Abstract No. 269.
Christianson et al., "Experimental reproduction of swine infertility and respiratory syndrome in pregnant sows". American Journal of Veterinary Research, vol. 53, No. 4, Apr. 1992, pp. 485-488.
Christianson et al., "Porcine reproductive and respiratory syndrome: A review"., Journal of Swine Health and Production, vol. 2, No. 2, Mar.-Apr. 1994, pp. 10-28.
Christianson et al., "Swine Infertility and Respiratory Syndrome". Pig Veterinary Journal, vol. 27, No. 9, Apr. 1991.

(56) References Cited

OTHER PUBLICATIONS

Chutivongse et al., "One-year study of the 2-1-1 intramuscular postexposure rabies vaccine regimen in 100 severely exposed Thai patients using rabies immune globulin and Vero cell rabies vaccine". Vaccine, vol. 9, No. 8, Aug. 1991, pp. 573-576.

Clark et al., "Trypsin enhancement of rotavirus infectivity: mechanism of enhancement". Journal of Virology, vol. 39, No. 3, Sep. 1981, pp. 816-822.

Collins et al., "Experimental Transmission of Swine Reproductive Failure Syndrome (Mystery Swine Disease) in Gnotobiotic Piglets". 71st Annual Meeting of the Conference of Research Workers in Animal Disease, Chicago, IL, Nov. 5-6, 1990, Abstract No. 2.

Collins et al., "Isolation of swine infertility and respiratory syndrome virus (isolate ATCC VR-2332) in North America and experimental reproduction of the disease in gnotobiotic pigs". Journal of Veterinary Diagnostic Investigation, vol. 4, 1992, pp. 117-126.

Collins et al., "Production of infectious human respiratory syncytial virus from cloned cDNA confirms an essential role for the transcription elongation factor from the 5' proximal open reading frame of the M2 mRNA in gene expression and provides a capability for vaccine development". Proceedings of the National Academy of Sciences, vol. 92, Dec. 1995, pp. 11563-11567.

Collins et al., "Respiratory Disease in a Swine Herd Experiencing a Reproductive Failure Syndrome". Minnesota Swine Conference for Veterinarians, Sep. 16-18, 1990, p. 254.

Collins et al., "Swine Diagnostic Pathology". Allen D. Leman Swine Conference, 1998, pp. 1-5.

Collins et al., "Swine Infertility and Respiratory Syndrome (Mystery Swine Disease)". Minnesota Swine Conference for Veterinarians, Sep. 16, 1991.

Collins, J.E., "Newly Recognized Respiratory Syndromes in North American Swine Herds". American Association of Swine Practitioners Newsletter, vol. 3, No. 7, Sep.-Oct. 1991.

Conner et al., "Isolation and characteristics of an equine reovirus type 3 and an antibody prevalence survey to reoviruses in horses located in New York State". Veterinary Microbiology, vol. 9, No. 1, Feb. 1984, pp. 15-25.

Conzelmann et al., "Molecular Characterization of Porcine Reproductive and Respiratory Syndrome Virus, a Member of the Arterivirus Group". Virology, vol. 193, 1993, pp. 329-339.

Cooper et al., "Porcine Reproductive and Respiratory Syndrome: NEB-1 PRRSV Infection did not Potentiate Bacterial Pathogens". Journal of Veterinary Diagnostic Investigation, vol. 7, No. 3, Jul. 1995, pp. 313-320.

Corn et al., "Isolation of Vesicular Stomatitis Virus New Jersey Serotype from Phlebotomine Sand Files in Georgia". The American Journal of Tropical Medicine and Hygiene, vol. 42, No. 5, May 1990, pp. 476-482.

Dacso, et al., "Sporadic occurrence of zoonotic swine influenza virus infections". Journal of Clinical Microbiology, vol. 20, No. 4, Oct. 1984, pp. 833-835.

Database WPIL Week 8702, Derwent Publications Ltd., London, GB; AN 87-009295 [2] & EP, A,208672 (Regional Wallonne-Chiron Corp, Wallonne Regional) Jan. 14, 1987.

Database WPIL Week 8741, Derwent Publications Ltd., London, GB; AN 87-286929 [41] & EP, A,62, 198626 (Za Bieseibutsu Kagaku Ken) Sep. 2, 1987.

Database WPIL Week 8821, Derwent Publications Ltd., London, GB; AN 88-147502 [21] & WO,A,8 803 410 (Inst Pasteur) May 19, 1988.

De Mazancourt et al., "Antibody response to the rubella virus structural proteins in infants with the congenital rubella syndrome". Journal of Medical Virology, vol. 19, No. 2, Jun. 1986, pp. 111-122.

De Vries et al., "Genetic Manipulation of Equine Arteritis Virus Using Full-Length cDNA Clones: Separation of Overlapping Genes and Expression of a Foreign Epitope". Virology, vol. 270, No. 1, 2000, pp. 84-97.

De Vries et al., "The Genome Organization of the Nidovirales: Similarities and Differences between Arteri-, Toro-, and Coronaviruses". Seminars in Virology, vol. 8, 1997, pp. 33-47.

De Vries, et al., "All subgenomic mRNAs of equine arteritis virus contain a common leader sequence". Nucleic Acids Research, vol. 18, No. 11, 1990, pp. 3241-3247.

Dea et al., "Antigenic Variability among North American and European Strains of Porcine Reproductive and Respiratory Syndrome Virus as Defined by Monoclonal Antibodies to the Matrix Protein". Journal of Clinical Microbiology, vol. 34, No. 5, Jun. 1996, pp. 1488-1493.

Dea et al., "Antigenic variant of swine influenza virus causing proliferative and necrotizing pneumonia in pigs". Journal of Veterinary Diagnostic Investigation, vol. 4, No, 4, 1992, pp. 380-392.

Dea et al., "Caracteristiques d'Isolats des virus influenza et de l'encephalomyocardite associes au Syndrome Reproducteur et Respiratoire Porcine (S.R.R.P.) au Quebec.sup.a," Le Medecin Veterinaire Du Quebec, vol. 21, No. 4, Nov. 1991, pp. 170-175.

Dea et al., "Current knowledge on the structural proteins of porcine reproductive and respiratory syndrome (PRRS) virus: comparison of the North American and European isolate". Archives of Virology, vol. 145, No. 4, Apr. 2000, pp. 659-688.

Dea et al., "Isolation of encephalomyocarditis virus among stillborn and post-weaning pigs in Quebec". Archives of Virology, vol. 117, Nos. 1-2, 1991, pp. 121-128.

Dea et al., "Swine reproductive and respiratory syndrome in Quebec: Isolation of an enveloped virus serologically-related to Lelystad virus". Canadian Veterinary Journal, vol. 33, No. 12, Dec. 1992, pp. 801-808.

Dea et al., "Virus Isolations from Farms in Quebec Experiencing Severe Outbreaks of Respiratory and Reproductive Problems". Proceedings Mystery Swine Disease Committee Meeting, Oct. 6, 1990, pp. 67-71.

Del Val et al., "Glycosylated components of African swine fever virus particles". Virology, vol. 152, No. 1, Jul. 1986, pp. 39-49.

Den Boon et al., "Equine Arteritis Virus Is Not a Togavirus but Belongs to the Coronaviruslike Superfamily". Journal of Virology, vol. 65, No. 6, 1991, pp. 2910-2920.

Den Boon et al., "Processing and Evolution of the N-Terminal Region of the Arterivirus Replicase ORF1a Protein: Identification of Two Papainlike Cysteine Proteases". Journal of Virology, vol. 69, No. 7, Jul. 1995, pp. 4500-4505.

Deng et al., "An improved procedure for utilizing terminal transferase to add homopolymers to the 3' termini of DNA". Nucleic Acids Research, vol. 9, No. 16, 1981, pp. 4173-4188.

Derbyshire, J.B. "Porcine Enterovirus Infections". Diseases of Swine, Fifth Edition, Chapter 20, 1958, pp. 285-270.

Devereux et al., "A Comprehensive Set of Sequence Analysis Programs for Vax". Nucleic Acids Research, vol. 12, No. 1, 1984, pp. 387-395.

Dianzani et al., "Is Human Immunodeficiency Virus RNA Load Composed of Neutralized Immune Complexes". The Journal of Infectious Diseases, Vol. 185, 2002, pp. 1051-1054.

Dildrop et al., "Immunoglobulin V region variants in hybridoma cells. II. Recombination between V genes". The Embo Journal, Vol. 1, No. 5, 1982, pp. 635-640.

Dreher, T.W., "Functions of the 3'-Untranslated Regions of Positive Strand RNA Viral Genomes". Annual Review of Phytopathology, vol. 37, 1999, pp. 151-174.

Thanawongnuwech et al., "Effects of Low (Modified-live Virus Vaccine) and High (VR-2385)-Virulence Strains of Porcine Reproductive and Respiratory Syndrome Virus on Pulmonary Clearance of Copper Particles in Pigs". Veterinary Pathology, vol. 35, 1998, pp. 398-406.

Theil et al., "Isolation and Serial Propagation of Turkey Rotaviruses in a Fetal Rhesus Monkey Kidney (MA104) Cell Line". Avian Diseases, vol. 30, No. 1, 1985, pp. 93-104.

Theil et al., "Partial characterization of a bovine group a rotavirus with a short genome electropherotype". Journal of Clinical Microbiology, vol. 26, No. 6, Jun. 1988, p. 1094-1099.

Thomson et al., "Ontario. Proliferative and necrotizing pneumonia (PNP) of swine: the Ontario situation". Canadian Veterinary Journal, vol. 32, May 1991, p. 313.

Thouless et al., "Isolation of two lapine rotaviruses: Characterization of their subgroup, serotype and RNA electropherotypes". Archives of Virology, vol. 89, Nos. 1-4, 1986, pp. 161-170.

(56) References Cited

OTHER PUBLICATIONS

Tian et al., "Emergence of Fatal PRRSV Variants: Unparalleled Outbreaks of Atypical PRRS in China and Molecular Dissection of the Unique Hallmark". PLoS One, vol. 2, No. 6, e526, 2007, pp. 1-10.
Timony, P.J. "Equine Viral Arteritis", Manual of Standards for Diagnostic Tests and Vaccines, 1992, pp. 493-500.
Tobita et al., "Plaque Assay and Primary Isolation of influenza a Viruses in an Established Line of Canine Kidney Cells (MDCK) in the Presence of Trypsin". Medical Microbiology and Immunology, vol. 162, No. 1, Dec. 1975, pp. 9-14.
Todd et al., "Development of an adjuvant-active nonionic block copolymer for use in oil-free subunit vaccines formulations". Vaccine, vol. 15, No. 5, 1997, pp. 564-570.
Travassos et al., "Carajas and Maraba Viruses, Two New Vesiculoviruses Isolated from Phlebotomine Sand Flies in Brazil". American Journal of Tropical Medicine and Hygiene, vol. 33, No. 5, Sep. 1984, pp. 999-1006.
Tsunemitsu et al., "Isolation, characterization, and serial propagation of a bovine group C rotavirus in a monkey kidney cell line (MA104)". Journal of Clinical Microbiology, vol. 29, No. 11, Nov. 1991, pp. 2609-2613.
Ulmer et al., "Enhancement of DNA vaccine potency using conventional aluminum adjuvants". Vaccine, vol. 18, 2000, pp. 18-28.
Urasawa et al., "Sequential Passages of Human Rotavirus in MA-104 Cells". Microbiology and Immunology, vol. 25, No. 10, 1981, pp. 1025-1035.
Van Alstine, W.G., "Mystery Swine Disease in the United States". Workshop/Seminar on the New Pig Disease in the European Community, Apr. 29-30, 1991.
Van Alstine, W.G., "Past Diagnostic Approaches and Findings and Potentially Useful Diagnostic Strategies". Proceedings Mystery Swine Disease Committee Meeting, Oct. 6, 1990, pp. 32-58.
Van Berlo et al., "Equine Arteritis Virus-Infected Cells Contain Six Polyadenylated Virus-Specific RNAs". Virology, vol. 118, 1982, pp. 345-352.
Van Der Linden et al., "Virological kinetics and immunological responses to a porcine reproductive and respiratory syndrome virus infection of pigs at different ages". Vaccine, vol. 21, 2003, pp. 1952-1957.
Van Der Meer et al., "ORF1a-Encoded Replicase Subunits Are Involved in the Membrane Association of the Arterivirus Replication Complex". Journal of Virology, vol. 72, No. 8, 1998, pp. 6689-6698.
Van Der Most et al., "A Domain at the 3' End of the Polymerase Gene Is Essential for Encapsidation of Coronavirus Defective Interfering RNAs". Journal of Virology, vol. 65, No. 6, Jun. 1991, pp. 3219-3226.
Van Dinten et al., "An infectious arterivirus cDNA clone: Identification of a replicase point mutation that abolished discontinuous mRNA transcription". Proceedings of the National Academy of Sciences, vol. 94, Feb. 1997, pp. 997-996.
Van Dinten et al., "Processing of the Equine Arteritis Virus Replicase ORF1b Protein: Identification of Cleavage Products Containing the Putative Viral Polymerase and Helicase Domains". Journal of Virology, vol. 70, No. 10, Oct. 1996, pp. 6625-6633.
Van Dinten et al., "Proteolytic Processing of the Open Reading Frame 1b-Encoded Part of Arterivirus Replicase Is Mediated by nsp4 Serine Protease and Is Essential for Virus Replication". Journal of Virology, vol. 73, No. 3, Mar. 1999, pp. 2027-2037.
Van Marle et al., "Arterivirus discontinuous mRNA transcription is guided by base pairing between sense and antisense transcription-regulating sequences". Proceedings of the National Academy of Sciences, vol. 96, 1999, pp. 12056-12061.
Van Marle et al., "Characterization of an Equine Arteritis Virus Replicase Mutant Defective in Subgenomic mRNA Synthesis". Journal of Virology, vol. 73, No. 7, Jul. 1999, pp. 5274-5281.
Van Marle et al., "Regulation of Coronavirus mRNA Transcription". Journal of Virology, vol. 69, No. 12, Dec. 1995, pp. 7851-7856.
Van Nieuwstadt et al., "Infection with porcine respiratory coronavirus does not fully protect pigs against intestinal transmissable gastroenteritis virus". The Veterinary Record, vol. 125, No. 3, 1989, pp. 60-63.

Van Nieuwstadt et al., "Proteins Encoded by Open Reading Frames 3 and 4 of the Genome of Lelystad Virus (Arteriviridae) Are Structural Proteins of the Virion". Journal of Virology, vol. 70, No. 7, Jul. 1996, pp. 4767-4772.
Van Nieuwstadt et al., "Use of two enzyme-linked immunosorbent assays to monitor antibody responses in swine with experimentally induced infection with porcine epidemic diarrhea virus". American Journal of Veterinary Research, vol. 42, Jul. 1991, pp. 1044-1050.
Van Zijl et al., "Live Attenuated Pseudorabies Virus Expressing Envelope Glycoprotein El of Hog Cholera Virus Protects Swine Against Both Pseudorabies and Hog Cholera". Journal of Virology, vol. 65, No. 5, May 1991, pp. 2761-2765.
Vennema et al., "Nucleocapsid-independent assembly of coronavirus-like particles by co-expression of viral envelope protein genes". The Embo Journal, vol. 15, No. 8, 1996, pp. 2020-2028.
Verheije et al., "Kissing Interaction between 3' Noncoding and Coding Sequences Is Essential for Porcine Arterivirus Rna Replication". Journal of Virology, vol. 76, No. 3, Feb. 2002, pp. 1521-1526.
Verheije et al., "Safety and protective efficacy of porcine reproductive and respiratory syndrome recombinant virus vaccines in young pigs". Vaccine, vol. 21, 2003, pp. 2556-2563.
Veterinary Bulletin, vol. 58, No. 11, 1988, Nos. 6903-6909, p. 932.
Veterinary Bulletin, vol. 60, No. 3, 1990, Nos. 1536-1551, pp. 255-256.
Vieira et al., "New pUC-derived cloning vectors with different selectable markers and DNA replication origins". Gene, vol. 100, 1991, pp. 189-194.
VIIIth International Symposium on Nidoviruses (Corona and Arteriviruses), May 20-25, 2000, 32 pages.
Visser, Nicolaas, "Declaration of Dr. N. Visser". Nov. 14, 1995, pp. 1-11.
Von Busse, F.W., Epidemiologic Studies on Porcine Reproductive and Respiratory Syndrome (PRRS). Tierarztliche Umschau, Dec. 1991, pp. 708-717 (Abstract in English p. 711).
Von Ohlinger et al., "Der Seuchenhafte Spatabort beim Schwein Ein Beitrag zur Atiologie des Porcine Reproductive and Respiratory Syndrome (PRRS)". Tierarztl, vol. 46, 1991, pp. 703-708.
Waltner-Toews et al., "A Field Trial to Evaluate the Efficacy of a Combined Rotavirus-Coronavirus/ Escherichia coli vaccine in Dairy Cattle"., Canadian Journal of Comparative Medicine, vol. 49, No. 1, 1985, pp. 1-9.
Wang et al., "Attenuation of porcine reproductive and respiratory syndrome virus strain MN184 using chimeric construction with vaccine sequence". Virology, vol. 371, 2008, pp. 418-429.
Ward et al., "Efficiency of human rotavirus propagation in cell culture". Journal of Clinical Microbiology, vol. 19, No. 6, Jun. 1984, pp. 748-753.
Wardley et al., "The Host Response to African Swine Fever Virus". Progress of Medical Virology, vol. 34, 1987, pp. 180-192.
Wassenaar et al., "Alternative Proteolytic Processing of the Arterivirus Replicase ORF1a Polyprotein: Evidence that NSP2 Acts as a Cofactor for the NSP4 Serine Protease". Journal of Virology, vol. 71, No. 12, Dec. 1997, pp. 9313-9322.
Webster et al., "Chemotherapy and Vaccination: a Possible Strategy for the Control of Highly Virulent Influenza Virus". Journal of Virology, vol. 55, No. 1, 1985, pp. 173-176.
Welch et al., "Construction and evaluation of genetically engineered replication-defective porcine reproductive and respiratory syndrome virus vaccine candidates". Veterinary Immunology and Immunopathology, vol. 102, 2004, pp. 277-290.
Wensvoort et al., "'Blue ear' disease in pigs". Veterinary Record, vol. 128, No. 24, Jun. 1991, p. 574.
Wensvoort et al., "'Lelystad agent'—the cause of abortus blauw (mystery swine disease)". Tijdschr Diergeneeskd, vol. 116, No. 13, Jul. 1991, pp. 675-676.
Wensvoort et al., "An Enzyme Immunoassay Employing Monoclonal Antibodies and Detecting Specifically Antibodies to Classical Swine Fever Virus". Veterinary Microbiology, vol. 17, 1988, pp. 129-140.
Wensvoort et al., "Antigenic Comparison of Lelystad Virus and Swine Infertility and Respiratory Syndrome (SIRS) Virus". Journal of Veterinary Diagnostic Investigation, vol. 4, 1992, pp. 134-138.

(56) References Cited

OTHER PUBLICATIONS

Axenova, T.A. "Propagation of Rabies Vaccine Virus in Continuous Green Monkey Kidney Cells 4647". Vopr. Virusol., vol. 30, No. 2, 1985, p. 182. (English Abstract of Aksenova Reference.).

Matanin et al., "Purification of the major envelop protein GP5 of porcine reproductive and respiratory syndrome virus (PRRSV) from native virions". Journal of Virological Methods, vol. 147, 2008, pp. 127-135.

Pesch et al., "New insights into the genetic diversity of European porcine reproductive and respiratory syndrome virus (PRRSV)". Veterinary Microbiology, vol. 107, 2005, pp. 31-48.

Darwich et al., "Genetic and immunobiological diversities of porcine reproductive and respiratory syndrome genotype I strains". Veterinary Microbiology, vol. 150, 2011, pp. 49-62.

Gao et al., "Genomic characterization of two Chinese isolates of Porcine respiratory and reproductive syndrome virus". Archives of Virology, vol. 149, 2004, pp. 1341-1351.

UniProt: Accession No. C9E449. "SubName: Full=M protein; SubName: Full= Membrane protein". Nov. 3, 2009.

UniProt: Accession No. DOVEE4. "SubName: Full=Unglycosylated membrane protein". Dec. 15, 2009.

UniProt: Accession No. Q6TLB4. "SubName: Full=Membrane protein M". Jul. 5, 2004.

Cano et al., "Impact of a modfied-live porcine reproductive and respiratory syndrome virus vaccine intervention on a population of pigs infected with a heterologous isolate". Vaccine, vol. 25, 2007, pp. 4382-4391.

Wesley et al., "Differentiation of a porcine reproductive and respiratory syndrome virus vaccine strain from North American field strains by restrction fragment length polymorphism analysis of ORF 5". Journal of Veterinary Diagnostic Investigation, vol. 10, 1998, pp. 140-144.

Heath, et al., "The Behaviour of Some Influenza Viruses in Tissue Cultures of Kidney Cells of Various Species". Archiv. f. Virusforschung Bd. VIII, HS, 1985, pp. 577-591.

Hedger et al., "Swine Vesicular Disease Virus". Virus Infections of Porcines, Elsevier Science Publishers, B.V., 1989, pp. 241-250.

Hennen, J., "Statistical methods for longitudinal research on bipolar disorders". Bipolar Disorders, vol. 5, 2003, pp. 156-168.

Hill, Howard, "Overview and History of Mystery Swine". Proceedings of the Mystery Swine Disease Committee Meeting, Denver, CO, Oct. 6, 1990, pp. 29-40.

Hirsch et al., "Ultrastructure of Human Leukocytes After Simultaneous Fixation with Glutaraldehyde and Osmium Tetroxide and "Postfixation" in Uranyl Acetate". The Journal of Cell Biology, vol. 38, 1968, pp. 615-627.

Hofmann et al., "Propagation of the virus of porcine epidemic diarrhea in cell culture". Journal of Clinical Microbiology, vol. 26, No. 11, Nov. 1988, pp. 2235-2239.

Hofmann et al., "Quantitation, biological and physicochemical properties of cell culture-adapted porcine epidemic diarrhea coronavirus (PEDV)". Veterinary Microbiology, vol. 20, No. 2, Jun. 1989, pp. 131-142.

Honda et al., "A Serological Comparison of 4 Japanese Isolates of Porcine Enteroviruses with the International Reference Strains". The Japanese Journal of Veterinary Science, vol. 52, No. 1, 1990, pp. 49-54.

Horowitz et al., "Anti-schistosome monoclonal antibodies of different isotypes—correlation with cytotoxicity". The EMBO Journal, Vol. 2, No. 2, 1983, pp. 193-198.

Horsfall et al., "General Principles of Animal Virus Multiplication". Viral and Rickettsial Infections of Man, Fourth Edition, J.B. Lippincott Company, Philadelphia, 1965, pp. 239-241.

Horzinek et al., "Studies on the Substructure of Togaviruses: II. Analysis of Equine Arteritis Rubella, Bovine Viral Diarrhea, and Hog Cholera Viruses". Archiv Für die gesamte Virusforschung, vol. 33, 1971, pp. 306-318.

Hoshino et al., "Isolation and characterization of an equine rotavirus". Journal of Clinical Microbiology, vol. 18, No. 3, Sep. 1983, pp. 585-591.

Hoshino et al., "Serotypic Similarity and Diversity of Rotaviruses of Mammalian and Avian Origin as Studied by Plaque-Reduction Neutralization". The Journal of Infectious Diseases, vol. 149, No. 5, May 1984, pp. 694-702.

Hsue et al., "Characterization of an Essential RNA Secondary Structure in the 38 Untranslated Region of the Murine Coronavirus Genome". Journal of Virology, Vol. 74, No. 15, Aug. 2000, pp. 6911-6921.

Huang et al., "Polypyrimidine Tract-Binding Protein Binds to the Complementary Strand of the Mouse Hepatitis Virus 39 Untranslated Region, Thereby Altering RNA Conformation". Journal of Virology, vol. 73, No. 11, Nov. 1999, pp. 9110-9116.

Hurrelbrink et al., "Attenuation of Murray Valley Encephalitis Virus by Site-Directed Mutagenesis of the Hinge and Putative Receptor-Binding Regions of the Envelope Protein". Journal of Virology, vol. 75, No. 16, Aug. 2001, pp. 7692-7702.

Hwang et al., "A 68-Nucleotide Sequence within the 39 Noncoding Region of Simian Hemorrhagic Fever Virus Negative-Strand RNA Binds to Four MA104 Cell Proteins". Journal of Virology, vol. 72, No. 5, May 1998, pp. 4341-4351.

Hyllseth, B., "Structural Proteins of Equine Arteritis Virus". Archiv Für die gesamte Virusforschung, vol. 30, 1973, pp. 177-188.

Iltis et al., "Persistent Varicella-Zoster virus infection in a human rhabdomyosarcoma cell line and recovery of a plaque variant". Infection and Immunity, vol. 37, No. 1, Jul. 1982, pp. 350-358.

Imagawa et al., "Isolation of Foal Rotavirus in MA-104 Cells". Bulleting of Equine Research Institute, vol. 18, 1981, pp. 119-128.

International Search Report for PCT/US2000/10852 mailed on Aug. 3, 2000.

IZeta et al., "Replication and Packaging of Transmissible Gastroenteritis Coronavirus-Derived Synthetic Minigenomes". Journal of Virology, vol. 73, No. 2, Feb. 1999, pp. 1535-1545.

Jackwood et al., "Replication of Infectious Bursal Disease Virus in Continuous Cell Lines". Avian Diseases, vol. 31, No. 2, Apr.-Jun. 1987, pp. 370-375.

Johnson et al., "Feline panleucopaenia virus. IV. Methods for obtaining reproducible in vitro results". Research in Veterinary Science, vol. 8, No. 2, Apr. 1967, pp. 256-264.

Johnson et al., "Pathogenic and humoral immune responses to porcine reproductive and respiratory syndrome virus (PRRSV) are related to viral load in acute infection". Veterinary Immunology and Immunopathology, vol. 102, No. 3, PRRS Immunology and Immunopathology Special Issue, Dec. 2004, pp. 233-247.

Johnston et al., "Genetic to genomic vaccination". Vaccine, vol. 15, No. 8, 1997, pp. 808-809.

Joo et al., "Encephalomyocarditis Virus As a Potential Cause for Mystery Swine Disease", Livestock Conservation Institute, Denver, CO, Oct. 6, 1990, pp. 62-66.

Joo et al., "Mystery Swine Disease Meeting". Livestock Conservation Institute, Denver, Colorado, Oct. 6, 1990.

Jun et al., "Comparison of Dynamics in Viremia Levels in Chickens Inoculated with Marek's Disease Virus Strains of Different Pathotypes". Virologica Sinica, vol. 16, No. 1, Mar. 2001, pp. 59-63.

Jusa et al., "Effect of heparin on infection of cells by porcine reproductive and respiratory syndrome virus". American Journal of Veterinary Research, vol. 58, No. 5, May 1997, pp. 488-491.

Just et al., "A/New Jersey/76 influenza vaccine trial in seronegative schoolchildren: Comparison of a subunit vaccine with a whole-virus vaccine". Medical Microbiology and Immunology, vol. 164, No. 4, 1978, pp. 277-284.

Kang et al., "Primary Isolation and Identification of Avian Rotaviruses from Turkeys Exhibiting Signs of Clinical Enteritis in a Continuous MA-104 Cell Line". Avian Diseases, vol. 30, 1986, pp. 494-499.

Kapur et al., "Genetic variation in porcine reproductive and respiratory syndrome virus isolates in the midwestern United States". Journal of General Virology, vol. 77, 1996, pp. 1271-1276.

Kasza et al., "Establishment, viral susceptibility and biological characteristics of a swine kidney cell line SK-6". Research in Veterinary Science, vol. 13, No. 1, Jan. 1972, pp. 46-51.

Kasza et al., "Isolation and Characterization of a Rotavirus from Pits". Veterinary Record, vol. 87, 1970, pp. 681-686.

(56) References Cited

OTHER PUBLICATIONS

Katz et al., "Antigenic differences between European and American isolates of porcine reproductive and respiratory syndrome virus (PRRSV) are encoded by the carboxyterminal portion of viral open reading frame 3". Veterinary Microbiology, vol. 44, No. 1, Apr. 1995, pp. 65-76.
Keffaber, K, "Reproductive Failure of Unknown Etiology"., AASP Newsletter, vol. 1, No. 2, Sep.-Oct. 1989, pp. 1, 4-5, 8-10.
Keffaber, K.K., "Swine Reproductive Failure of Unknown Etiology". The George A. Young Swine Conference & Annual Nebraska SPF Swine Conference, Aug. 13-14, 1990, p. 55.
Key et al., "Genetic variation and phylogenetic analyses of the ORF5 gene of acute porcine reproductive and respiratory syndrome virus isolates". Veterinary Microbiology, vol. 83, 2001, pp. 249-263.
Kim et al., "Analysis of cis-Acting Sequences Essential for Coronavirus Defective Interfering RNA Replication". Virology, vol. 197, No. 1, Nov. 1993, pp. 53-63.
Kim et al., "Different Biological Characteristics of Wild-Type Porcine Reproductive and Respiratory Syndrome Viruses and Vaccine Viruses and Identification of the Corresponding Genetic Determinants". Journal of Clinical Microbiology, vol. 46, No. 5, May 2008, pp. 1758-1768.
Kim et al., "Enhanced replication of porcine reproductive and respiratory syndrome (PRRS) virus in a homogeneous subpopulation of MA-104 cell line". Archives of Virology, vol. 133, 1993, pp. 477-483.
Klein et al., "Deletion of the IgH enhancer does not reduce immunoglobulin heavy chain production of a hybridoma IgD class switch variant". The EMBO Journal, vol. 3, No. 11, Nov. 1984, pp. 2473-2476.
Klinge et al, "Age-dependent resistance to Porcine reproductive and respiratory syndrome virus replication in swine". Virology Journal, vol. 6, No. 177, Oct. 2009.
Klinge et al., "PRRSV replication and subsequent immune responses in swine of various ages". Abstract of Poster No. 56, International Porcine Reproductive and Respiratory Syndrome (PRRS) Symposium, PRRS and PRRSV Related Diseases: Prevention and Control Strategies, Chicago, IL, Nov. 30-Dec. 1, 2007.
Klovins et al., "A Long-range Pseudoknot in Qb RNA is Essential for Replication". Journal of Molecular Biology, vol. 294, 1999, pp. 875-884.
Klump et al., "Complete Nucleotide Sequence of Infectious Coxsackievirus B3 cDNA: Two Initial 5' Uridine Residues Are Regained during Plus-Strand RNA Synthesis". Journal of Virology, vol. 64, No. 4, Apr. 1990, pp. 1573-1583.
Klupp et al., "Sequence and expression of the glycoprotein gH gene of pseudorabies virus". Virology, vol. 182, No. 2, Jun. 1991, pp. 732-741.
Knowles et al., "Classification of porcine enteroviruses by antigenic analysis and cytopathic effects in tissue culture: Description of 3 new serotypes". Archives of Virology, vol. 62, No. 3, 1979, pp. 201-208.
Kolodziej et al., "Epitope tagging and protein surveillance". Methods in Enzymology, vol. 194, 1991, pp. 508-519.
NCBI: Accession No. M96262.2. "Lelystad virus, complete genome." Nov. 8, 2000.
NCBI: Accession No. NC_001639. Lactate dehydrogenase-elevating virus, complete genome. Dec. 8, 2008.
NCBI: Accession No. NC_001961. "Porcine reproductive and respiratory syndrome virus, complete genome." Jan. 12, 2004.
NCBI: Accession No. NC_002533. "Lelystad virus, complete genome." Nov. 11, 2000.
NCBI: Accession No. NC_002534. "Lactate dehydrogenase-elevating virus, complete genome." Dec. 29, 2003.
NCBI: Accession No. U15146. "Lactate dehydrogenase-elevating virus Plagemann strain, complete genome." Jan. 26, 1996.
NCBI: Accession No. U87392 AF030244 U000153. "Porcine reproductive and respiratory syndrome virus strain VR-2332, complete genome." Nov. 17, 2000.
Nelsen et al., "Porcine Reproductive and Respiratory Syndrome Virus Comparison: Divergent Evolution on Two Continents". Journal of Virology, vol. 73, No. 1, Jan. 1999, pp. 270-280.
Nelson et al., "Differentiation of U.S. And European Isolates of Porcine Reproductive and Respiratory Syndrome Virus by Monoclonal Antibodies". Journal of Clinical Microbiology, vol. 31, No. 12, Dec. 1993, pp. 3184-3189.
Nelson et al., "High affinity interaction between nucleocapsid protein and leader/intergenic sequence of mouse hepatitis virus RNA". Journal of General Virology, vol. 81, 2000, pp. 181-188.
Nielsen et al., "Generation of an Infectious Clone of VR-2332, a Highly Virulent North American-Type Isolate of Porcine Reproductive and Respiratory Syndrome Virus". Journal of Virology, vol. 77, No. 6, Mar. 2003, pp. 3702-3711.
Nishimura et al., "Replication and Synthesis of Japanese Encephalitis Virus Ribonucleic Acids in Vero Cells". Japanese Journal of Microbiology, vol. 15, No. 4, 1971, pp. 309-316.
Nodelijk et al., "A quantitative assessment of the effectiveness of PRRSV vaccination in pigs under experimental conditions". Vaccine, vol. 19, 2000, pp. 3636-3644.
Nuttall, P.A., "Growth Characteristics of Two Strains of Bovine Virus Diarrhoea Virus". Archives of Virology, vol. 66, 1980, pp. 365-369.
Oirschot et al., "Development of an ELISA for detection of antibodies to glycoprotein I of Aujeszky's disease virus: a method for the serological differentiation between infected and vaccinated pigs". Journal of Virological Methods, vol. 22, 1988, pp. 191-206.
Ojeh et al., "Isolation, characterisation and serial propagation of a Nigerian strain of porcine group a rotavirus in a monkey kidney cell line (MA104)". Discovery and Innovation, vol. 8, No. 2, Jun. 1996, pp. 159-164.
Oleksiewicz et al., "Epitope Mapping Porcine Reproductive and Respiratory Syndrome Virus by Phage Display: the nsp2 Fragment of the Replicase Polyprotein Contains a Cluster of B-Cell Epitopes". Journal of Virology, vol. 75, No. 7, Apr. 2001, pp. 3277-3290.
Oleksiewicz et al., "Semen from Boars Infected with Porcine Reproductive and Respiratory Syndrome Virus (PRRSV) Contains Antibodies Against Structural as Well as Nonstructural Viral Proteins". Veterinary Microbiology, vol. 81, 2001, pp. 109-125.
Olsthoorn et al., "A conformational switch at the 3' end of a plant virus RNA regulates viral replication". The EMBO Journal, vol. 18, No. 17, 1999, pp. 4856-4864.
Opriessnig et al., "Comparison of Molecular and Biological Characteristics of a Modified Live Porcine Reproductive and Respiratory Syndrome Virus (PRRSV) Vaccine (Ingelvac PRRS MLV), the Parent Strain of the Vaccine (ATCC VR2332), ATCC VR2385, and Two Recent Field Isolates of PRRSV". Journal of Virology, vol. 76, No. 23, Dec. 2002, pp. 11837-11844.
Opriessnig et al., "Use of an Experimental Model to Test the Efficacy of Planned Exposure to Live Porcine Reproductive and Respiratory Syndrome Virus". Clinical and Vaccine Immunology, vol. 14, No. 12, Dec. 2007, pp. 1572-1577.
Ostrowski et al., "Identification of Neutralizing and Nonneutralizing Epitopes in the Porcine Reproductive and Respiratory Syndrome Virus GP5 Ectodomain". Journal of Virology, vol. 76, No. 9, May 2002, pp. 4241-4250.
Pan et al., "Replication of African swine fever virus in cell cultures". American Journal of Veterinary Research, vol. 41, No. 9, Sep. 1980, pp. 1357-1367.
Parratt et al., "Radioimmunoassay of Antibody". 1982, p. 43.
Parsley et al., "Poly (rC) binding protein 2 forms a ternary complex with the 5'-terminal sequences of poliovirus RNA and the viral 3CD proteinase". RNA, vol. 3, 1997, pp. 1124-1134.
Patriarca, et al., "Lack of Significant Person-to-Person Spread of Swine Influenza-Like Virus Following Fatal Infection in an Immunocomprised Child". American Journal of Epidemiology, vol. 119, No. 2, 1984, pp. 152-158.
Paul et al., "Porcine Reproductive and Respiratory Syndrome: An Overview". Journal of Clinical Veterinary Medicine, vol. 11, No. 12, Nov. 1993, pp. 1-16.
Pearson et al., "Improved tools for biological sequence comparison". Proceedings of the National Academy of Sciences, vol. 85, Apr. 1988, pp. 2444-2448.
Pedersen et al., "Open Reading Frame 1a-Encoded Subunits of the Arterivirus Replicase Induce Endoplasmic Reticulum-Derived Double-Membrane Vesicles Which Carry the Viral Replication Complex". Journal of Virology, vol. 73, No. 3, Mar. 1999, pp. 2016-2026.

(56) References Cited

OTHER PUBLICATIONS

Pejsak et al., "Clinical signs and economic losses caused by porcine reproductive and respiratory syndrome virus in a large breeding farm". Veterinary Microbiology, vol. 44, 1997, pp. 317-322.

Peng et al., "Analysis of Second-Site Revertants of a Murine Coronavirus Nucleocapsid Protein Deletion Mutant and Construction of Nucleocapsid Protein Mutants by Targeted RNA Recombination". Journal of Virology, vol. 69, No. 6, Jun. 1995, pp. 3449-3457.

Penzes et al., "Characterization of a Replicating and Packaged Defective RNA of Avian Coronavirus Infectious Bronchitis Virus". vol. 203, No. 2, Sep. 1994, pp. 286-293.

Percy et al., "Expression of a Foreign Protein by Influenza A Virus". Journal of Virology, vol. 68, No. 7, Jul. 1994, pp. 4486-4492.

Phind Database, PJB Publications, Ltd., Surrey, GB; Abstract No. 00278268 & Animal-Pharm 230, 21-06-01.

Pirtle et al., "Morphologic Heterogeneity of a Strain of Swine Influenza Virus (A/Swine/Wisconsin/1/68, Hsw1N1) Propagated at Different Temperatures". American Journal of Veterinary Research, vol. 36, No. 1, 1975, pp. 1783-1787.

Plagemann et al., "Lactate Dehydrogenase-Elevating Virus, Equine Arteritis Virus, and Simina Hemorrhagic Fever Virus: A New Group of Positive-Strand RNA Viruses". Advances in Virus Research, vol. 41, 1991, pp. 99-192.

Pol et al., "Pathological, ultrastructural, immunohistochemical changes caused by Lelystad virus in experimentally induced infections of mystery swine disease (synonym: porcine epidemic abortion and respiratory syndrome (PEARS))". Veterinary Quarterly, vol. 13, No. 3, Jul. 1991, pp. 137-143.

Polson et al., "An evaluation of the financial impact of Porcine Reproductive and Respiratory Syndrome (PRRS) in nursery pigs". Proceedings of the 13th International Pig Veterinary Society Congress, Jun. 1994, p. 31.

Polson et al., "Financial Implications of Mystery Swine Disease (MSD)". 1993, pp. 8-28.

Polson, DD, "Answers to Your Questions on PRRS". NOBL Laboratories, 1993, 18 Pages.

Polson, DD, "RespPRRS a PRRS Vaccine Review". NOBL Laboratories, 1993, 22 pages.

Porcine Reproductive and Respiratory Syndrome: A Report on the Seminar Held in Brussels on Nov. 4-5, 1991 and Organized by the European Commission.

Poser, C.M., "Swine Influenza Vaccination: Truth and Consequences". Archives of Neurology, vol. 42, No. 11, 1985, pp. 1090-1092.

Potgieter et al., "Isolation of Swine Influenza Virus in Oklahoma". Journal of the American Veterinary Medical Association, vol. 171, No. 8, 1977, pp. 758-760.

Potts et al., "Peroxidase-labeled primary antibody method for detection of pestivirus contamination in cell cultures". Journal of Virological Methods, vol. 26, No. 1, Oct. 1989, pp. 119-124.

Quaife, T. "Mystery Agent Isolated". Swine Practitioner, Nov. 1991, p. 4.

Reed et al., "A Simple Method of Estimating Fifty Per Cent Endpoints"., The American Journal of Hygiene, vol. 27, No. 3, May 1938, pp. 493-497.

Reed et al., "Persistent Respiratory Virus Infection in Tracheal Organ Cultures". British Journal of Experimental Pathology, vol. 50, 1969, pp. 378-388.

Rice et al., "Production of Infectious RNA Transcripts from Sindbis Virus cDNA Clones: Mapping of Lethal Mutations, Rescue of a Temperature-Sensitive Marker, and in Vitro Mutagenesis to Generate Defined Mutants". Journal of Virology, vol. 61, No. 12, Dec. 1987, pp. 3809-3819.

Roberts et al., "Abortion in Swine". Veterinary Ostetrics and Genital Diseases, Edwards Brothers, Inc., Ann Arbor, 1986, pp. 180-192.

Kreutz, L.C., "Cellular membrane factors are the major determinants of porcine reproductive and respiratory syndrome virus tropism". Virus Research, vol. 53, 1998, pp. 121-128.

Kouvelos et al., "Comparison of Bovine, Simian and Human Rotavirus Structural Glycoproteins". Journal of General Virology, vol. 65, Jul. 1984, pp. 1211-1214.

Kundin, W.D., "Hong Kong A-2 Influenza Virus Infection among Swine during a Human Epidemic in Taiwan". Nature, vol. 228, Nov. 1970, p. 587.

Kuo et al., "A Nested Set of Eight RNAs Is Formed in Macrophages Infected with Lactate Dehydrogenase-Elevating Virus", Journal of Virology, vol. 65, No. 9, Sep. 1991, pp. 5118-5123.

Kusanagi et al., "Isolation and Serial Propagation of Porcine Epidemic Diarrhea Virus in Cell Cultures and Partial Characterization of the Isolate". Journal of Veterinary Medical Science, vol. 54, No. 2, 1992, pp. 313-318.

Kutsuzawa et al., "Isolation of Human Rotavirus Subgroups 1 and 2 in Cell Culture". Journal of Clinical Microbiology, vol. 16, No. 4, Oct. 1982, pp. 727-730.

Kwang et al., "Cloning, expression, and sequence analysis of the ORF4 gene of the porcine reproductive and respiratory syndrome virus MN-1b". Journal of Veterinary Diagnostic Investigation, vol. 6, No. 3, Jul. 1994, pp. 293-296.

Labarque et al., "Effect of cellular changes and onset of humoral immunity on the replication of porcine reproductive and respiratory syndrome virus in the lungs of pigs". Journal of General Virology, vol. 81, 2000, pp. 1327-1334.

Labarque et al., "Respiratory tract protection upon challenge of pigs vaccinated with attenuated porcine reproductive and respiratory syndrome virus vaccines". Veterinary Microbiology, vol. 95, 2003, pp. 187-197.

Lai et al., "Coronavirus: how a large RNA viral genome is replicated and transcribed". Infectious Agents and Disease, vol. 3, Nos. 2-3, 1994, pp. 98-105.

Lai et al., "Coronavirus: organization, replication and expression of genome". Annual Review of Microbiology, vol. 33, 1990, pp. 303-333.

Lai et al., "Infectious RNA transcribed from stably cloned full-length cDNA of dengue type 4 virus". Proceedings of the National Academy of Sciences, vol. 88, Jun. 1991, pp. 5139-5143.

Lazar et al. "Transforming Growth Factor a: Mutation of Aspartic Acid 47 and Leucine 48 Results in Different . Biological Activities". Molecular and Cellular Biology, vol. 8, No. 3, Marc. 1988, pp. 1247-1252.

Leitner et al., "DNA and RNA-based vaccines: principles, progress and prospects". Vaccine, vol. 18, 2000, pp. 765-777.

Levy et al., "Freeze-drying is an effective method for preserving infectious type C retroviruses". Journal of Virological Methods, Vol. 5, Nos. 3-4, Nov. 1982, pp. 165-171.

Liljestrom et al., "A New Generation of Animal Cell Expression Vectors Based on the Semliki Forest Virus Replicon". Nature Biotechnology, vol. 9, 1991, pp. 1356-1361.

Lin et al., "Deletion Mapping of a Mouse Hepatitis Virus Defective Interfering RNA Reveals the Requirement of an Internal and Discontiguous Sequence fro Replication". Journal of Virology, Vol. 67, No. 10, Oct. 1993, pp. 6110-6118.

Lin et al., "Identification of the cis-Acting Signal for Minus-Strand RNA Synthesis of a Murine Coronavirus: Implications for the Role of Minus-Strand RNA in RNA Replication and Transcription". Journal of Virology, vol. 68, No. 12, Dec. 1994, pp. 8131-8140.

Lin et al., "The 3' Untranslated Region of Coronavirus RNA Is Required for Subgenomic mRNA Transcription from a Defective Interfering RNA". Journal of Virology, vol. 70, No. 10, Oct. 1995, pp. 7236-7240.

Liu et al., "A Specific Host Cellular Protein Binding Element Near the 3? End of Mouse Hepatitis Virus Genomic RNA". Virology, vol. 232, No. 1, May 1997, pp. 74-85.

Loula et al., "Clinical Presentation of Mystery Pig Disease in the breeding herd and suckling piglets". Proceedings of the Mystery Swine Disease Committee Meeting, Denver, CO, Oct. 6, 1990.

Loula, T., "Mystery Pig Disease", Agri-Practice, vol. 12, No. 1, Jan.-Feb. 1991, pp. 29-34.

Luytjes et al., "Replication of Synthetic Defective Interfering RNAs Derived from Coronavirus Mouse Hepatitis Virus-A59". Virology, vol. 216, No. 1, Feb. 1996, pp. 174-183.

(56) References Cited

OTHER PUBLICATIONS

Lv et al., "An infectious cDNA clone of a highly pathogenic porcine reproductive and respiratory syndrome virus variant associated with porcine high fever syndrome". Journal of General Virology, vol. 89, 2008, pp. 2075-2079.
Madec et al., "Consequences pathologiques d'un episode grippal severe (virus swine A/H1N1 dans les conditions naturelles chez la truie non immune en debut de gestation". Comparative Immunology, Microbiology and Infectious Diseases, vol. 12, Nos. 1-2, 1989, pp. 17-27.
Madin, S.H. "Vesicular Exanthema Virus". Virus Infections of Porcines, Elsevier Science Publishers B.V., 1989, pp. 268-271.
Makable et al., "Hemagglutination with Ovine Rotavirus". Archives of Virology, vol. 90, 1986, pp. 153-158.
Makino et al., "Leader sequences of murine coronavirus mRNAs can be freely reassorted: Evidence for the role of free leader RNA in transcription". Proceedings of the National Academy of Sciences, vol. 83, Jun. 1986, pp. 4204-4208.
Makino et al., "Primary Structure and Translation of a Defective Interfering RNA of Murine Coronavirus". Virology, vol. 166, 1988, pp. 550-560.
Mardassi et al., "Identification of major differences in the nucleocapsid protein genes of a Québec strain and European strains of porcine reproductive and respiratory syndrome virus". vol. 75, No. 3, Mar. 1994, pp. 681-685.
Mardassi et al., "Molecular analysis of the ORFs 3 to 7 of porcine reproductive and respiratory syndrome virus, Québec reference strain". Archives of Virology, vol. 140, No. 8, 1995, pp. 1405-1418.
Mason, P.W., "Maturation of Japanese encephalitis virus glycoproteins produced by infected mammalian and mosquito cells". Virology, vol. 169, No. 2, Apr. 1989, pp. 354-364.
Masters et al., "Functions of the coronavirus nucleocapsid protein". Coronaviruses and Their Diseases, Plenum Press, New York, pp. 235-238.
Masurel, N., "Swine Influenza Virus and the Recycling of Influenza-A Viruses in Man". The Lancet, Jul. 31, 1976, pp. 244-247.
Mcauliffe et al., "Codon Substitution Mutations at Two Positions in the L Polymerase Protein of Human Parainfluenza Virus Type 1 Yield Viruses with a Spectrum of Attenuation in Vivo and Increased Phenotypic Stability in Vitro". Journal of Virology, vol. 78, No. 4, Feb. 2004, pp. 2029-2036.
Mccullough et al., "9. Experimental Transmission of Mystery Swine Disease", The New Pig Disease Porcine Respiration and Reproductive Syndrome, A report on the seminar/workshop held in Brussels on Apr. 29-30, 1991, pp. 46-52.
Mcdaniel, H.A., "African Swine Fever". Diseases of Swine, 5th Edition, Chapter 18, 1958, pp. 237-245.
Mcferran, J.B., "Reovirus Infection". Diseases of Swine, Fifth Edition, Chapter 28, 1958, pp. 330-336.
Mcintosh, "Diagnostic Virology". Fields Virology, Ch. 17, Second Edition, vol. 1, 1990, pp. 411-437.
Mckinney, W.P., "Fatal Swine Influenza Pneumonia During Late Pregnancy". Archives of Internal Medicine, vol. 150, No. 1, Jan. 1990, pp. 213-215.
Mcqueen et al., "Influenza in animals". Advances in Veterinary Science, vol. 12, 1968, pp. 285-336.
Meikeljohn et al., "Respiratory Virus Vaccine Evaluation and Surveillance". Semi-Annual Contract Progress Report to the National Institute of Allergy and Infectious Diseases, Sep. 15, 1965 to Mar. 15, 1966, 21 pgs.
Melchers et al., "Cross-talk between orientation-dependent recognition determinants of a complex control RNA element, the enterovirus oriR". RNA, vol. 6, 2000, pp. 976-987.
Mendez et al., "Molecular Characterization of Transmissible Gastroenteritis Coronavirus Defective Interfering Genomes: Packaging and Heterogeneity". Virology, vol. 217, 1996, pp. 495-507.
Meng et al., "Characterization of a High-Virulence US Isolate of Porcine Reproductive and Respiratory Syndrome Virus in a Continuous Cell Line, ATCC CRL11171". Journal of Veterinary Diagnostic Investigation, vol. 8, No. 3, Jul. 1996, pp. 374-381.

Meng et al., "Molecular cloning and nucleotide sequencing of the 3'-terminal genomic RNA of the porcine reproductive and respiratory syndrome virus". Journal of General Virology, vol. 75, 1994, pp. 1795-1801.
Meng et al., "Phylogenetic analyses of the putative M (ORF 6) and N (ORF 7) genes of porcine reproductive and respiratory syndrome virus (PRRSV): implication for the existence of two genotypes of PRRSV in the U.S.A. And Europe". Archives of Virology, vol. 140, No. 4, 1995, pp. 745-755.
Meng, X.J., "Heterogeneity of porcine reproductive and respiratory syndrome virus: implications for current vaccine efficacy and future vaccine development". Veterinary Microbiology, vol. 74, 2000, pp. 309-329.
Mengeling et al., "An update of research at the National Animal Disease Center on current field strains of Porcine Reproductive and Respiratory Syndrome (PRRS) virus". Allen D. Leman Swine Conference, 1997, pp. 138-145.
Mengeling et al., "Clinical consequences of exposing pregnant gilts to strains of porcine reproductive and respiratory syndrome (PRRS) virus isolated from field cases of "atypical" PRRS". American Journal of Veterinary Research, vol. 59, No. 12, Dec. 1998, pp. 1540-1544.
Roof et al., "Efficacy of Modified Live Virus Porcine Reproductive and Respiratory Virus Vaccines Against Heterologous Respiratory Challenge". 4th International Symposium on Emerging and Re-emerging Pig Diseases, Rome, Jun. 28-Jul. 2, 2003, pp. 117-118.
Ropp et al., "Characterization of Emerging European-Like Porcine Reproductive and Respiratory Syndrome Virus Isolates in the United States"., Journal of Virology, vol. 78, No. 7, Apr. 2004, pp. 3684-3703.
Rossow et al., "Experimental porcine reproductive and respiratory syndrome virus infection in one-, four-, and 10-week-old pigs". Journal of Veterinary Diagnostic Investigation, vol. 6, 1993, pp. 3-12.
Rossow, K.D., "Porcine Reproductive and Respiratory Syndrome". Veterinary Pathology, vol. 35, 1998, pp. 1-20.
Roth et al., "Influenza virus hemagglutinin expression is polarized in cells infected with recombinant SV40 viruses carrying cloned hemagglutinin DNA". Cell, vol. 33, No. 2, Jun. 1983, pp. 435-443.
Roth et al., "The large external domain is sufficient for the correct sorting of secreted or chimeric influenza virus hemagglutinins in polarized monkey kidney cells". The Journal of Cell Biology, vol. 104, Mar. 1987, pp. 769-782.
Rottier et al., "Predicted Membrane Topology of the Coronavirus Protein E1". Biochemistry, vol. 25, 1986, pp. 1335-1339.
Rovira et al., "Experimental Inoculation of Conventional Pigs with Porcine Reproductive and Respiratory Syndrome virus and Porcine Circovirus 2", J. Virol, jApr. 2002, vol. 76, No. 7, pp. 3232-3239.
Sagripanti et al., "The Cap Structure of Simian Hemorrhagic Fever Virion RNA". Virology, vol. 151, 1986, pp. 143-150.
Saif et al., "Serial propagation of porcine group C rotavirus (pararotavirus) in a continuous cell line and characterization of the passaged virus". Journal of Clinical Microbiology, vol. 26, No. 7, Jul. 1988, pp. 1277-1282.
Saif, L.J., "Coronavirus Immunogens". Veterinary Microbiology, vol. 37, No. 3-4, Nov. 1993, pp. 285-297.
Sarnow, P. "Role of 3'-End Sequences in Infectivity of Poliovirus Transcripts Made in Vitro". Journal of Virology, vol. 63, No. 1, Jan. 1989, pp. 467-470.
Sawicki et al., "Coronavirus Transcription: Subgenomic Mouse Hepatitis Virus Replicative Intermediates Function in RNA Synthesis". Journal of Virology, vol. 64, No. 3, Mar. 1990, pp. 1050-1056.
Schmidt et al., "Infection of Influenza a Viruses of Tracheal Organ Cultures Derived from Homologous and Heterologous Hosts". The Journal of Infectious Diseases, vol. 129, No. 1, 1974, pp. 28-36.
Scott, F.W., "Immunization against feline coronaviruses". Advances in Experimental Medicine and Biology, vol. 218, 1987, pp. 569-576.
Seal et al., "Analysis of the Serologic Relationship among San Miguel Sea Lion Virus and Vesicular Exanthema of Swine Virus Isolates. Application of the Western Blot Assay for Detection of Antibodies in Swine Sera to these Virus Types". Journal of Veterinary Diagnostic Investigation, vol. 7, No. 2, Apr. 1995, pp. 190-195.

(56) References Cited

OTHER PUBLICATIONS

Seal et al- "Isolation of caliciviruses from skunks that are antigenically and genotypically related to San Miguel sea lion virus Original Research". Virus Research, vol. 37, No. 1, Jun. 1995, pp. 1-12.
Seneca, H., "Influenza: epidemiology, etiology, immunization and management". Journal of American Geriatrics Society, vol. 28, No. 6, Jun. 1980, pp. 241-250.
Sethna et al., "Coronavirus subgenomic minus-strand RNAs and the potential for mRNA replicons". Proceedings of the National Academy of Sciences, vol. 86, Jul. 1989, pp. 5626-5630.
Setzer et al., "Size Heterogeneity in the 3' End of Dihydrofolate Reductase Messenger RNAs in Mouse Cells". Cell, vol. 22, Nov. 1980, pp. 361-370.
Shaw et al., "Experimental rotavirus infection in three-week-old pigs". American Journal of Veterinary Research, vol. 50, No. 11, Nov. 1989, pp. 1961-1965.
Shen et al., "Determination of the complete nucleotide sequence of a vaccine strain of porcine reproductive and respiratory syndrome virus and identification of the Nsp2 gene with a unique insertion". Archives of Virology, vol. 145, No. 5, May 2000, pp. 871-883.
Shibata et al., "Detection of Human Papilloma Virus in Paraffin-Embedded Tissue Using the Polymerase Chain Reaction". The Journal of Experimental Medicine, Vol. 167, No. 1, Jan. 1988, pp. 225-230.
Shieh et al., "The 5'-End Sequence of the Murine Coronavirus Genome: Implications of Multiple Fusion Sites in Leader-Primed Transcription". Virology, vol. 156, 1987, pp. 321-330.
Shin et al., "Assessment of Porcine Reproductive and Respiratory Syndrome Virus RNA Load in Sera and Tissues during Acute Infection". Journal of Veterinary Science, Vol. 3, No. 2, 2002, pp. 75-85.
Shope et al., "The Susceptibility of Swine to the Virus of Human Influenza". Annual Meeting of the Society of American Bacteriologists in New York, 1936, pp. 791-801.
Shortridge et al., "Geographical Distribution of Swine (HSw1N1) and Hong Kong (H3N2) Influenza Virus Variants in in Pigs in Southeast Asia". Intervirology, vol. 11, No. 1, 1979, pp. 9-15.
Skiadopoulos et al., "Identification of Mutations Contributing to the Temperature-Sensitive, Cold-Adapted, and Attenuation Phenotypes of the Live-Attenuated Cold-Passage 45 (cp45) Human Parainfluenza Virus 3 Candidate Vaccine". Journal of Virology, vol. 73, No. 2, Feb. 1999, pp. 1374-1381.
Smith et al., "Isolation of Swine Influenza Virus from Autopsy Lung Tissue of Man". New England Journal of Medicine, vol. 294, Mar. 1976, pp. 708-710.
Smith et al., "San Miguel Sea Lion Virus Isolation, Preliminary Characterization and Relationship to Vesicular Exanthema of Swine Virus". Nature, Vol. 244, Jul. 1973, pp. 108-110.
Snijder et al., "A 3'-Coterminal Nested Set of Independently Transcribed mRNAs Is Generated during Berne Virus Replication". Journal of Virology, vol. 64, No. 1, Jan. 1990, pp. 331-338.
Snijder et al., "Identification of a Novel Structural Protein of Arteriviruses". Journal of Virology, vol. 73, No. 8, Aug. 1999, pp. 6335-6345.
Snijder et al., "Non-structural proteins 2 and 3 interact to modify host cell membranes during the formation of the arterivirus replication complex". Journal of General Virology, vol. 83, 2001, pp. 985-994.
Snijder et al., "Proteolytic Processing of the Replicase ORF1a Protein of Equine Arteritis Virus". Journal of Virology, vol. 68, No. 9, Sep. 1994, pp. 5755-5764.
Snijder et al., "The carboxyl-terminal part of the putative Berne virus polymerase is expressed by ribosomal frameshifting and contains sequence motifs which indicate that toro- and coronaviruses are evolutionarily related". Nucleic Acids Research, vol. 18, No. 15, Aug. 1990, pp. 4535-4542.
Snijder et al., "The molecular biology of arteriviruses". Journal of General Virology, vol. 79, 1998, pp. 961-979.
Snijder et al., "Toroviruses: replication, evolution and comparison with other members of the coronavirus-like superfamily". Journal of General Virology, vol. 74, 1993, pp. 2305-2316.

Spaan et al., "Coronaviruses: Structure and Genome Expression". Journal of General Virology, vol. 69, 1988, pp. 2939-2952.
Stephen et al., "Swine Influenza Virus Vaccine: Potentiation in Rhesus Monkeys in Antibody Responses by a Nuclease Resistant Derivative of Ply I-Poly C". U.S. Army Medical Research Institute of Infectious Diseases, Fort Detrick, Frederick, MD 21701, 1976, 10 pages.
Stephen et al., "Swine influenza virus vaccine: potentiation of antibody responses in rhesus monkeys". Science, vol. 197, No. 4310, 1977, pp. 1289-1290.
Stevenson et al., "Endemic Porcine Reproductive and Respiratory Syndrome Virus Infection of Nursery Pigs in Two Swine Herds without Current Reproductive Failure". Journal of Veterinary Diagnostic Investigation, vol. 5, 1993, pp. 432-434.
Stim, T.B., "Arbovirus Plaquing in Two Simian Kidney Cell Lines". Journal of General Virology, vol. 5, No. 3, Oct. 1969, pp. 329-338.
Suarez et al., "Direct detection of the porcine reproductive and respiratory syndrome (PRRS) virus by reverse polymerase chain reaction (RT-PCR)". Archives of Virology, vol. 135, No. 1-2, 1994, pp. 89-99.
Suarez et al., "Phylogenetic relationships of European strains of porcine reproductive and respiratory syndrome virus (PRRSV) inferred from Dna sequences of putative ORF-5 and ORF-7 genes". Virus Research, vol. 42, Nos. 1-2, Jun. 1996, pp. 159-165.
Sumiyoshi et al., "Infectious Japanese Encephalitis Virus RNA Can Be Synthesized from in Vitro-Ligated cDNA Templates". Journal of Virology, vol. 66, No. 9, Sep. 1992, pp. 5425-5431.
Tahara et al., "Coronavirus Translational Regulation: Leader Affects mRNA Efficiency". Virology, vol. 202, No. 1, Aug. 1994, pp. 621-630.
Tao et al., "Host Range Restriction of Parainfluenza Virus Growth Occurs at the Level of Virus Genome Replication". Virology, vol. 220, 1996, pp. 69-77.
Tauraso et al., "Simian Hemorrhagic Fever: III. Characterization of a Viral Agent". The American Journal of Tropical Medicine and Hygiene, vol. 17, No. 3, May 1968, pp. 422-431.
Terpstra et al., "Experimental reproduction of porcine epidemic abortion and respiratory syndrome (mystery swine disease) by infection with Lelystad virus: Koch's postulates fulfilled". The Veterinary Quarterly, vol. 13, No. 3, Jul. 1991, pp. 131-136.
Thacker, B., "Clinical Manifestations of PRRS Virus". 2003 PRRS Compendium: Second Edition, National Pork Board, Des Moines, IA, 2003, pp. 7-15.
Drew et al., "Production, characterization and reactivity of monoclonal antibodies to porcine reproductive and respiratory syndrome virus". Journal of General Virology, vol. 76, 1995, pp. 1361-1369.
Drew, T., "Porcine Reproductive and Respiratory Syndrome Virus: A Review". Apr. 1996, 3 pages.
Duan et al., "Identification of a putative Receptor for Porcine Reproductive and Respiratory Syndrome Virus on Porcine Alveolar Macrophages". Journal of Virology, vol. 72, No. 5, May 1998, pp. 4520-4523.
Duran et al. "Recombinant Baculovirus Vaccines Against Porcine Reproductive and Respiratory Syndrome (PRRS)". Abstracts Prrs, Aug. 9-10, 1995, Copenhagen, Denmark, 2 pages.
Dykhuizen et al., "Determining the Economic Impact of the 'New' Pig Disease", Porcine Reproductive and Respiratory Syndrome, A Report on the Seminar Held in Brussels on Nov. 4-5, 1991 and Organized by the European Commission, pp. 53-60.
Easterday, et al., "Swine Influenza". In Diseases of Swine (8th Edition), BE Straw, S D'Allaire, WI. Mengeling, DJ Taylor, eds., Ames: Iowa State University Press, 1999, pp. 277-290.
Edwards et al., "Oligodeoxyribonucleotide ligation to single-stranded cDNAs: a new tool for cloning 5' ends of mRNAs and for constructing cDNA libraries by in vitro amplification". Nucleic Acids Research, vol. 19, No. 19, pp. 5227-5232.
Ehresmann et al., "RNA synthesized in calicivirus-infected cells is atypical of picornaviruses". Journal of Virology, vol. 22, No. 2, May 1977, pp. 572-576.
Ellis, R.W., "New Technologies for Making Vaccines". Vaccines, Chapter 29, Plotkin et al Eds., WB Saunders Company, Philadelphia, PA, 1988, pp. 568-575.

(56) References Cited

OTHER PUBLICATIONS

Enjuanes et al., "Isolation and Properties of the DNA of African Swine Fever (ASF) Virus". Journal of General Virology, vol. 32, No. 3, Sep. 1976, pp. 479-492.

*Enzo Biochem Inc. v. Gen-Probe Incorporated et al.*, No. 01-01230; Decided Jul. 15, 2002.

Estes et al., "Simian rotavirus SA11 replication in cell cultures". Journal of Virology, vol. 31, No. 3, Sep. 1979, pp. 810-815.

Fang et al., "Heterogeneity in nsp2 of European-like porcine reproductive and respiratory syndrome viruses isolated in the United States". Virus Research, vol. 100, 2004, pp. 229-235.

Fenner et al., "Immunization against Viral Diseases", Veterinary Virology, Ch. 14, 1992, pp. 265-271.

Fenner et al., "Viral Genetics and Evolution", Veterinary Virology, Ch. 5, 1992, pp. 89-95.

Ferrari et al., "Isolation of Cytopathic Strains of Rotavirus from Pigs". Microbiologica, vol. 9, No. 3, Jul. 1986, pp. 287-294.

Flint et al., "Virus Cultivation, Detection, and Genetics". Virology, Molecular Biology, Pathogenesis, and Control, Ch. 2, 2000, pp. 40-42.

Foss et al., "Adjuvant Danger Signals Increase the Immune Response to Porcine Reproductive and Respiratory Syndrome Virus". Viral Immunology, vol. 15, No. 4, 2002, pp. 557-566.

Frolov et al., "Alphavirus-based expression vectors: Strategies and applications". Proceedings of the National Academy of Sciences, vol. 93, Oct. 1996, pp. 11371-11377.

Fu et al., "Detection and survival of group a rotavirus in a piggery". Veterinary Record, vol. 125, 1989, pp. 576-578.

Fukuhara et al., "Evidence for endocytosis-independent infection by human rotavirus". Archives of Virology, vol. 97, Nos. 1-2, 1987, pp. 93-99.

Funkhouser et al., "Mutations in the 5'-noncoding, 2C and P3 Regions of the Genome Increase the Efficiency of Hepatitis a Virus Growth in MRC-5 Cells". Vaccines, vol. 94, Cold Springs Harbor Laboratory Press, 1994, pp. 345-349.

Garwest, D.J., "Transmissible gastroenteritis". Veterinary Record, vol. 122, 1988, pp. 462-463.

Geisbert et al., "Use of Immunoelectron Microscopy to Show Ebola Virus During the 1989 United States Epizootic". Journal of Clinical Pathology, vol. 43, No. 10, Oct. 1990, pp. 813-816.

Girard et al., "Experimentally induced porcine proliferative and necrotising pneumonia with an influenza a virus". The Veterinary Record, vol. 130, Mar. 1992, pp. 206-207.

Godeny et al., "Map location of lactate dehydrogenase-elevating virus (LDV) capsid protein (VPL) gene", Virology, vol. 177, No. 2, Aug. 1990, pp. 768-771.

Godeny et al., "The 3' Terminus of Lactate Dehydrogenase-Elevating Virus Genome RNA Does Not Contain Togavirus or Flavivirus Conserved Sequences", Virology, vol. 72, 1989, pp. 647-650.

Goldfield et al., "Influenza in New Jersey in 1976: Isolations of Influenza A/New Jersey/76 Virus at Fort Dix". The Journal of Infectious Diseases, Vol. 136, Supp. 3, 1977, pp. S347-S355.

Goldstein, et al., "Evaluation of Three Cell Culture Systems as Substrates for Influenza Virus Assay". Applied Microbiology, vol. 19, No. 4, Apr. 1970, pp. 580-582.

Gong et al., "Characterization of RNA synthesis during a one-step growth curve and of the replication mechanism of bovine viral diarrhoea virus". Journal of General Virology, Vol. 77, 1996, pp. 2729-2736.

Gorcyca et al., RespPRRS: A new tool for the prevention and control of PRRS in pigs. Proceedings of the American Association of Swine Practitioners, Omaha Nebraska, 1995, pp. 1-22.

Gourreau et al., "Diffusion du virus de la grippe du porc (H1N1=Hsw1N1) en France". Annales de l'Institut Pasteur/Virologie, vol. 132, No. 2, Apr.-Jun. 1981, pp. 287-294.

Goyal, S., "Porcine Reproductive and Respiratory Syndrome", Journal of Veterinary Diagnostic Investigation, vol. 5, No. 4, 1993, pp. 656-664.

Gravell et al., "Differences among isolates of simian hemorrhagic fever (SHF) virus". Proceedings of the Society for Experimental Biology and Medicine, vol. 181, No. 1, 1986, pp. 112-119.

Graves, J.H., "Swine Vesicular Disease". Fifth Edition, Chapter 23, 1958, pp. 288-293.

Grebennikova et al., "Genomic characterization of virulent, attenuated, and revertant passages of a North American porcine reproductive and respiratory syndrome virus strain". Virology, vol. 321, 2004, pp. 383-390.

Greiner et al., "Quantitative relationship of systemic virus concentration on growth and immune response in pigs". Journal of Animal Science, vol. 78, 2000, pp. 2690-2695.

Grizzard et al., "Experimental production of respiratory tract disease in cebus monkeys after intratracheal or intranasal infection with influenza A/Victoria/3/75 or influenza A/New Jersey/76 virus". Infection and Immunity, vol. 21, No. 1, Jul. 1978, pp. 201-205.

Grouse, L.D., "Swine Flue Sequelae"., Journal of the American Medical Association, vol. 243, No. 24, 1980, p. 2489.

Grunert et al., "Sensitivity of Influenza A/New Jersey/8/76 (HswlNl) Virus to Amantadine-HCl". Journal of Infectious Diseases, vol. 136, No. 2, 1977, pp. 297-300.

Guan et al., "Requirement of a 5?-Proximal Linear Sequence on Minus Strands for Plus-Strand Synthesis of a Satellite Rna Associated with Turnip Crinkle Virus". Virology, vol. 268, No. 2, Mar. 2000, pp. 355-363.

Gubler et al., "A simple and very efficient method for generating cDNA libraries". Gene, vol. 25, 1983, pp. 263-269.

Gustafson, D.P., "Pseudorabies". Diseases of Swine, Fifth Edition, Ch. 14, 1958, pp. 209-223.

Halbur et al., "Comparative pathogenicity of nine US porcine reproductive and respiratory syndrome virus (PRRSV) isolates in a five-week-old cesarean-derived, colostrum-deprived pig model". Journal of Veterinary Diagnostic Investigation, vol. 8, 1996, pp. 11-20.

Halbur et al., "Conference of Research Workers in Animal Diseases". Abstracts of Papers, Chicago, Illinois, paper #222, Nov. 1993.

Halbur et al., "Effects of different US isolates of porcine reproductive and respiratory syndrome virus (PRRSV) on blood and bone marrow parameters of experimentally infected pigs". Veterinary Record. Vol. 151, 2002, pp. 344-348.

Halbur et al., "Viral Pneumonia in Neonatal and Nursery pigs. Experimental Work with SIRS Agent and Evidence of Another New Viral Agent". Agri-Practice, vol. 12, No. 1, Jan-Feb. 1991, pp. 23-34.

Hao et al., "Polymorphic genetic characterization of the ORF7 gene of porcine reproductive and respiratory syndrome virus (PRRSV) in China". Virology Journal, vol. 8:73, pp. 1-9.

Harlow & Lane, Editors, "Antibodies, A Laboratory Manual". Cold Spring Harbor: Cold Spring Harbor Laboratory, New York, 1988, pp. 423, 464-468.

Haynes et al., "Temporal and Morphologic Characterization of the Distribution of Porcine Reproductive and Respiratory Syndrome Virus (PRRSV) by in Situ Hybridization in Pigs Infected with Isolates of PRSSV that Differ in Virulence". Veterinary Pathology, vol. 34, 1997, pp. 39-43.

Mengeling et al., "Clinical Effects of porcine reproductive and respiratory syndrome virus on pigs during the early postnatal interval". American Journal of Veterinary Research, vol. 59, No. 1, Jan. 1998, pp. 52-55.

Mengeling et al., "Comparative safety and efficacy of attenuated single-strain and multi-strain vaccines for porcine reproductive and respiratory syndrome". Veterinary Microbiology, vol. 93, 2003, pp. 25-38.

Mengeling et al., "Comparison among strains of porcine reproductive and respiratory syndrome virus for their ability to cause reproductive failure". American Journal of Veterinary Research, vol. 57, No. 6, Jun. 1996, pp. 834-839.

Mengeling et al., "Mystery Pig Disease: Evidence and Considerations for its Etiology". Proceedings of the Mystery Swine Disease Committee Meeting, Oct. 6, 1990, Denver, Colorado, Livestock Conservation Institute, Madison, WI, USA, pp. 88-90.

Mengeling et al., "Strain specificity of the immune response of pigs following vaccination with various strains of porcine reproductive and respiratory syndrome virus". Veterinary Microbiology, vol. 93, 2003, pp. 13-24.

(56) References Cited

OTHER PUBLICATIONS

Meredith, Mj, "Porcine Reproductive and Respiratory Syndrome (PRRS)", Pig Disease Information Center, 1st North American Edition, University of Cambridge, Aug.1994, pp. 1-57.

Mettenleiter et al., "Isolation of a viable herpesvirus (pseudorabies virus) mutant specifically lacking all four known nonessential glycoproteins". Virology, Vol. 179, No. 1, Nov. 1990, pp. 498-503.

Meulenberg et al., "An infectious cDNA clone of Porcine Reproductive and Respiratory Syndrome Virus". Coronaviruses and Arteriviruses (Advances in Experimental Medicine and Biology, vol. 440), Ch. 24, 1998, pp. 199-206.

Meulenberg et al., "Characterization of Proteins Encoded by ORFs 2 to 7 of Lelystad Virus". Virology, vol. 206, No. 1, Jan. 1995, pp. 155-163.

Meulenberg et al., "Identification and Characterization of a Sixth Structural Protein of Lelystad Virus: The Glycoprotein GP2Encoded by ORF2 Is Incorporated in Virus Particles". Virology, vol. 225, No. 1, Nov. 1996, pp. 44-51.

Meulenberg et al., "Infectious Transcripts from Cloned Genome-Length cDNA of Porcine Reproductive and Respiratory Syndrome Virus". Journal of Virology, vol. 72, No. 1, Jan. 1998, pp. 380-387.

Meulenberg et al., "Lelystad Virus, the Causative Agent of Porcine Epidemic Abortion and Respiratory Syndrome (PEARS), is Related to LDV and EAV". Virology, vol. 192, 1993, pp. 62-72.

Meulenberg et al., "Localization and Fine Mapping of Antigenic Sites on the Nucleocapsid Protein N of Porcine Reproductive and Respiratory Syndrome Virus with Monoclonal Antibodies". Virology, vol. 252, 1998, pp. 106-114.

Meulenberg et al., "Molecular characterization of Lelystad virus". Veterinary Microbiology, vol. 55, 1997, pp. 197-202.

Meulenberg et al., "Nucleocapsid Protein N of Lelystad Virus: Expression by Recombinant Baculovirus, Immunological Properties, and Suitability for Detection of Serum Antibodies". Clinical and Diagnostic Laboratory Immunology, vol. 2, No. 6, Nov. 1995, pp. 652-656.

Meulenberg et al., "Posttranslational Processing and Identification of a Neutralization Domain of the GP4 Protein Encoded by ORF4 of Lelystad Virus". Journal of Virology, vol. 71, No. 8, Aug. 1997, pp. 6061-6067.

Meulenberg et al., "Subgenomic RNAs of Lelystad virus contain a conserved leader-body junction sequence". Journal of General Virology, vol. 74, 1993, pp. 1697-1701.

Molenkamp et al., "Isolation and Characterization of an Arterivirus Defective Interfering RNA Genome". Journal of Virology, vol. 74, No. 7, 2000, pp. 3156-3165.

Molenkamp et al., "The arterivirus replicase is the only viral protein required for genome replication and subgenomic mRNA transcription". Journal of General Virology, vol. 81, No. 10, 2000, pp. 2491-2496.

Montagnon et al., "Polio and rabies vaccines produced in continuous cell lines: a reality for Vero cell line". Dev Biol Stand., vol. 70, 1989, pp. 27-47.

Moore, et al., "Porcine Proliferative and Necrotyzing Pneumonia Clinical Findings". Presented at American Association of Swine Practitioners, 22nd Annual Meeting, Mar. 3-5, 1991, pp. 443-453.

Moormann et al., "Hog cholera virus: identification and characterization of the viral RNA and the virus specific RNA synthesized in infected swine kidney cells". Virus Research, vol. 11, 1988, pp. 281-291.

Moormann et al., "Infectious RNA Transcribed from an Engineered Full-Length cDNA Template of the Genome of a Pestivirus". Journal of Virology, vol. 70, No. 2, Feb. 1996, pp. 763-770.

Moormann et al., "Molecular cloning and nucleotide sequence of hog cholera virus strain brescia and mapping of the genomic region encoding envelope protein E1". Virology, vol. 177, No. 1, Jul. 1990, pp. 184-198.

Morin et al., "Severe proliferative and necrotizing pneumonia in pigs: A newly recognized disease". Canadian Veterinary Journal, vol. 31, Dec. 1990, pp. 837-839.

Morozov et al., "Sequence analysis of open reading frames (ORFs) 2 to 4 of a U.S. isolate of porcine reproductive and respiratory syndrome virus". Archives of Virology, vol. 140, No. 7, 1995, pp. 1313-1319.

Morrison et al., "Brief Communications Serologic evidence incriminating a recently isolated virus (ATCC VR-2332) as the cause of swine infertility and respiratory syndrome (SIRS)". Journal of Veterinary Diagnostic Investigation, vol. 4, No. 2, Apr. 1992, pp. 186-188.

Morrison et al., "Sero-epidemiologic Investigation of Swine Infertility and Respiratory Syndrome (SIRS)". 72st Annual Meeting of the Conference of Research Workers in Animal Disease, Chicago, IL, Nov. 11-12, 1991, p. 55, Abstract No. 309.

Mountz et al., "The in vivo generation of murine IgD-secreting cells is accompanied by deletion of the Cμ gene and occasional deletion of the gene for the Cd1 domain". The Journal of Immunology, vol. 145, No. 5, Sep. 1990, pp. 1583-1591.

Mukamoto et al., "Immunogenicity in Aujeszky's disease virus structural glycoprotein gVI (gp50) in swine". Veterinary Microbiology, vol. 29, No. 2, Oct. 1991, pp. 109-121.

Murakami, et al., "Difference in growth behavior of human, swine, equine, and avian influenza viruses at a high temperature". Archives of Virology, vol. 100, Nos. 3-4, 1988, pp. 231-244.

Murphy et al., "Immunization Against Virus" in Virology, 2nd Edition, vol. 1, Fields, et al., eds. Raven Press, NY, 1990, pp. 469-502.

Murphy et al., "Virus Taxonomy". Chapter 2 in Fields Virology, 2nd. Edition, Fields, et al., eds, Raven Press, New York, 1990, pp. 9-35.

Murtaugh et al., "Comparison of the structural protein coding sequences of the VR-2332 and Lelystad virus strains of the PRRS virus". Archives of Virology, vol. 140, No. 8, 1995, pp. 1451-1460.

Murtaugh et al., "Genetic Variation in the Prrs Virus". Coronaviruses and Arteriviruses, Plenum Press, New York, 1998, pp. 787-794.

Murtaugh et al., "Immunological Responses of Swine to Porcine Reproductive and Respiratory Syndrome Virus Infection". Viral Immunology, vol. 15, No. 4, 2002, pp. 533-547.

Murtaugh et al., "Role of Viral Proteases in PRRS Immunity, Project Period Sep. 1, 1997-Dec. 31, 2002, no cost extension Jan. 1, 2003-Jun. 30, 2003". Final Report: Aug. 30, 2003, Department of Veterinary Pathology, University of Minnesota, St. Paul, MN and Boehringer Ingelheim Vetmedica, Inc., Ames, IA, 2003, pp. 1-38.

Murtaugh, "Allen D Lehman Swine Conference: the Evolution of the Swine veterinary profession: The PRRS Virus". University of Minnesota, Veterinary Continuing Education and Extension, vol. 20, 1993, pp. 43-47.

Myers et al., "Propagation of avian rotavirus in primary chick kidney cell and MA104 cell cultures". Avian Diseases, vol. 33, No. 3, Jul.-Sep. 1989, pp. 578-581.

Nakamura et al., "Studies on Swine Influenza III. Propagation of Swine Influenza Virus in Explants of Respiratory Tract Tissues from Fetal Pigs". Studies on Swine Influenza, 1968, pp. 27-35.

Narayanan et al., "Characterization of the Coronavirus M Protein and Nucleocapsid Interaction in Infected Cells". Journal of Virology, vol. 74, No. 17, Sep. 2000, pp. 8127-8134.

NCBI: Accession No. AE005172. "Arabidopsis thaliana chromosome 1, top arm complete sequence." Dec. 14, 2000.

NCBI: Accession No. AF046869. "Porcine reproductive and respiratory syndrome virus isolate 16244B, Feb. 18, 1997 (Nebraska) pass.3, complete genome." Mar. 17, 1999.

NCBI: Accession No. AF066183. "Porcine reproductive and respiratory syndrome virus RespPRRS MLV, complete genome." Feb. 22, 2001.

NCBI: Accession No. AF159149. "Porcine reproductive and respiratory syndrome virus isolate MLV RespPRRS/Repro, complete genome." Aug. 28, 2000.

NCBI: Accession No. AF176348. "Porcine reproductive and respiratory syndrome virus isolate PA8 complete genome." Sep. 3, 2002.

NCBI: Accession No. AF184212. "Porcine reproductive and respiratory syndrome virus strain SP, complete genome." Sep. 28, 2000.

NCBI: Accession No. AF325691. "Porcine reproductive and respiratory syndrome virus isolate NVSL 977985 IA 1-4-2, complete genome." Feb. 11, 2001.

NCBI: Accession No. AF331831. "Porcine reproductive and respiratory syndrome virus Bj-4, complete genome." Jan. 15, 2001.

(56) References Cited

OTHER PUBLICATIONS

NCBI: Accession No. M96262. "Lelystad virus, complete genome." Nov. 8, 2000.
Edwards et al., "Oligodeoxyribonucleotide ligation to single-stranded cDNAs: a new toll for cloning 5' ends of mRNAs and for constructing cDNA libraries by invitro amplification". Nucleic Acids Research, vol. 19, No. 19, 1991, pp. 5227-5232.
Hao et al., "Polymorphic genetic charachterization of the ORF7 gene of porcine reproductive and respiratory syndrome virus (PRRSV) in China". Virology Journal, vol. 8, No. 73, 2011, pp. 1-9.
Masters et al., "Functions of the coronavirus nucleocapsid nucleocapsid protein". Coronaviruses and Their Diseases, Plenum Press, New York, 1990, pp. 235-238.
Wootton et al., "Structure-function of the ORF7 protein of porcine reproductive and respiratory syndrome virus in the viral capsid assembly". Proceedings of the International Symposium on PRRS and Aujeszky's Disease, Ploufragan, France, Jun. 21-24, 1999, pp. 37-38.

* cited by examiner

US 8,741,309 B2

PORCINE REPRODUCTIVE AND RESPIRATORY SYNDROME VACCINE BASED ON ISOLATE JA-142

RELATED APPLICATION

This is a divisional application of application Ser. No. 10/654,545 filed Sep. 3, 2003 now U.S. Pat. No. 7,081,342 which is a continuation of application Ser. No. 09/981,282 filed Oct. 18, 2001, which issued as U.S. Pat. No. 6,641,819, which is a continuation-in-part of application Ser. No. 09/461,879 filed Dec. 15, 1999, which is now abandoned, which is a continuation-in-part of application Ser. No. 09/298,110 filed Apr. 22, 1999, which is now abandoned.

SEQUENCE DISCLOSURE

A Sequence Listing in the form of a computer readable ASCII file in connection with the present invention was filed in application Ser. No. 09/981,282. This earlier filed CRF is incorporated herein by reference and applicant requests that this previously filed CRF be used as the CRF for this application. A paper copy of this sequence is included herein and is identical to this previously-filed CRF.

BACKGROUND OF THE INVENTION

1. Field of the Invention

The present invention is broadly concerned with attenuated avirulent atypical porcine reproductive and respiratory syndrome (PRRS) virus (PRRSV), and corresponding live virus vaccines for administration to swine in order to confer effective immunity in the swine against PRRSV. The invention also includes methods of immunizing swine against PRRSV, and a new, highly efficient method of passaging viruses to attenuation. Furthermore, the invention provides methods of detecting and differentiating between field strains and an attenuated strain of PRRSV.

2. Description of the Prior Art

PRRS emerged in the late 1980's as an important viral disease of swine. PRRSV causes severe reproductive failure in pregnant sows, manifested in the form of premature farrowings, increased numbers of stillborn, mummified and weak-born pigs, decreased farrowing rate, and delayed return to estrus. Additionally, the respiratory system of swine infected with PRRSV is adversely affected, which is evidenced by lesions that appear in the lungs of infected swine. To combat the problems associated with PRRSV infection, vaccines have been developed which conferred immunity to then extant PRRSV strains.

Epidemics of an unusually severe form of PRRS, referred to hereafter as "atypical PRRS", were first recognized in North America in the latter part of 1996. They differed from epidemics of "typical PRRS" in that: 1) clinical signs were more prolonged as well as more severe; 2) the incidence of abortion was greater, especially during early and middle gestation; 3) there was a higher incidence of gilt and sow mortality; 4) PRRSV was less often isolated from aborted fetuses, stillborn pigs, and liveborn pigs—perhaps because abortions were more often the result of acute maternal illness rather than transplacental infection; 5) lung lesions of young affected pigs were more extensive; and 6) commercially available vaccines provided little or no protection. Collectively these observation indicated the emergence of more virulent and antigenically distinct strains of PRRSV and the need for a new generation of PRRS vaccines.

The most frequently used method for producing attenuated, live-virus vaccine is to serially passage the virus in a substrate (usually cell culture) other than the natural host (S) until it becomes sufficiently attenuated (i.e., reduced in virulence or diseases-producing ability) to be used as a vaccine. For the first passage, a cell culture is infected with the selected inoculum. After obtaining clear evidence of virus replication (e.g., virus-induced cytopathic effects [CPE] in the infected cells), an aliquot of the cell culture medium, or infected cells, or both, of the first passage are used to infect a second cell culture. The process is repeated until one or more critical mutations in the viral genome cause sufficient attenuation so that the virus can be safely used as a vaccine. The degree of attenuation is usually determined empirically by exposing the natural host (S) to progressively greater passage levels of the virus.

The above procedure is fundamentally sound and has been successfully used for the development of numerous vaccines for human and veterinary use. However, it is relatively inefficient because the logarithmic phase of virus replication, during which mutations are most likely to occur, is often completed long before evidence of virus replication becomes visibly obvious.

Therefore, there is a decided need in the art for a vaccine that confers effective immunity against PRRSV strains, including recently discovered atypical PRRSV strains. There is also a need in the art for a method of making such a vaccine. Finally, what is needed is a method of passaging a virus that attenuates the virus more efficiently than was heretofore thought possible with the resulting attenuated virus eliciting PRRSV specific antibodies in swine thereby conferring effective immunity against subsequent infection by PRRSV.

SUMMARY OF THE INVENTION

The present invention overcomes the problems outlined above, and provides attenuated, atypical PRRSV strains, and corresponding improved modified-live vaccines which confer effective immunity to newly discovered atypical PRRSV strains. "Effective immunity" refers to the ability of a vaccine to prevent swine PRRSV infections, including atypical PRRSV infections, which result in substantial clinical signs of the disease. That is to say, the immunized swine may or may not be serologically positive for PRRSV, but do not exhibit any substantial clinical symptoms. "Atypical PRRSV" refers to these new strains of PRRSV that are substantially more virulent than typical PRRSV strains.

In preferred forms, the vaccine of the invention includes live virus which has been attenuated in virulence. The resulting attenuated virus has been shown to be avirulent and to confer effective immunity. A particularly virulent strain of atypical PRRS (denominated JA-142) which caused especially severe symptoms of PRRS and represents the dominant strain of atypical PRRSV, was chosen for subsequent attenuation through passaging. The resultant attenuated virus has been deposited in the American Type Culture Collection (ATCC), Rockville, Md. on Feb. 2, 1999, and was accorded ATCC Accession No. VR-2638. This attenuated virus is a preferred Master Seed Virus (MSV) which has been subsequently passaged and developed as an effective PRRSV vaccine.

The name given the unattenuated virus, JA-142, arises from the restriction enzyme pattern. The 1 represents the inability of the enzyme MLUI to cleave the virus in open reading frame 5 (ORF 5). The 4 represents cleavage by Hinc II at base pair positions 118 and 249 of ORF 5 and short contiguous sequences. The 2 represents cleavage by Sac II at base pair position 54 of ORF 5 and short contiguous sequences.

Additionally, the present invention provides another way to differentiate between field strains of PRRSV and strain JA-142. The method is based upon differences in RNA cleavage by a restriction enzyme, NspI. Briefly, isolated PRRSV RNA is subjected to digestion by NspI. Digestion of the attenuated strain, JA-142, results in at least one additional fragment in comparison to field strains of PRRSV. In preferred methods, the RNA is isolated and RT-PCR is performed on the isolated RNA. This RNA is then subject to electrophoresis and a 1 Kd product is identified and purified for digestion by NspI. This digestion results in three fragments for JA-142 and either one or two fragments for PRRSV field strains.

Passaging of the virus to attenuation was accomplished using a novel method which resulted in increased efficiency. Specifically, the virus was kept in the logarithmic phase of replication throughout multiple cell culture passages in order to materially shorten the time to attenuation. This is achieved by ensuring that in each cell culture there is a substantial excess of initially uninfected cells relative to the number of virus present. Thus, by transferring only small numbers of virus from passage-to-passage, logarithmic replication is assured.

In practice, the process is normally initiated by inoculation of several separate cell cultures with progressively smaller viral aliquots (i.e., lesser numbers of virus in each culture.) For example, starting cultures could contain 200 µl, 20 µl and 2 µl viral aliquots. After an initial short incubation period (e.g., ~24 hours), the same viral aliquots (in the example, 200 µl, 20 µl and 2 µl) from each cell culture are transferred to individual fresh (previously uninfected) cultures, while the starting cultures are monitored until cytopathic effect (CPE) is or is not observed. This process is continued in serial order for multiple passages, using the same viral aliquots in each case and preserving the cultures for CPE observation. If all of the serial culture passages exhibit CPE after a selected number of passages are complete, the larger viral aliquot series may be terminated (in the example 200 µl and 20 µl), whereupon another series of progressively smaller viral aliquots are employed (e.g., 2 µl, 0.2 µl and 0.02 µl) and the process is again repeated, again keeping the cell cultures after transfer for CPE observation.

At some point in this successively smaller viral aliquot inoculation process, CPE will not be observed in a given cell culture. When this occurs, the next higher viral aliquot level showing CPE is substituted for the passage in which CPE was not observed, whereupon subsequent passages will be inoculated using previously employed viral aliquots.

Inasmuch as a virus will tend to become more efficient at infecting cells and also replicate to a higher infectivity titer for cell cultures over time, (which is especially true with RNA viruses such as PRRSV), it will be seen that smaller and smaller viral aliquots are required to maintain infection during serial transfer. The use of the smallest aliquot that maintains infection helps to assure that viral replication remains in a logarithmic phase throughout the process.

The DNA sequence of the attenuated passaged virus from the 201st passage was then determined using conventional methods. The sequence of this attenuated virus was designated as MSV JA-142 Passage No. 201, the sequence of which is given as SEQ ID No. 1. The sequence of the virulent virus, JA-142, is given as SEQ ID No. 2.

As used herein, the following definitions will apply: "Sequence Identity" as it is known in the art refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol., 215:403-410 (1990). The BLASTX program is publicly available from NCBI and other sources (BLAST Manual, Altschul, S. et al., NCVI NLM NIH Bethesda, Md. 20894, Altschul, S. F. et al., J. Molec. Biol., 215:403-410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 95% "sequence identity" to a reference nucleotide sequence, it is intended that the nucleotide sequence of the given polynucleotide is identical to the reference sequence except that the given polynucleotide sequence may include up to 5 point mutations per each 100 nucleotides of the reference nucleotide sequence. In other words, in a polynucleotide having a nucleotide sequence having at least 95% identity relative to the reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 95% sequence identity to a reference amino acid sequence, it is intended that the given amino acid sequence of the polypeptide is identical to the reference sequence except that the given polypeptide sequence may include up to 5 amino acid alterations per each 100 amino acids of the reference amino acid sequence. In other words, to obtain a given polypeptide sequence having at least 95% sequence identity with a reference amino acid sequence, up to 5% of the amino acid residues in the reference sequence may be deleted or substituted with another amino acid, or a number of amino acids up to 5% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity.

Similarly, "sequence homology", as used herein, also refers to a method of determining the relatedness of two sequences. To determine sequence homology, two or more sequences are optimally aligned as described above, and gaps are introduced if necessary. However, in contrast to "sequence identity", conservative amino acid substitutions are counted as a match when determining sequence homology. In other words, to obtain a polypeptide or polynucleotide having 95% sequence homology with a reference sequence, 95% of the amino acid residues or nucleotides in the reference sequence must match or comprise a conservative substitution with another amino acid or nucleotide, or a number of amino acids or nucleotides up to 5% of the total amino acid residues or nucleotides, not including conservative substitutions, in the reference sequence may be inserted into the reference sequence.

A "conservative substitution" refers to the substitution of an amino acid residue or nucleotide with another amino acid residue or nucleotide having similar characteristics or properties including size, hydrophobicity, etc., such that the overall functionality does not change significantly.

Isolated" means altered "by the hand of man" from its natural state., i.e., if it occurs in nature, it has been changed or removed from its original environment, or both. For example, a polynucleotide or polypeptide naturally present in a living organism is not "isolated," but the same polynucleotide or polypeptide separated from the coexisting materials of its natural state is "isolated", as the term is employed herein.

Preferably, sequences sharing at least about 75%, more preferably at least about 85%, still more preferably at least about 90% and most preferably at least about 95% sequence homology with SEQ ID No. 1 are effective as conferring immunity upon animals vaccinated with attenuated viruses containing such homologous sequences. Alternatively, sequences sharing at least about 65%, more preferably at least about 75%, still more preferably at least about 85%, and most preferably at least about 95% sequence identity with SEQ ID No. 1 are also effective at conferring immunity upon animals vaccinated with attenuated viruses containing such identical sequences.

DETAILED DESCRIPTION OF THE PREFERRED EMBODIMENT

Figure 1:
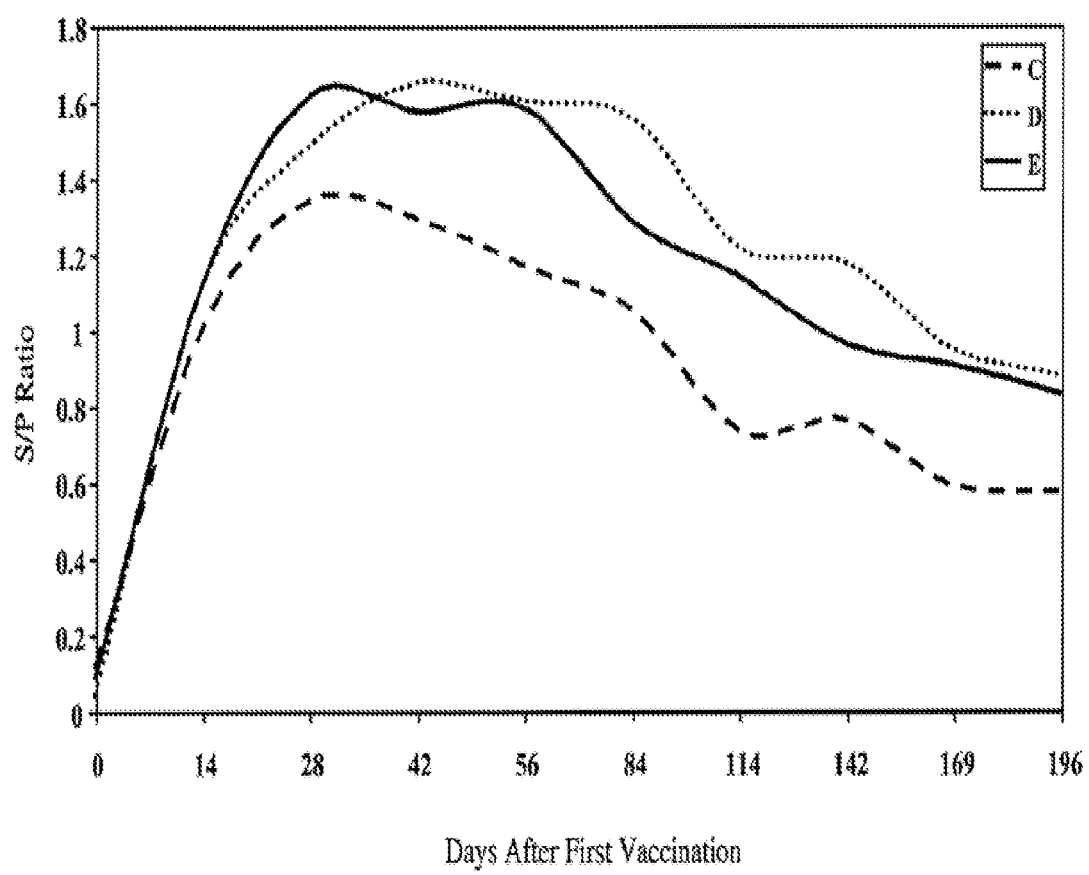
FIG. 1 is a graph illustrating the ratio of samples which tested positive for antibodies against PRRSV to the total number of samples over a 196 day testing period.

The following examples set forth preferred embodiments of the present invention. It is to be understood, however, that these examples are provided by way of illustration and nothing therein should be taken as a limitation upon the overall scope of the invention.

Example 1

Materials and Methods

This example describes a passage method of attenuating viruses which maximizes attenuation efficiency by ensuring that the virus is preferably in a logarithmic phase of replication. Virus was passed (i.e. an aliquot of nutrient medium including the virus, unattached cells, and cell debris from a virus-infected cell culture was added to the nutrient medium of a noninfected culture) at daily intervals. Different amounts of virus were added at each interval by using multiple cultures. For example, at the beginning, 200 µl was transferred to one noninfected culture, 20 µl was added to a second noninfected culture, and 2 µl to a third noninfected culture. The goal was to have a sufficient amount of susceptible cells so that the replication cycles could continue until the next transfer. The procedure was deemed successful if the cells eventually showed CPE. However, because PRRSV-induced CPE do not appear until sometime after the logarithmic growth phase, passages were made before it was known whether or not they would be ultimately successful ("blind passages"). Passages that resulted in virus induced CPE were said to have resulted in a "take". If a passage did not result in a take, the passage was restarted using the highest dilution from the last passage which did result in a take. As more and more passages were made, the virus became more adapted to replicate in the cell line and less able to produce disease symptoms in its original host. These changes occur through random mutations that occur during replication.

Using this method, the following procedures were used to passage an exemplary virus in accordance with the present invention, MSV, JA-142. This strain was passaged in MARC-145 cell cultures at daily intervals. Twenty-four-well plates were used for the process to minimize the amount of cells and nutrient medium required, and to simplify the multiple-aliquot passage technique. Cells and nutrient medium were added to each well and the cells were allowed to form, or nearly form (greater than about 70%), a confluent monolayer. The nutrient medium comprised approximately 90% Earle's balanced salt solution minimal essential medium (MEM), 10% fetal calf serum and 0.05 mgm/ml of gentamicin sulfate. The volume of nutrient medium used was approximately 1 ml. Usually, three wells of a column were used for each amount of virus that was transferred. An aliquot of nutrient medium from the previous passage was transferred to the first well in the column at 48 or 72 hours, after the cell cultures had been prepared, nutrient medium from the first well was transferred to the second well of the same column at 72 or 96 hours and the third well of the same column at 96 or 120 hours. Plates were usually set up twice a week so sometimes the fourth well of the column was used and sometimes it was not used. Passaging conditions were maintained at 37° C. in a moist atmosphere containing 5% $CO_2$.

Different sized aliquots (having different amounts of virus) for each passage were tested to determine if the amount of virus was sufficient to induce CPE. For example, a separate series of aliquot transfers (passages) of 200 μl, 20 μl, and 2 μl, respectively, was used until the smaller aliquots consistently exhibited CPE with the goal being to transfer the smallest aliquot that produced CPE. When the smallest aliquot (e.g. 2 μl) of the group of aliquots being tested consistently resulted in CPE, smaller amounts were tested (e.g. 0.2 μl and 0.02 μl). When a certain dilution did not exhibit CPE, that series of cultures was restarted with the next lower amount which did result in CPE at that passage (i.e. if the 2 μl transfer was unsuccessful at producing CPE in the 25th passage but the 20 μl transfer in the 25th passage was successful, the 2 μl transfer was repeated using 20 μl with 2 μl transfers resuming for the 26th passage.)

Using this method, the smallest amount of virus necessary to transfer to obtain CPE was determined. Virus was passed successfully at daily intervals using the following amounts of virus-infected nutrient medium (which reflect the highest dilution [i.e., smallest aliquot] which resulted in CPE keeping in mind that other dilutions would also work):

| Passage Number | Amount Transferred |
|---|---|
| 3-21 | 200 μl |
| 22, 23 | 20 μl |
| 24-41 | 200 μl |
| 42-83 | 20/200 μl (alternating) |
| 84-90 | 20 μl |
| 91-112 | 2 μl |
| 113 | 0.2 μl |
| 114-116 | 2 μl |
| 117 | 0.2 μl |
| 118-120 | 2 μl |
| 121 | 0.2 μl |
| 122-124 | 2 μl |
| 125-167 | 0.2 μl |
| 168 | 0.02 μl |
| 169-171 | 0.2 μl |
| 172 | 0.02 μl |
| 173-175 | 0.2 μl |
| 176 | 0.02 μl |
| 177-179 | 0.2 μl |
| 180 | 0.02 μl |
| 181-183 | 0.2 μl |
| 184 | 0.02 μl |
| 185-187 | 0.2 μl |
| 188 | 0.02 μl |
| 189-191 | 0.2 μl |
| 192 | 0.02 μl |
| 193-195 | 0.2 μl |
| 196 | 0.02 μl |
| 197 | 0.2 μl |

Results and Discussion

The passaging of the virus using the above method resulted in an attenuated PRRSV, JA-142. As is apparent, the virus became more adapted to replicate in the cell culture and therefore required a smaller amount of virus-infected nutrient medium to be transferred as passaging continued. For transfers using a very small amount of virus-infected nutrient medium (e.g. 0.2 μl or 0.02 μl), a separate dilution was required. This dilution was accomplished by adding a small amount of virus-infected nutrient medium to a larger amount of nutrient medium. For example, to obtain a transfer of 0.2 μl, 2 μl of virus infected nutrient medium was added to 20 μl of nutrient medium and 2 μl of this dilution was added to the next culture in the series. Using this approach, the highest dilution which resulted in CPE was used and the time necessary for passaging the virus was minimized. Passaging at daily intervals ensured that the virus was always in a logarithmic phase of replication. Daily transferring also ensured that there was an adequate number of cells for virus replication.

Because the mutations (which are probably cumulative) that are likely to result in attenuation only occur during replication, there is no advantage to having substantially all cells infected and replication either proceeding at a slower rate or stopping before the next transfer. Based on previous studies of PRRSV, it was known that the replication cycle is about 8 hours, therefore, transferring a minimal amount of virus from virus-infected nutrient medium to uninfected nutrient medium at daily intervals results in the virus always having plenty of cells within which to replicate.

As can be readily appreciated, passaging using this method results in a savings of time that was heretofore thought impossible (i.e. each passage required less time). This is especially important when a high number of passages are required for adequate virus attenuation. If each passage, using old methods, was performed at a 3 day interval, a procedure requiring 200 passages would take 400 fewer days using the method of the present invention.

Example 2

Materials and Methods

This example determined if passage 200 of PRRS Virus, JA-142, would revert in virulence when passed in the host animal six times. This study consisted of six groups. Five pigs from group 1 (principle group) were inoculated intra-nasally with PRRS MSV, JA-142 passage 200, while three pigs from group 1A, (control group) were inoculated intra-nasally with sterile diluent. The animals were provided commercial feed and water ad libitum throughout the study. Pigs of both treatment groups were monitored daily for clinical signs (appearance, respiratory, feces, etc.). After six days, the animals were weighed, bled and sacrificed. After scoring the lungs for lesions, lung lavages were collected from each animal. The lung lavages were frozen and thawed one time, and a pool was prepared using 2.0 ml of serum and 2.0 ml of lung lavage from each animal within a group to prepare Backpassage 1 and 1A, respectively. This pool was used to challenge (intra-nasally) the animals in group 2 and group 2A, respectively. This process was repeated for groups 3 and 3A through 6 and 6A. Animals in each group were housed in separate but identical conditions.

Following inoculation, blood samples were collected and body temperatures were monitored. Rectal temperatures were measured for each animal periodically from −1 DPE (days post exposure) to 6 DPE and averaged together with other animal temperatures from the same group. The health status of each animal was monitored daily for the duration of the study. Results were compiled and scored on a daily observation form. The scoring parameters are as follows:

1. Appearance
    normal=0; depressed=1; excited=2; comatose/death=30.
2. Respiration
    normal=0; sneeze=1; cough=1; rapid/short=2; labored=3.
3. Feces
    normal=0; dry=1; loose=2; fluid=3.
4. Eyes
    normal=0; watery=1; matted=2; sunken=3.

5. Nostrils
   normal=0; watery discharge=1; red/inflamed=2; crusted ulcers=3.
6. Mouth
   normal=0; slobbers=2; ulcer=3.
7. Activity
   NA
8. Appetite
   normal=0; decreased=1; anorexic (none)=3.
9. Other Animals were also weighed prior to inoculation and at necropsy. Average weight gains for each group were calculated for comparison. PRRS Enzyme Linked Immuno-Absorbent Assays (ELISA) and serum neutralization (SN) assays were performed following the exposures of the animals with test and control articles. Attempts to isolate PRRSV from serum samples were performed on MA-104 cells. Prior to and following vaccination, total white blood cell counts were determined using COULTER COUNTER MODEL Z1, Coulter Corp., Miami, Fla. At necropsy, the lungs of each animal were scored. Lung scoring was done by separating the lung into 7 sections and determining the percentage of lung involvement (the percentage of the lung area affected as shown by lesions or redness for each section and multiplying by the approximate area of the whole lung) that percentage of total lung area that the section encompasses. Parameters for lung scoring are as follows:

| | | |
|---|---|---|
| Left Apical Lobe % of involvement | × 0.10 | = __ |
| Left Cardiac Lobe % of involvement | × 0.10 | = __ |
| Left Diaphragmatic Lobe % of involvement | × 0.25 | = __ |
| Right Apical Lobe % of involvement | × 0.10 | = __ |
| Right Cardiac Lobe % of involvement | × 0.10 | = __ |
| Right Diaphragmatic Lobe % of involvement | × 0.25 | = __ |
| Intermediate Lobe of Right Lung % of involvement | × 0.10 | = __ |
| Total (Sum of all values in the far right column) | | = __ |

Results and Discussion

Each group of pigs was monitored for six days following vaccination. Clinical scores were low in all groups. Clinical score results are given in Table 1.

TABLE 1

Daily Clinical Scores

| Treatment | | Day −1 | Day 0 | Day1 | Day 2 | Day 3 | Day 4 | Day 5 | Day 6 | Average |
|---|---|---|---|---|---|---|---|---|---|---|
| | Group 1 Pig # | | | | | | | | | |
| JA-142 psg 200 | 545 | 0 | 0 | 2 | 0 | 0 | 0 | 0 | 0 | 0.25 |
| | 551 | 0 | 0 | 0 | 0 | 0 | 0 | 0 | 0 | 0 |
| | 561 | 0 | 0 | 0 | 0 | 0 | 0 | 0 | 0 | 0 |
| | 565 | 0 | 0 | 0 | 0 | 0 | 0 | 0 | 0 | 0 |
| | 806 | 0 | 0 | 0 | 0 | 0 | 0 | 0 | 0 | 0 |
| | Average | 0 | 0 | 0.4 | 0 | 0 | 0 | 0 | 0 | 0.05 |
| Saline | 550 | 0 | 0 | 0 | 0 | 0 | 0 | 0 | 0 | 0 |
| | 568 | 0 | 0 | 0 | 0 | 0 | 0 | 0 | 0 | 0 |
| | 801 | 0 | 0 | 0 | 0 | 0 | 0 | 0 | 0 | 0 |
| | Average | 0 | 0 | 0 | 0 | 0 | 0 | 0 | 0 | 0 |
| | Group 2 Pig # | | | | | | | | | |
| Backpassage 1 | 546 | 0 | 0 | 0 | 0 | 0 | 0 | 0 | 0 | 0 |
| | 553 | 0 | 0 | 0 | 0 | 0 | 0 | 0 | 0 | 0 |
| | 562 | 0 | 0 | 0 | 0 | 0 | 1 | 0 | 0 | 0.125 |
| | 572 | 0 | 0 | 0 | 0 | 0 | 0 | 0 | 0 | 0 |
| | 573 | 0 | 0 | 0 | 0 | 2 | 0 | 0 | 0 | 0.25 |
| | Average | 0 | 0 | 0 | 0 | 0.4 | 0.2 | 0 | 0 | 0.075 |
| Backpassage 1 | 556 | 0 | 0 | 0 | 0 | 0 | 0 | 0 | 0 | 0 |
| | 566 | 0 | 0 | 0 | 0 | 0 | 0 | 0 | 0 | 0 |
| | 802 | 0 | 0 | 0 | 0 | 0 | 0 | 0 | 0 | 0 |
| | Average | 0 | 0 | 0 | 0 | 0 | 0 | 0 | 0 | 0 |
| | Group 3 Pig # | | | | | | | | | |
| Backpassage 2 | 548 | 0 | 0 | 0 | 0 | 0 | 0 | 0 | 0 | 0 |
| | 567 | 0 | 0 | 0 | 0 | 0 | 0 | 0 | 0 | 0 |
| | 569 | 0 | 0 | 0 | 0 | 1 | 1 | 0 | 0 | 0.25 |
| | 574 | 0 | 0 | 0 | 0 | 0 | 0 | 0 | 0 | 0 |
| | 804 | 0 | 0 | 0 | 0 | 0 | 0 | 0 | 0 | 0 |
| | Average | 0 | 0 | 0 | 0 | 0.2 | 0.2 | 0 | 0 | 0.05 |
| Backpassage 2A | 547 | 0 | 0 | 0 | 0 | 0 | 0 | 0 | 0 | 0 |
| | 5564 | 0 | 0 | 0 | 0 | 0 | 0 | 0 | 0 | 0 |
| | 805 | 0 | 0 | 0 | 0 | 0 | 0 | 0 | 0 | 0 |
| | Average | 0 | 0 | 0 | 0 | 0 | 0 | 0 | 0 | 0 |
| | Group 4 Pig # | | | | | | | | | |
| Backpassage 3 | 549 | 0 | 0 | 0 | 0 | 0 | 0 | 0 | 0 | 0 |
| | 554 | 0 | 0 | 0 | 0 | 0 | 0 | 0 | 0 | 0 |
| | 563 | 0 | 0 | 0 | 0 | 0 | 0 | 0 | 0 | 0 |
| | 570 | 0 | 0 | 0 | 0 | 0 | 0 | 0 | 0 | 0 |
| | 803 | 0 | 0 | 0 | 0 | 0 | 0 | 0 | 0 | 0 |
| | Average | 0 | 0 | 0 | 0 | 0 | 0 | 0 | 0 | 0 |

TABLE 1-continued

Daily Clinical Scores

| Treatment | | Day −1 | Day 0 | Day1 | Day 2 | Day 3 | Day 4 | Day 5 | Day 6 | Average |
|---|---|---|---|---|---|---|---|---|---|---|
| Backpassage 3A | 560 | 0 | 0 | 0 | 0 | 0 | 0 | 0 | 0 | 0 |
| | 571 | 0 | 0 | 0 | 0 | 0 | 0 | 0 | 0 | 0 |
| | 575 | 0 | 0 | 0 | 0 | 0 | 0 | 0 | 0 | 0 |
| | Average | 0 | 0 | 0 | 0 | 0 | 0 | 0 | 0 | 0 |
| Group 5 Pig # | | | | | | | | | | |
| Backpassage 4 | 1 | 0 | 2 | 0 | 0 | 2 | 0 | 2 | 2 | 1 |
| | 2 | 0 | 0 | 0 | 0 | 0 | 0 | 0 | 0 | 0 |
| | 3 | 2 | 0 | 2 | 2 | 2 | 2 | 2 | 2 | 1.75 |
| | 4 | 0 | 0 | 0 | 0 | 0 | 0 | 0 | 0 | 0 |
| | 5 | 0 | 0 | 0 | 0 | 0 | 0 | 0 | 0 | 0 |
| | Average | 0.4 | 0.4 | 0.4 | 0.4 | 0.8 | 0.4 | 0.8 | 0.8 | 0.55 |
| Backpassage 4A | 6 | 0 | 0 | 0 | 0 | 0 | 0 | 0 | 0 | 0 |
| | 7 | 0 | 0 | 2 | 2 | 2 | 2 | 2 | 2 | 1.5 |
| | 8 | 0 | 0 | 0 | 0 | 0 | 0 | 0 | 0 | 0 |
| | Average | 0 | 0.08 | 0.48 | 0.48 | 0.56 | 0.48 | 0.56 | 0.56 | 0.4 |
| Group 6 Pig # | | | | | | | | | | |
| Backpassage 5 | 10 | 0 | 0 | 0 | 0 | 2 | 0 | 0 | 2 | 0.5 |
| | 12 | 0 | 0 | 0 | 2 | 2 | 0 | 0 | 2 | 0.75 |
| | 14 | 0 | 0 | 0 | 0 | 0 | 0 | 0 | 0 | 0 |
| | 15 | 2 | 2 | 2 | 0 | 0 | 0 | 0 | 2 | 1 |
| | 16 | 2 | 2 | 2 | 0 | 0 | 1 | 1 | 2 | 1.25 |
| | Average | 0.8 | 0.8 | 0.8 | 0.4 | 0.8 | 0.2 | 0.2 | 1.6 | 0.7 |
| Backpassage 5A | 9 | 0 | 0 | 0 | 0 | 0 | 0 | 0 | 0 | 0 |
| | 11 | 2 | 2 | 0 | 0 | 0 | 0 | 0 | 0 | 0.5 |
| | 13 | 0 | 0 | 0 | 0 | 0 | 0 | 0 | 0 | 0 |
| | Average | 0.666667 | 0.56 | 0.16 | 0.08 | 0.16 | 0.04 | 0.04 | 0.32 | 0.253333 |

There were no significant differences between groups for rectal temperatures or daily weight gains. All lung scores were negative.

Serologically, ELISA S/P ratios and SN titers were negative throughout each group's trial period. Virus isolation was attempted on all serum samples and lung lavages. By day 6, 60-100% of the serum samples from the groups given JA-142, passage 200, and subsequent back passes were positive. The groups given saline were negative. In the first three passes, virus was recovered in the lung lavages from only 20-40% of the pigs, but by the last three passes, the virus was recovered from 50-80% of the pigs.

Based on this data, JA-142 passage 200 did not revert to virulence when passed through pigs six times.

Example 3

Materials and Methods

This example demonstrated that the level of attenuation of safety of MSV, JA-142, passage 200 did not change significantly during six backpassages in the host animal. Evaluation of level of attenuation or safety was performed using the pregnant sow model and monitoring the effect on reproductive performance. This model is the most sensitive test system and does not rely upon subjective factors for virulence testing. This example consisted of four groups (A, B, C & D) having seven sows per group. Group A was inoculated intra-nasally with PRRS MSV, JA-142 passage 200. Group B was inoculated intra-nasally with JA-142, passage 200, Backpassage 6. Group C was inoculated intra-nasally with sterile diluent, to act as normal controls. Group D was inoculated intra-nasally with PRRSV JA-142, passage 4. The test articles (challenge with JA-142, passage 4) were given at about 93 days gestation. Body temperatures of the sows were monitored for the first seven days following vaccination. Blood samples were collected from the sows once a week and at time of farrowing. Blood samples were collected and weights were recorded from piglets at birth, 7, and 14 days of age. The health status of each animal was monitored daily for the duration of the study up to and following farrowing for 14 days. The farrowing performance was evaluated by observing the health status of the piglets born.

PRRS ELISA assays were performed following the exposures of the sows with the test article. PRRS ELISA assays were also performed on the piglet sera weekly following farrowing. Following exposure to the test article, attempts to isolate PRRSV from serum samples were performed on MA-104 cells. Rectal temperatures were measured periodically from 0 days post vaccination (DPV) to 7 DPV and the average temperature of each group was determined. Prior to and after inoculation, total white blood cell counts were determined as in Example 1. Clinical observations of the sows, as in Example 2, were made from −1 DPV through farrowing. Clinical observations of the piglets were made from farrowing until 14 days of age. Finally, at necropsy, the lungs of each piglet were scored for percent lung involvement.

Results

The ELISA results indicate that the animals used in this study were naive to PRRSV. Those animals that received virus inocula, groups A, B, and D, sero-converted at 14 days post treatment. Three sows of group B remained negative at 14 days post treatment. At the time of farrowing, the negative sows of group B tested positive for antibody to PRRSV.

The pigs' ELISA results indicated that the majority of the piglets born to sows of group A and group B were sampled after they had nursed. Those pigs that were negative at zero days post farrowing (0 DPF) tested positive at 7 DPF. All pigs born to sows of group C tested sero-negative throughout the study. Only a few pigs were tested from group D, since the majority were either stillborn or mummies. Half of those pigs that were tested were sero-positive. This indicated that the sero-negative pigs were sampled prior to nursing or they were not capable of nursing. All piglets born to sows of group D died before 7 DPF. Isolations of PRRSV from the sows of groups A and B were sporadic. Although the results of the ELISA test indicated that these sows were successfully inoculated with the viral test articles, many remained negative for virus isolation from serum.

The majority of pigs born to sows from groups A and B tested positive for virus isolation during the performance of the study. The litter born to one sow of group A never tested positive and the litter born to one sow of group B had only two of eight piglets test positive for virus isolation. No virus was recovered from the piglets born to sows from group C. Virus was recovered from the majority (71%) of piglets born from sows of group D.

Post treatment rectal temperatures were unremarkable. The groups that were treated with either MSV, backpassage 6 or sterile diluent experienced no measurements exceeding 101.7° F. Group D, treated with JA-142, passage 4, had four (out of seven) sows that experienced temperatures that exceeded 102° F. with one sow reaching 103.4° F. for one of the days. The weight gain performance of the piglets born to sows of groups A (treated with MSV) and B (treated with MSV, backpassage 6) was greater than that of the pigs born to the control sows of group C. The average weight gain for the 14 day observation period was 7.9 lbs. For group A, it was 7.7 lbs; for group B and group C it was 6.9 lbs. The difference in the weight gain was not related to the size of the litter remaining at 14 days. The average litter sizes at 14 days post farrowing (DPF) were 9 for group A, 7 for group B, and 10 for group C. No pig born to the sows of group D survived beyond 3 DPF.

The white blood cell (WBC) counts for the sows of groups A, B, and C remained relatively constant. The average percentages of the pre-challenge values were equal to or greater than 92% for the duration of the observation period. Three sows of group D experienced WBC counts that were lower than the expected normal range ($7-20 \times 10^6$/ml).

The post inoculation clinical scores were unremarkable for the sows of groups A and B. Several sows of group C were observed to experience clinical signs over a period of several days. The majority of the clinical symptoms observed were in the category of decreased appetite, respiratory symptoms, and depression. One sow of group C died on trial day 31 of chronic bacterial pneumonia. Six of the seven sows of group D were observed to have clinical signs, primarily of varying degrees in severity, of lost appetite, ranging from decreased to anorexic. Results of the clinical scoring for the sows are given in Table 2.

TABLE 2

Sow Clinical Scores

| Treatment | Sow# | -3 | -2 | -1 | 0 | 1 | 2 | 3 | 4 | 5 | 6 | 7 | 8 | 9 | 10 | 11 | 12 |
|---|---|---|---|---|---|---|---|---|---|---|---|---|---|---|---|---|---|
| Group A | 98 | 0 | 0 | 0 | 0 | 0 | 0 | 0 | 0 | 0 | 0 | 0 | 0 | 0 | 0 | 0 | 0 |
| JA-142 MSV | 133 | 0 | 0 | 0 | 0 | 0 | 0 | 0 | 0 | 0 | 0 | 0 | 0 | 0 | 0 | 0 | 0 |
| Passage 200 | 147 | 0 | 0 | 0 | 0 | 0 | 0 | 0 | 0 | 0 | 0 | 0 | 0 | 0 | 0 | 0 | 0 |
| | 178 | 0 | 0 | 0 | 0 | 0 | 0 | 0 | 0 | 0 | 0 | 0 | 0 | 0 | 0 | 0 | 0 |
| | 215 | 0 | 0 | 0 | 0 | 0 | 0 | 0 | 0 | 0 | 0 | 0 | 0 | 0 | 0 | 0 | 0 |
| | 233 | 0 | 0 | 0 | 0 | 0 | 0 | 0 | 0 | 0 | 0 | 0 | 0 | 0 | 0 | 0 | 0 |
| | 243 | 0 | 0 | 0 | 0 | 0 | 0 | 0 | 0 | 0 | 0 | 0 | 0 | 0 | 0 | 0 | 0 |
| | Avg. | 0 | 0 | 0 | 0 | 0 | 0 | 0 | 0 | 0 | 0 | 0 | 0 | 0 | 0 | 0 | 0 |

| | | 13 | 14 | 15 | 16 | 17 | 18 | 19 | 20 | 21 | 22 | 23 | 24 | 25 | 26 | 27 | 28 |
|---|---|---|---|---|---|---|---|---|---|---|---|---|---|---|---|---|---|
| Group A | 98 | 0 | 0 | 0 | 0 | 0 | 0 | 0 | 0 | 0 | 0 | 0 | 0 | 0 | 0 | 0 | 0 |
| JA-142 MSV | 133 | 0 | 0 | 0 | 0 | 0 | 0 | 0 | 0 | 0 | 0 | 0 | 0 | 0 | 0 | 0 | 0 |
| Passage 200 | 147 | 0 | 0 | 0 | 0 | 0 | 0 | 0 | 0 | 0 | 0 | 0 | 0 | 0 | 0 | 0 | 0 |
| | 178 | 0 | 2 | 0 | 0 | 0 | 0 | 0 | 0 | 0 | 0 | 0 | 0 | 0 | 0 | 0 | 0 |
| | 215 | 0 | 0 | 0 | 0 | 0 | 0 | 0 | 0 | 0 | 0 | 0 | 0 | 0 | 0 | 0 | 0 |
| | 233 | 0 | 0 | 0 | 0 | 0 | 0 | 0 | 0 | 0 | 0 | 0 | 0 | 0 | 0 | 0 | 0 |
| | 243 | 0 | 2 | 0 | 0 | 0 | 0 | 0 | 0 | 0 | 0 | 0 | 0 | 0 | 0 | 0 | 0 |
| | Avg. | 0 | 0.6 | 0 | 0 | 0 | 0 | 0 | 0 | 0 | 0 | 0 | 0 | 0 | 0 | 0 | 0 |

| | | 29 | 30 | 31 | 32 | 33 | 34 | 35 | 36 | 37 | 38 | 39 | 40 | 41 | 42 | 43 | 44 |
|---|---|---|---|---|---|---|---|---|---|---|---|---|---|---|---|---|---|
| Group A | 98 | 0 | 0 | 0 | 0 | 0 | 0 | 0 | 0 | 0 | 0 | 0 | 0 | 0 | 0 | 0 | 0 |
| JA-142 MSV | 133 | 0 | 0 | 0 | 0 | 0 | 0 | 0 | 0 | 0 | 0 | 0 | 0 | 0 | 0 | 0 | 0 |
| Passage 200 | 147 | 0 | 0 | 0 | 0 | 0 | 0 | 0 | 0 | 0 | 0 | 0 | 0 | 0 | 0 | 0 | 0 |
| | 178 | 0 | 0 | 0 | 0 | 0 | 0 | 0 | 0 | 0 | 0 | 0 | 0 | 0 | 0 | 0 | 0 |
| | 215 | 0 | 0 | 0 | 0 | 0 | 0 | 0 | 0 | 0 | 0 | 0 | 0 | 0 | 0 | 0 | 0 |
| | 233 | 0 | 0 | 0 | 0 | 0 | 0 | 0 | 0 | 0 | 0 | 0 | 0 | 0 | 0 | 0 | 0 |
| | 243 | 0 | 0 | 0 | 0 | 0 | 0 | 0 | 0 | 0 | 0 | 0 | 0 | 0 | 0 | 0 | 0 |
| | Avg. | 0 | 0 | 0 | 0 | 0 | 0 | 0 | 0 | 0 | 0 | 0 | 0 | 0 | 0 | 0 | 0 |

| Treatment | Sow# | -3 | -2 | -1 | 0 | 1 | 2 | 3 | 4 | 5 | 6 | 7 | 8 | 9 | 10 | 11 | 12 |
|---|---|---|---|---|---|---|---|---|---|---|---|---|---|---|---|---|---|
| Group B | 49 | 0 | 0 | 0 | 0 | 0 | 0 | 0 | 0 | 0 | 0 | 0 | 0 | 0 | 0 | 0 | 0 |
| Backpassage6 | 100 | 0 | 0 | 0 | 0 | 0 | 0 | 0 | 0 | 0 | 0 | 0 | 0 | 0 | 0 | 0 | 0 |
| | 135 | 0 | 0 | 0 | 0 | 0 | 0 | 0 | 0 | 0 | 0 | 0 | 0 | 0 | 0 | 0 | 0 |
| | 149 | 0 | 0 | 0 | 0 | 0 | 0 | 0 | 0 | 0 | 0 | 0 | 0 | 1 | 1 | 1 | 1 |
| | 209 | 0 | 0 | 0 | 0 | 0 | 0 | 0 | 0 | 0 | 0 | 0 | 0 | 0 | 0 | 0 | 0 |
| | 212 | 0 | 0 | 0 | 0 | 0 | 0 | 0 | 0 | 0 | 0 | 0 | 0 | 0 | 0 | 0 | 0 |
| | 226 | 0 | 0 | 0 | 0 | 0 | 0 | 0 | 0 | 0 | 0 | 0 | 0 | 0 | 0 | 0 | 0 |
| | Avg. | 0 | 0 | 0 | 0 | 0 | 0 | 0 | 0 | 0 | 0 | 0 | 0 | 0.1 | 0.1 | 0.1 | 0.1 |

TABLE 2-continued

Sow Clinical Scores

|  |  | 13 | 14 | 15 | 16 | 17 | 18 | 19 | 20 | 21 | 22 | 23 | 24 | 25 | 26 | 27 | 28 |
|---|---|---|---|---|---|---|---|---|---|---|---|---|---|---|---|---|---|
| Group B | 49 | 0 | 0 | 0 | 0 | 0 | 0 | 0 | 0 | 0 | 0 | 0 | 0 | 0 | 0 | 0 | 0 |
| Backpassage6 | 100 | 0 | 0 | 0 | 0 | 0 | 0 | 0 | 0 | 0 | 0 | 0 | 0 | 0 | 0 | 0 | 0 |
|  | 135 | 0 | 0 | 0 | 0 | 0 | 0 | 0 | 0 | 0 | 0 | 0 | 0 | 0 | 0 | 0 | 0 |
|  | 149 | 0 | 0 | 0 | 0 | 0 | 0 | 0 | 1 | 1 | 0 | 0 | 0 | 0 | 0 | 0 | 0 |
|  | 209 | 0 | 0 | 0 | 0 | 0 | 0 | 0 | 0 | 0 | 0 | 0 | 0 | 0 | 0 | 0 | 0 |
|  | 212 | 0 | 0 | 0 | 0 | 0 | 0 | 0 | 0 | 0 | 0 | 0 | 0 | 0 | 0 | 0 | 0 |
|  | 226 | 0 | 0 | 0 | 0 | 0 | 0 | 0 | 0 | 0 | 0 | 0 | 0 | 0 | 0 | 0 | 0 |
|  | Avg. | 0 | 0 | 0 | 0 | 0 | 0 | 0 | 0.1 | 0.1 | 0 | 0 | 0 | 0 | 0 | 0 | 0 |

|  |  | 29 | 30 | 31 | 32 | 33 | 34 | 35 | 36 | 37 | 38 | 39 | 40 | 41 | 42 | 43 | 44 |
|---|---|---|---|---|---|---|---|---|---|---|---|---|---|---|---|---|---|
| Group B | 49 | 0 | 0 | 0 | 0 | 0 | 0 | 0 | 0 | 0 | 0 | 0 | 0 | 0 | 0 | 0 | 0 |
| Backpassage6 | 100 | 0 | 0 | 0 | 0 | 0 | 0 | 0 | 0 | 0 | 0 | 0 | 0 | 0 | 0 | 0 | 0 |
|  | 135 | 0 | 0 | 0 | 0 | 0 | 0 | 0 | 0 | 0 | 0 | 0 | 0 | 0 | 0 | 0 | 0 |
|  | 149 | 0 | 0 | 0 | 0 | 0 | 0 | 0 | 0 | 0 | 0 | 2 | 2 | 2 | 2 | 2 | 2 |
|  | 209 | 0 | 0 | 0 | 0 | 0 | 0 | 0 | 0 | 0 | 0 | 0 | 0 | 0 | 0 | 0 | 0 |
|  | 212 | 0 | 0 | 0 | 0 | 0 | 0 | 0 | 0 | 0 | 0 | 0 | 0 | 0 | 0 | 0 | 0 |
|  | 226 | 0 | 0 | 0 | 0 | 0 | 0 | 0 | 0 | 0 | 0 | 0 | 0 | 0 | 0 | 0 | 0 |
|  | Avg. | 0 | 0 | 0 | 0 | 0 | 0 | 0 | 0 | 0 | 0 | 0.3 | 0.3 | 0.3 | 0.3 | 0.3 | 0.3 |

| Treatment | Sow# | −3 | −2 | −1 | 0 | 1 | 2 | 3 | 4 | 5 | 6 | 7 | 8 | 9 | 10 | 11 | 12 |
|---|---|---|---|---|---|---|---|---|---|---|---|---|---|---|---|---|---|
| Group C | 58 | 0 | 0 | 0 | 0 | 0 | 0 | 0 | 0 | 0 | 0 | 0 | 0 | 0 | 0 | 0 | 0 |
| Sterile | 113 | 0 | 0 | 0 | 0 | 0 | 0 | 0 | 0 | 0 | 0 | 1 | 3 | 3 | 5 | 3 | 3 |
| Diluent | 117 | 0 | 0 | 0 | 0 | 0 | 0 | 0 | 0 | 0 | 0 | 0 | 0 | 0 | 0 | 1 | 1 |
|  | 144 | 0 | 0 | 0 | 0 | 0 | 0 | 0 | 0 | 0 | 0 | 0 | 0 | 0 | 0 | 0 | 0 |
|  | 156 | 0 | 0 | 0 | 0 | 0 | 0 | 0 | 0 | 0 | 0 | 0 | 0 | 0 | 0 | 0 | 0 |
|  | 166 | 0 | 0 | 0 | 0 | 0 | 0 | 0 | 0 | 0 | 0 | 0 | 0 | 0 | 0 | 0 | 0 |
|  | Avg. | 0 | 0 | 0 | 0 | 0 | 0 | 0 | 0 | 0 | 0 | 0.2 | 0.5 | 0.5 | 0.8 | 0.7 | 0.7 |

|  |  | 13 | 14 | 15 | 16 | 17 | 18 | 19 | 20 | 21 | 22 | 23 | 24 | 25 | 26 | 27 | 28 |
|---|---|---|---|---|---|---|---|---|---|---|---|---|---|---|---|---|---|
| Group C | 58 | 0 | 0 | 0 | 0 | 0 | 0 | 0 | 0 | 0 | 0 | 0 | 0 | 0 | 0 | 0 | 0 |
| Sterile | 113 | 3 | 3 | 3 | 3 | 3 | 3 | 4 | 4 | 4 | 4 | 6 | 6 | 2 | 4 | 2 | 2 |
| Diluent | 117 | 0 | 0 | 0 | 0 | 0 | 0 | 1 | 5 | 5 | 5 | 5 | 5 | 2 | 4 | 1 | 1 |
|  | 144 | 0 | 0 | 0 | 0 | 0 | 0 | 0 | 0 | 0 | 0 | 0 | 0 | 0 | 0 | 0 | 0 |
|  | 156 | 2 | 0 | 0 | 0 | 0 | 0 | 0 | 0 | 0 | 0 | 0 | 0 | 0 | 0 | 0 | 0 |
|  | 166 | 0 | 0 | 0 | 0 | 0 | 0 | 0 | 0 | 0 | 0 | 0 | 0 | 0 | 0 | 0 | 0 |
|  | Avg. | 0.8 | 0.5 | 0.5 | 0.5 | 0.5 | 0.5 | 0.8 | 1.5 | 1.5 | 1.5 | 1.8 | 1.8 | 0.7 | 1.3 | 0.5 | 0.5 |

|  |  | 29 | 30 | 31 | 32 | 33 | 34 | 35 | 36 | 37 | 38 | 39 | 40 | 41 | 42 | 43 | 44 |
|---|---|---|---|---|---|---|---|---|---|---|---|---|---|---|---|---|---|
| Group C | 58 | 0 | 0 | 0 | 0 | 0 | 0 | 0 | 0 | 0 | 0 | 0 | 0 | 0 | 0 | 0 | 0 |
| Sterile | 113 | 2 | 2 | 30 |  |  |  |  |  |  |  |  |  |  |  |  |  |
| Diluent | 117 | 2 | 2 | 0 | 0 | 0 | 0 | 0 | 0 | 0 | 0 | 0 | 0 | 0 | 0 | 0 | 0 |
|  | 144 | 0 | 0 | 0 | 0 | 0 | 0 | 0 | 0 | 0 | 0 | 1 | 1 | 1 | 1 | 1 | 1 |
|  | 156 | 0 | 0 | 0 | 0 | 0 | 0 | 0 | 0 | 0 | 0 | 0 | 0 | 0 | 0 | 0 | 0 |
|  | 166 | 0 | 0 | 0 | 0 | 0 | 0 | 0 | 0 | 0 | 0 | 0 | 0 | 0 | 0 | 0 | 0 |
|  | Avg. | 0.7 | 0.7 | 6 | 0 | 0 | 0 | 0 | 0 | 0 | 0 | 0.2 | 0.2 | 0.2 | 0.2 | 0.2 | 0.2 |

| Treatment | Sow# | −3 | −2 | −1 | 0 | 1 | 2 | 3 | 4 | 5 | 6 | 7 | 8 | 9 | 10 | 11 | 12 |
|---|---|---|---|---|---|---|---|---|---|---|---|---|---|---|---|---|---|
| Group D | 2 | 0 | 0 | 0 | 0 | 0 | 0 | 0 | 0 | 0 | 1 | 1 | 1 | 1 | 1 | 1 | 1 |
| JA-142 | 106 | 0 | 0 | 0 | 0 | 0 | 0 | 0 | 0 | 0 | 0 | 1 | 1 | 1 | 1 | 1 | 1 |
| Pass 4 | 159 | 0 | 0 | 0 | 0 | 0 | 0 | 0 | 0 | 0 | 3 | 1 | 1 | 1 | 1 | 1 | 1 |
|  | 190 | 0 | 0 | 0 | 0 | 0 | 0 | 0 | 0 | 0 | 0 | 0 | 0 | 1 | 1 | 1 | 1 |
|  | 206 | 0 | 0 | 0 | 0 | 0 | 0 | 0 | 0 | 0 | 0 | 1 | 1 | 0 | 0 | 0 | 0 |
|  | 232 | 0 | 0 | 0 | 0 | 0 | 0 | 0 | 0 | 0 | 0 | 0 | 0 | 0 | 0 | 0 | 0 |
|  | 234 | 0 | 0 | 0 | 0 | 0 | 0 | 0 | 0 | 0 | 0 | 0 | 0 | 0 | 1 | 1 | 1 |
|  | Avg. | 0 | 0 | 0 | 0 | 0 | 0 | 0 | 0 | 0 | 0.6 | 0.6 | 0.6 | 0.6 | 0.7 | 0.7 | 0.7 |

|  |  | 13 | 14 | 15 | 16 | 17 | 18 | 19 | 20 | 21 | 22 | 23 | 24 | 25 | 26 | 27 | 28 |
|---|---|---|---|---|---|---|---|---|---|---|---|---|---|---|---|---|---|
| Group D | 2 | 1 | 1 | 3 | 3 | 1 | 0 | 0 | 0 | 0 | 0 | 0 | 0 | 0 | 0 | 0 | 0 |
| JA-142 | 106 | 0 | 0 | 0 | 0 | 0 | 0 | 0 | 0 | 0 | 0 | 0 | 0 | 0 | 0 | 0 | 0 |
| Pass 4 | 159 | 1 | 1 | 1 | 1 | 3 | 4 | 2 | 3 | 3 | 3 | 2 | 0 | 0 | 2 | 0 | 0 |
|  | 190 | 1 | 2 | 0 | 0 | 0 | 0 | 0 | 0 | 0 | 0 | 0 | 0 | 0 | 0 | 0 | 0 |
|  | 206 | 0 | 0 | 0 | 0 | 0 | 0 | 0 | 0 | 0 | 0 | 0 | 0 | 0 | 0 | 0 | 0 |
|  | 232 | 0 | 0 | 0 | 0 | 0 | 0 | 0 | 0 | 0 | 0 | 0 | 0 | 0 | 0 | 0 | 0 |
|  | 234 | 0 | 2 | 0 | 0 | 0 | 0 | 0 | 0 | 0 | 0 | 0 | 0 | 0 | 0 | 0 | 0 |
|  | Avg. | 0.4 | 0.3 | 0.6 | 0.6 | 0.6 | 0.6 | 0.3 | 0.4 | 0.4 | 0.4 | 0.3 | 0 | 0 | 0.3 | 0 | 0 |

TABLE 2-continued

Sow Clinical Scores

|  |  | 29 | 30 | 31 | 32 | 33 | 34 | 35 | 36 | 37 | 38 |
|---|---|---|---|---|---|---|---|---|---|---|---|
| Group D | 2 | 0 | 0 | 0 | 1 | 1 | 1 | 3 | 3 | 1 | 1 |
| JA-142 | 106 | 0 | 0 | 0 | 0 | 0 | 0 | 0 | 0 | 0 | 0 |
| Pass 4 | 159 | 0 | 0 | 0 | 0 | 0 | 0 | 0 | 0 | 0 | 0 |
|  | 190 | 0 | 0 | 0 | 0 | 0 | 0 | 0 | 0 | 0 | 0 |
|  | 206 | 0 | 0 | 0 | 0 | 0 | 0 | 0 | 0 | 0 | 0 |
|  | 232 | 0 | 0 | 0 | 0 | 0 | 0 | 0 | 0 | 0 | 0 |
|  | 234 | 0 | 0 | 0 | 0 | 0 | 0 | 0 | 0 | 0 | 0 |
|  | Avg. | 0 | 0 | 0 | 0.1 | 0.1 | 0.1 | 0.4 | 0.4 | 0.1 | 0.1 |

Clinical observations of the piglets fell into two major categories, death and reduced appetite. There were no significant differences between groups A, B and C in the area of average deaths per litter (DPL). Group A had an average of 1.3 DPL, group B had an average of 2.4 DPL, group C had an average of 2.0 DPL, and no pigs from group D survived beyond three days post farrowing. Clinical scores for the piglets are given in Table 3.

TABLE 3

| Treatment | Sow# | Pig# | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|---|
| Group A | 98 | 813 | 0 | 0 | 1 | 30 |  |  |  |  |  |  |  |  |  |  |
| JA-142 |  | 814 | 0 | 0 | 0 | 0 | 0 | 0 | 0 | 0 | 0 | 0 | 0 | 0 | 0 | 0 |
| Pass 200 |  | 815 | 0 | 0 | 0 | 0 | 0 | 0 | 0 | 0 | 0 | 0 | 0 | 0 | 0 | 0 |
|  |  | 816 | 0 | 0 | 0 | 0 | 0 | 0 | 0 | 0 | 0 | 0 | 0 | 0 | 0 | 0 |
|  |  | 817 | 1 | 0 | 1 | 0 | 0 | 0 | 0 | 0 | 0 | 0 | 0 | 0 | 0 | 0 |
|  |  | 818 | 0 | 0 | 0 | 0 | 0 | 0 | 0 | 0 | 0 | 0 | 0 | 0 | 0 | 0 |
|  |  | 819 | 0 | 0 | 0 | 0 | 0 | 0 | 0 | 0 | 0 | 0 | 0 | 0 | 0 | 0 |
|  |  | 820 | 0 | 0 | 0 | 0 | 0 | 0 | 0 | 0 | 0 | 0 | 0 | 0 | 0 | 0 |
|  |  | 821 | 1 | 0 | 0 | 0 | 0 | 0 | 0 | 0 | 0 | 0 | 0 | 0 | 0 | 0 |
|  |  | 822 | 1 | 30 |  |  |  |  |  |  |  |  |  |  |  |  |
|  |  | Avg. | 0.3 | 3 | 0.2 | 3.3 | 0 | 0 | 0 | 0 | 0 | 0 | 0 | 0 | 0 | 0 |
|  | 133 | 720 | 30 |  |  |  |  |  |  |  |  |  |  |  |  |  |
|  |  | 721 | 0 | 1 | 0 | 0 | 0 | 0 | 0 | 0 | 0 | 0 | 0 | 0 | 0 | 0 |
|  |  | 722 | 0 | 0 | 0 | 1 | 0 | 0 | 0 | 0 | 0 | 0 | 0 | 0 | 0 | 0 |
|  |  | 723 | 0 | 0 | 0 | 0 | 0 | 0 | 0 | 0 | 0 | 0 | 0 | 0 | 0 | 0 |
|  |  | 724 | 0 | 1 | 0 | 0 | 0 | 1 | 0 | 0 | 0 | 0 | 0 | 0 | 0 | 0 |
|  |  | 725 | 0 | 0 | 0 | 0 | 0 | 0 | 0 | 0 | 0 | 0 | 0 | 0 | 0 | 0 |
|  |  | 798 | 0 | 0 | 0 | 0 | 0 | 0 | 0 | 0 | 0 | 0 | 0 | 0 | 0 | 0 |
|  |  | 799 | 30 |  |  |  |  |  |  |  |  |  |  |  |  |  |
|  |  | 800 | 0 | 0 | 0 | 0 | 0 | 0 | 0 | 0 | 0 | 0 | 0 | 0 | 0 | 0 |
|  |  | 807 | 0 | 0 | 0 | 0 | 0 | 0 | 0 | 0 | 0 | 0 | 1 | 0 | 0 | 0 |
|  |  | 809 | 0 | 0 | 0 | 0 | 0 | 0 | 0 | 0 | 0 | 0 | 0 | 0 | 0 | 0 |
|  |  | 810 | 0 | 0 | 0 | 0 | 0 | 0 | 0 | 0 | 0 | 0 | 0 | 0 | 0 | 0 |
|  |  | 812 | 0 | 0 | 0 | 0 | 0 | 0 | 0 | 0 | 0 | 0 | 0 | 0 | 0 | 0 |
|  |  | Avg. | 4.6 | 0.2 | 0 | 0.1 | 0 | 0.1 | 0 | 0 | 0 | 0 | 0 | 0.1 | 0 | 0 |
|  | 147 | 823 | 0 | 0 | 0 | 0 | 0 | 0 | 0 | 0 | 0 | 0 | 0 | 0 | 0 | 0 |
|  |  | 824 | 0 | 0 | 0 | 0 | 0 | 0 | 0 | 3 | 1 | 1 | 1 | 1 | 1 | 1 |
|  |  | 825 | 0 | 0 | 0 | 0 | 0 | 0 | 0 | 0 | 0 | 0 | 0 | 0 | 0 | 0 |
|  |  | 845 | 0 | 0 | 0 | 0 | 0 | 0 | 0 | 0 | 0 | 0 | 0 | 0 | 0 | 0 |
|  |  | 846 | 0 | 0 | 0 | 0 | 0 | 0 | 0 | 0 | 0 | 0 | 0 | 0 | 0 | 0 |
|  |  | 847 | 0 | 0 | 0 | 0 | 0 | 0 | 0 | 0 | 0 | 0 | 0 | 0 | 0 | 0 |
|  |  | 848 | 0 | 0 | 0 | 0 | 0 | 0 | 1 | 0 | 0 | 0 | 0 | 0 | 0 | 0 |
|  |  | 849 | 0 | 0 | 0 | 0 | 0 | 0 | 0 | 0 | 0 | 0 | 0 | 0 | 0 | 2 |
|  |  | 850 | 30 |  |  |  |  |  |  |  |  |  |  |  |  |  |
|  |  | 976 | 0 | 0 | 0 | 0 | 0 | 0 | 0 | 0 | 0 | 0 | 0 | 0 | 0 | 0 |
|  |  | 977 | 0 | 0 | 0 | 0 | 1 | 1 | 3 | 30 |  |  |  |  |  |  |
|  |  | 978 | 30 |  |  |  |  |  |  |  |  |  |  |  |  |  |
|  |  | Avg. | 5 | 0 | 0 | 0 | 0.1 | 0.1 | 0.4 | 3.3 | 0.1 | 0.1 | 0.1 | 0.1 | 0.1 | 0.3 |
|  | 178 | 486 | 30 |  |  |  |  |  |  |  |  |  |  |  |  |  |
|  |  | 487 | 0 | 0 | 0 | 0 | 0 | 0 | 0 | 0 | 0 | 0 | 1 | 0 | 0 | 0 |
|  |  | 488 | 0 | 0 | 0 | 0 | 0 | 0 | 0 | 0 | 0 | 0 | 0 | 0 | 0 | 0 |
|  |  | 489 | 0 | 0 | 0 | 0 | 0 | 0 | 0 | 0 | 0 | 0 | 0 | 0 | 0 | 0 |
|  |  | 490 | 0 | 0 | 0 | 0 | 0 | 0 | 0 | 0 | 0 | 0 | 0 | 0 | 0 | 0 |
|  |  | 491 | 0 | 0 | 0 | 0 | 0 | 0 | 0 | 0 | 0 | 0 | 0 | 0 | 0 | 0 |
|  |  | 492 | 0 | 0 | 0 | 0 | 0 | 0 | 0 | 0 | 0 | 0 | 0 | 0 | 0 | 0 |
|  |  | 493 | 0 | 0 | 0 | 0 | 0 | 0 | 0 | 0 | 0 | 0 | 0 | 0 | 0 | 0 |
|  |  | 494 | 0 | 1 | 0 | 0 | 0 | 0 | 0 | 0 | 0 | 0 | 0 | 0 | 0 | 0 |
|  |  | Avg. | 3.3 | 0.1 | 0 | 0 | 0 | 0 | 0 | 0 | 0 | 0 | 0.1 | 0 | 0 | 0 |
| Group A | 215 | 495 | 0 | 0 | 0 | 0 | 0 | 0 | 0 | 0 | 0 | 0 | 0 | 0 | 0 | 0 |
| JA-142 |  | 496 | 0 | 0 | 0 | 0 | 0 | 0 | 0 | 0 | 0 | 0 | 0 | 0 | 0 | 0 |
| Pass 200 |  | 497 | 0 | 0 | 0 | 0 | 0 | 0 | 0 | 0 | 0 | 0 | 0 | 0 | 0 | 0 |
|  |  | 498 | 0 | 0 | 0 | 0 | 0 | 0 | 0 | 0 | 0 | 0 | 0 | 0 | 0 | 0 |
|  |  | 499 | 0 | 0 | 0 | 0 | 0 | 0 | 0 | 0 | 0 | 0 | 0 | 0 | 0 | 0 |

TABLE 3-continued

| Treatment | Sow# | Pig# | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|---|
| | | 500 | 0 | 0 | 0 | 0 | 0 | 0 | 0 | 0 | 0 | 0 | 0 | 0 | 0 | 0 |
| | | 808 | 0 | 0 | 0 | 0 | 0 | 0 | 0 | 0 | 0 | 0 | 0 | 0 | 0 | 0 |
| | | Avg. | 0 | 0 | 0 | 0 | 0 | 0 | 0 | 0 | 0 | 0 | 0 | 0 | 0 | 0 |
| | 233 | 476 | 0 | 0 | 0 | 0 | 0 | 0 | 0 | 0 | 0 | 0 | 0 | 0 | 0 | 0 |
| | | 477 | 0 | 0 | 0 | 0 | 0 | 0 | 0 | 0 | 0 | 0 | 0 | 0 | 0 | 0 |
| | | 478 | 0 | 0 | 0 | 0 | 0 | 0 | 0 | 0 | 0 | 0 | 0 | 0 | 0 | 0 |
| | | 478 | 0 | 0 | 0 | 0 | 0 | 0 | 0 | 0 | 0 | 0 | 0 | 0 | 0 | 0 |
| | | 480 | 0 | 0 | 0 | 0 | 0 | 0 | 0 | 0 | 0 | 0 | 0 | 0 | 0 | 0 |
| | | 481 | 0 | 0 | 0 | 0 | 0 | 0 | 0 | 0 | 0 | 0 | 0 | 0 | 0 | 0 |
| | | 482 | 0 | 0 | 0 | 0 | 0 | 0 | 0 | 0 | 0 | 0 | 0 | 0 | 0 | 0 |
| | | 483 | 0 | 0 | 0 | 0 | 0 | 0 | 0 | 0 | 0 | 0 | 0 | 0 | 0 | 0 |
| | | 484 | 0 | 0 | 0 | 0 | 0 | 0 | 0 | 0 | 0 | 0 | 0 | 0 | 0 | 0 |
| | | 485 | 0 | 0 | 0 | 0 | 0 | 0 | 0 | 0 | 0 | 0 | 0 | 0 | 0 | 0 |
| | | Avg. | 0 | 0 | 0 | 0 | 0 | 0 | 0 | 0 | 0 | 0 | 0 | 0 | 0 | 0 |
| | 243 | 707 | 0 | 0 | 0 | 0 | 0 | 0 | 0 | 0 | 0 | 0 | 0 | 0 | 0 | 0 |
| | | 708 | 0 | 0 | 0 | 0 | 0 | 0 | 0 | 0 | 0 | 0 | 0 | 0 | 0 | 0 |
| | | 709 | 0 | 0 | 0 | 0 | 0 | 0 | 0 | 0 | 0 | 0 | 0 | 0 | 0 | 0 |
| | | 710 | 0 | 0 | 0 | 0 | 0 | 0 | 0 | 0 | 0 | 0 | 0 | 0 | 0 | 0 |
| | | 711 | 0 | 0 | 0 | 0 | 0 | 0 | 0 | 0 | 0 | 0 | 0 | 0 | 0 | 0 |
| | | 712 | 0 | 0 | 0 | 0 | 0 | 0 | 0 | 0 | 0 | 0 | 0 | 0 | 0 | 0 |
| | | 713 | 0 | 0 | 0 | 0 | 0 | 0 | 0 | 0 | 0 | 1 | 30 | | | |
| | | 714 | 0 | 0 | 0 | 0 | 0 | 0 | 0 | 0 | 0 | 0 | 0 | 0 | 0 | 0 |
| | | 715 | 0 | 0 | 0 | 0 | 0 | 0 | 0 | 0 | 0 | 0 | 0 | 0 | 0 | 0 |
| | | 716 | 0 | 0 | 0 | 0 | 0 | 0 | 0 | 0 | 0 | 0 | 0 | 0 | 0 | 0 |
| | | 717 | 0 | 0 | 0 | 0 | 0 | 0 | 0 | 0 | 0 | 0 | 0 | 1 | 0 | 0 |
| | | 718 | 0 | 0 | 0 | 0 | 0 | 0 | 0 | 0 | 0 | 0 | 0 | 1 | 0 | 0 |
| | | 719 | 0 | 0 | 0 | 0 | 0 | 0 | 0 | 0 | 0 | 0 | 0 | 0 | 0 | 0 |
| | | Avg. | 0 | 0 | 0 | 0 | 0 | 0 | 0 | 0 | 0 | 0.1 | 2.3 | 0.2 | 0 | 0 |
| Group B | | | | | | | | | | | | | | | | |
| Backpassage 6 | 49 | 430 | 0 | 0 | 0 | 0 | 0 | 0 | 0 | 0 | 0 | 0 | 0 | 0 | 0 | 0 |
| | | 431 | 0 | 0 | 0 | 0 | 0 | 0 | 0 | 0 | 0 | 0 | 0 | 0 | 0 | 0 |
| | | 432 | 0 | 0 | 0 | 0 | 0 | 0 | 0 | 0 | 0 | 0 | 0 | 0 | 0 | 0 |
| | | 433 | 0 | 0 | 0 | 0 | 0 | 0 | 0 | 0 | 0 | 0 | 0 | 0 | 0 | 0 |
| | | 434 | 0 | 0 | 0 | 0 | 0 | 0 | 0 | 0 | 0 | 0 | 0 | 0 | 0 | 0 |
| | | 435 | 0 | 0 | 0 | 0 | 0 | 0 | 0 | 0 | 0 | 0 | 0 | 0 | 0 | 0 |
| | | 436 | 0 | 0 | 0 | 0 | 0 | 0 | 0 | 0 | 0 | 0 | 0 | 0 | 0 | 0 |
| | | 437 | 0 | 0 | 0 | 0 | 0 | 0 | 0 | 0 | 0 | 0 | 0 | 0 | 0 | 0 |
| | | 438 | 30 | 0 | 0 | 0 | 0 | 0 | 0 | 0 | 0 | 0 | 0 | 0 | 0 | 0 |
| | | Avg. | 3.3 | 0 | 0 | 0 | 0 | 0 | 0 | 0 | 0 | 0 | 0 | 0 | 0 | 0 |
| | 100 | 459 | 0 | 0 | 0 | 0 | 0 | 0 | 0 | 0 | 0 | 0 | 0 | 0 | 0 | 0 |
| | | 460 | 0 | 0 | 0 | 0 | 0 | 0 | 0 | 0 | 0 | 0 | 0 | 0 | 0 | 0 |
| | | 461 | 0 | 0 | 0 | 0 | 0 | 0 | 1 | 1 | 1 | 0 | 0 | 0 | 0 | 0 |
| | | 462 | 0 | 0 | 0 | 0 | 1 | 1 | 1 | 1 | 1 | 1 | 1 | 1 | 1 | 1 |
| | | 463 | 0 | 0 | 0 | 0 | 0 | 0 | 0 | 0 | 0 | 0 | 0 | 0 | 0 | 0 |
| | | 464 | 0 | 0 | 1 | 1 | 1 | 1 | 30 | | | | | | | |
| | | 465 | 0 | 30 | | | | | | | | | | | | |
| | | Avg. | 0 | 4.3 | 0.2 | 0.2 | 0.3 | 0.3 | 5.3 | 0.4 | 0.4 | 0.2 | 0.2 | 0.2 | 0.2 | 0.2 |
| | 135 | 439 | 0 | 0 | 0 | 0 | 0 | 0 | 0 | 30 | | | | | | |
| | | 440 | 0 | 0 | 0 | 0 | 0 | 0 | 0 | 0 | 0 | 0 | 0 | 0 | 0 | 0 |
| | | 441 | 0 | 0 | 0 | 0 | 0 | 0 | 0 | 0 | 0 | 0 | 0 | 0 | 0 | 0 |
| | | 442 | 0 | 0 | 0 | 1 | 1 | 1 | 1 | 1 | 1 | 1 | 3 | 3 | 3 | 30 |
| | | 443 | 0 | 0 | 0 | 0 | 0 | 0 | 0 | 0 | 0 | 0 | 0 | 0 | 0 | 0 |
| | | 444 | 0 | 0 | 0 | 0 | 0 | 0 | 1 | 1 | 0 | 0 | 0 | 0 | 0 | 0 |
| | | 445 | 0 | 0 | 0 | 0 | 0 | 0 | 0 | 0 | 0 | 0 | 0 | 0 | 0 | 0 |
| | | 446 | 0 | 0 | 0 | 0 | 0 | 0 | 0 | 0 | 0 | 0 | 0 | 0 | 0 | 0 |
| | | 447 | 0 | 0 | 0 | 0 | 0 | 0 | 0 | 0 | 0 | 0 | 0 | 0 | 0 | 0 |
| | | Avg. | 0 | 0 | 0 | 0.1 | 0.1 | 0.1 | 0.2 | 3.6 | 0.1 | 0.1 | 0.4 | 0.4 | 0.4 | 3.8 |
| | 149 | 231 | 0 | 0 | 0 | 0 | 0 | 0 | 0 | 0 | 0 | 0 | 0 | 0 | 0 | 0 |
| | | 232 | 0 | 0 | 0 | 0 | 0 | 0 | 0 | 0 | 0 | 0 | 0 | 0 | 0 | 0 |
| | | 233 | 0 | 0 | 0 | 0 | 0 | 0 | 30 | | | | | | | |
| | | 234 | 0 | 0 | 0 | 0 | 0 | 0 | 3 | 1 | 1 | 3 | 1 | 1 | 1 | 1 |
| | | 235 | 0 | 0 | 0 | 0 | 0 | 0 | 3 | 2 | 3 | 3 | 0 | 0 | 0 | 0 |
| | | 236 | 0 | 0 | 0 | 0 | 0 | 0 | 0 | 0 | 0 | 0 | 0 | 0 | 0 | 0 |
| | | 237 | 0 | 0 | 0 | 0 | 0 | 0 | 1 | 1 | 1 | 1 | 1 | 1 | 1 | 1 |
| | | 238 | 0 | 0 | 0 | 0 | 0 | 2 | 0 | 0 | 0 | 0 | 0 | 0 | 0 | 0 |
| | | 239 | 0 | 0 | 30 | | | | | | | | | | | |
| | | 240 | 30 | | | | | | | | | | | | | |
| | | 241 | 3 | 30 | | | | | | | | | | | | |
| | | 242 | 0 | 0 | 0 | 0 | 0 | 2 | 3 | 3 | 30 | | | | | |
| | | Avg. | 2.8 | 2.7 | 3 | 0 | 0 | 0.4 | 4.4 | 0.9 | 4.4 | 1 | 0.3 | 0.3 | 0.3 | 0.3 |
| Group B Backpassage 6 | 209 | 448 | 0 | 0 | 0 | 0 | 0 | 0 | 0 | 0 | 0 | 0 | 0 | 0 | 0 | 0 |
| | | 449 | 0 | 0 | 0 | 0 | 0 | 0 | 0 | 0 | 0 | 0 | 0 | 0 | 0 | 0 |
| | | 450 | 0 | 0 | 0 | 0 | 0 | 0 | 0 | 0 | 0 | 0 | 0 | 0 | 0 | 0 |
| | | 451 | 0 | 0 | 0 | 0 | 0 | 0 | 0 | 0 | 1 | 1 | 1 | 1 | 1 | 1 |
| | | 452 | 0 | 0 | 0 | 0 | 0 | 0 | 0 | 0 | 0 | 0 | 0 | 0 | 0 | 0 |
| | | 453 | 0 | 0 | 0 | 0 | 0 | 0 | 0 | 0 | 0 | 0 | 0 | 0 | 0 | 0 |
| | | 454 | 0 | 0 | 0 | 0 | 0 | 0 | 0 | 0 | 1 | 1 | 1 | 1 | 1 | 1 |

TABLE 3-continued

| Treatment | Sow# | Pig# | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|---|
| | | 455 | 0 | 0 | 0 | 0 | 0 | 0 | 0 | 0 | 0 | 1 | 1 | 1 | 1 | 1 |
| | | 456 | 30 | | | | | | | | | | | | | |
| | | 457 | 0 | 0 | 0 | 0 | 0 | 0 | 0 | 0 | 2 | 1 | 1 | 1 | 1 | 1 |
| | | 458 | 30 | | | | | | | | | | | | | |
| | | Avg. | 5.5 | 0 | 0 | 0 | 0 | 0 | 0 | 0 | 0.4 | 0.4 | 0.4 | 0.4 | 0.4 | 0.4 |
| | 212 | 243 | 0 | 0 | 0 | 0 | 0 | 0 | 0 | 0 | 0 | 0 | 0 | 0 | 0 | 0 |
| | | 244 | 0 | 0 | 0 | 0 | 0 | 0 | 0 | 0 | 0 | 0 | 0 | 0 | 0 | 0 |
| | | 245 | 0 | 0 | 0 | 0 | 3 | 1 | 30 | | | | | | | |
| | | 246 | 0 | 0 | 0 | 0 | 0 | 0 | 0 | 0 | 0 | 0 | 0 | 0 | 0 | 0 |
| | | 247 | 0 | 0 | 0 | 0 | 0 | 2 | 2 | 0 | 0 | 0 | 0 | 0 | 0 | 0 |
| | | 248 | 0 | 0 | 0 | 0 | 2 | 0 | 0 | 0 | 0 | 0 | 0 | 0 | 0 | 0 |
| | | 249 | 0 | 0 | 0 | 0 | 0 | 0 | 2 | 2 | 0 | 0 | 2 | 0 | 0 | 0 |
| | | 250 | 0 | 0 | 0 | 3 | 30 | | | | | | | | | |
| | | 426 | 0 | 0 | 0 | 0 | 0 | 0 | 0 | 0 | 0 | 0 | 0 | 0 | 0 | 0 |
| | | 427 | 0 | 0 | 0 | 1 | 3 | 1 | 1 | 30 | | | | | | |
| | | 428 | 0 | 0 | 0 | 1 | 3 | 3 | 30 | | | | | | | |
| | | 429 | 0 | 0 | 0 | 0 | 2 | 3 | 3 | 3 | 3 | 3 | 3 | 1 | 30 | |
| | | Avg. | 0 | 0 | 0 | 0.4 | 3.6 | 0.9 | 6.2 | 3.9 | 0.4 | 0.4 | 0.6 | 0.1 | 3.8 | 0 |
| | 226 | Not Preg. | | | | | | | | | | | | | | |
| Group C | | | | | | | | | | | | | | | | |
| Sterile Diluent | 58 | 24 | 0 | 0 | 0 | 0 | 0 | 0 | 0 | 0 | 0 | 0 | 0 | 0 | 0 | 0 |
| | | 25 | 0 | 0 | 0 | 0 | 0 | 0 | 0 | 0 | 0 | 0 | 0 | 0 | 0 | 0 |
| | | 46 | 0 | 0 | 0 | 0 | 0 | 0 | 0 | 0 | 0 | 0 | 0 | 0 | 0 | 0 |
| | | 47 | 0 | 0 | 0 | 0 | 0 | 0 | 0 | 0 | 0 | 0 | 0 | 0 | 0 | 0 |
| | | 48 | 0 | 0 | 0 | 0 | 0 | 0 | 0 | 0 | 0 | 0 | 0 | 0 | 0 | 0 |
| | | 49 | 0 | 0 | 0 | 0 | 0 | 0 | 0 | 0 | 0 | 0 | 0 | 0 | 0 | 0 |
| | | 50 | 0 | 0 | 0 | 0 | 0 | 0 | 0 | 0 | 0 | 0 | 0 | 0 | 0 | 0 |
| | | 51 | 0 | 0 | 0 | 2 | 2 | 1 | 1 | 1 | 30 | | | | | |
| | | Avg. | 0 | 0 | 0 | 0.3 | 0.3 | 0.1 | 0.1 | 0.1 | 3.8 | 0 | 0 | 0 | 0 | 0 |
| | 113 | 17 | 30 | | | | | | | | | | | | | |
| | | 18 | 30 | | | | | | | | | | | | | |
| | | 19 | 30 | | | | | | | | | | | | | |
| | | 20 | 30 | | | | | | | | | | | | | |
| | | 21 | 0 | 30 | | | | | | | | | | | | |
| | | 22 | 30 | | | | | | | | | | | | | |
| | | 23 | 30 | | | | | | | | | | | | | |
| | | Avg. | 25.7 | 30 | | | | | | | | | | | | |
| | 117 | 52 | 1 | 0 | 0 | 0 | 0 | 0 | 0 | 0 | 0 | 0 | 0 | 0 | 0 | 0 |
| | | 53 | 0 | 0 | 0 | 0 | 0 | 0 | 0 | 0 | 0 | 0 | 0 | 0 | 0 | 0 |
| | | 54 | 0 | 0 | 0 | 0 | 0 | 0 | 0 | 0 | 0 | 0 | 0 | 0 | 0 | 0 |
| | | 55 | 0 | 0 | 0 | 0 | 0 | 0 | 0 | 0 | 0 | 0 | 0 | 0 | 0 | 0 |
| | | 56 | 1 | 0 | 0 | 0 | 30 | | | | | | | | | |
| | | 57 | 1 | 0 | 0 | 0 | 0 | 0 | 0 | 0 | 0 | 0 | 0 | 0 | 0 | 0 |
| | | 58 | 0 | 0 | 0 | 0 | 0 | 0 | 0 | 0 | 0 | 0 | 0 | 0 | 0 | 0 |
| | | 59 | 0 | 0 | 0 | 0 | 0 | 0 | 0 | 0 | 0 | 0 | 0 | 0 | 0 | 0 |
| | | 60 | 0 | 0 | 0 | 0 | 0 | 0 | 0 | 0 | 0 | 0 | 0 | 1 | 0 | 0 |
| | | 61 | 1 | 0 | 0 | 0 | 0 | 0 | 0 | 0 | 1 | 1 | 1 | 0 | 0 | 0 |
| | | 62 | 1 | 0 | 0 | 0 | 0 | 0 | 0 | 0 | 0 | 0 | 0 | 0 | 0 | 0 |
| | | Avg. | 0.5 | 0 | 0 | 0 | 2.7 | 0 | 0 | 0 | 0.1 | 0.1 | 0.1 | 0.1 | 0 | 0 |
| | 144 | 146 | 0 | 0 | 0 | 0 | 0 | 0 | 0 | 0 | 0 | 0 | 0 | 0 | 0 | 0 |
| | | 147 | 0 | 0 | 0 | 0 | 0 | 0 | 0 | 0 | 0 | 0 | 0 | 0 | 0 | 0 |
| | | 148 | 0 | 0 | 0 | 0 | 0 | 0 | 0 | 0 | 0 | 0 | 0 | 0 | 0 | 0 |
| | | 149 | 0 | 0 | 0 | 0 | 0 | 0 | 0 | 0 | 0 | 0 | 0 | 0 | 0 | 0 |
| | | 150 | 0 | 0 | 0 | 0 | 0 | 0 | 0 | 0 | 1 | 0 | 1 | 1 | 1 | 0 |
| | | 221 | 0 | 0 | 0 | 0 | 0 | 2 | 2 | 0 | 0 | 0 | 0 | 0 | 0 | 0 |
| | | 222 | 0 | 0 | 0 | 0 | 0 | 2 | 2 | 1 | 1 | 1 | 1 | 1 | 0 | 1 |
| | | 223 | 0 | 0 | 0 | 0 | 0 | 0 | 0 | 0 | 0 | 0 | 0 | 0 | 0 | 0 |
| | | 224 | 0 | 0 | 0 | 0 | 0 | 0 | 0 | 0 | 0 | 0 | 0 | 0 | 0 | 0 |
| | | 225 | 0 | 0 | 0 | 0 | 0 | 0 | 0 | 0 | 0 | 0 | 0 | 0 | 0 | 0 |
| | | 970 | 0 | 0 | 0 | 0 | 0 | 0 | 0 | 0 | 0 | 0 | 0 | 0 | 0 | 0 |
| | | 971 | 0 | 0 | 0 | 0 | 0 | 0 | 0 | 0 | 0 | 0 | 0 | 0 | 0 | 0 |
| | | Avg. | 0 | 0 | 0 | 0 | 0 | 0.3 | 0.3 | 0.1 | 0.2 | 0.1 | 0.2 | 0.2 | 0.1 | 0.1 |
| Group C Sterile Diluent | 156 | 63 | 0 | 0 | 0 | 0 | 0 | 0 | 0 | 0 | 0 | 0 | 0 | 0 | 0 | 0 |
| | | 64 | 0 | 0 | 1 | 0 | 30 | | | | | | | | | |
| | | 65 | 0 | 0 | 0 | 0 | 0 | 0 | 0 | 1 | 1 | 1 | 1 | 1 | 0 | 0 |
| | | 66 | 0 | 0 | 0 | 0 | 1 | 0 | 0 | 0 | 0 | 0 | 0 | 0 | 0 | 0 |
| | | 67 | 0 | 0 | 0 | 0 | 1 | 0 | 1 | 1 | 30 | | | | | |
| | | 68 | 0 | 0 | 0 | 0 | 0 | 0 | 0 | 0 | 0 | 0 | 0 | 0 | 0 | 0 |
| | | 69 | 0 | 0 | 0 | 0 | 0 | 0 | 0 | 1 | 0 | 0 | 0 | 0 | 0 | 0 |
| | | 70 | 0 | 0 | 0 | 0 | 0 | 0 | 0 | 0 | 0 | 0 | 0 | 0 | 0 | 0 |
| | | 71 | 0 | 0 | 0 | 0 | 0 | 2 | 2 | 0 | 0 | 0 | 0 | 0 | 1 | 0 |
| | | 72 | 0 | 0 | 0 | 0 | 0 | 0 | 0 | 0 | 0 | 0 | 0 | 0 | 0 | 0 |
| | | 73 | 0 | 0 | 0 | 0 | 0 | 0 | 0 | 0 | 0 | 0 | 0 | 0 | 0 | 0 |

TABLE 3-continued

| Treatment | Sow# | Pig# | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|---|
| | | 74 | 0 | 0 | 0 | 0 | 1 | 0 | 0 | 0 | 0 | 0 | 0 | 0 | 0 | 0 |
| | | 75 | 0 | 0 | 0 | 0 | 0 | 0 | 0 | 0 | 0 | 0 | 0 | 0 | 0 | 0 |
| | | Avg. | 0 | 0 | 0.1 | 0 | 2.5 | 0.2 | 0.3 | 0.3 | 2.6 | 0.1 | 0.1 | 0.1 | 0.1 | 0 |
| | 166 | 76 | 0 | 0 | 0 | 0 | 0 | 0 | 0 | 0 | 0 | 0 | 0 | 0 | 0 | 0 |
| | | 77 | 0 | 0 | 0 | 0 | 0 | 0 | 0 | 0 | 0 | 0 | 0 | 0 | 0 | 0 |
| | | 78 | 0 | 0 | 0 | 0 | 0 | 0 | 0 | 0 | 0 | 0 | 0 | 0 | 0 | 0 |
| | | 79 | 0 | 0 | 0 | 0 | 0 | 0 | 0 | 0 | 0 | 0 | 0 | 0 | 0 | 0 |
| | | 80 | 0 | 0 | 0 | 0 | 0 | 0 | 0 | 0 | 0 | 0 | 0 | 0 | 0 | 0 |
| | | 81 | 1 | 0 | 0 | 0 | 0 | 0 | 0 | 0 | 0 | 0 | 0 | 0 | 0 | 0 |
| | | 141 | 0 | 0 | 0 | 0 | 0 | 0 | 0 | 0 | 0 | 0 | 0 | 0 | 0 | 0 |
| | | 142 | 0 | 0 | 0 | 0 | 0 | 0 | 0 | 0 | 0 | 0 | 0 | 0 | 0 | 0 |
| | | 143 | 0 | 0 | 0 | 0 | 0 | 0 | 0 | 0 | 0 | 0 | 0 | 0 | 0 | 0 |
| | | 144 | 0 | 0 | 0 | 0 | 0 | 0 | 0 | 0 | 0 | 0 | 0 | 0 | 0 | 0 |
| | | 145 | 1 | 30 | | | | | | | | | | | | |
| | | Avg. | 0.2 | 2.7 | 0 | 0 | 0 | 0 | 0 | 0 | 0 | 0 | 0 | 0 | 0 | 0 |
| Group D | | | | | | | | | | | | | | | | |
| JA-142 | 2 | 891 | 1 | 3 | 30 | | | | | | | | | | | |
| Passage 4 | | 892 | 1 | 30 | | | | | | | | | | | | |
| | | Avg. | 1 | 16.5 | 30 | | | | | | | | | | | | |
| | 106 | Aborted | NA | | | | | | | | | | | | | |
| | 159 | 883 | 30 | | | | | | | | | | | | | |
| | | 884 | 30 | | | | | | | | | | | | | |
| | | Avg. | 30 | | | | | | | | | | | | | |
| | 190 | Aborted | NA | | | | | | | | | | | | | |
| | 206 | 890 | 30 | | | | | | | | | | | | | |
| | | Avg. | 30 | | | | | | | | | | | | | |
| | 232 | 888 | 30 | | | | | | | | | | | | | |
| | | 889 | 30 | | | | | | | | | | | | | |
| | | Avg. | 30 | | | | | | | | | | | | | |
| | 234 | Aborted | NA | | | | | | | | | | | | | |

The farrowing performance results provided the most dramatic differences and similarities between the various treatment groups. Since the treatments would not have an effect on the size of the litters, the most appropriate way to compare the farrowing results would be by using percentage values. Group A had an average percentage of live/born of 85% (SD+/−9.6). Group B had an average percentage of live/born of 89% (SD+/−11.6). The control group (group C) had an average percentage of live/born of 83.4% (SD+/−7.9). The average percentages for stillborns for groups A, B and C were 8.8 (SD+/−9.66), 6.6 (SD+/−9.7), and 14 (SD+/−11.39), respectively. The average percentages of mummies born to sows of groups A, B, and C were 6.1 (SD+/−6.01), 3.9 (SD+/−4.45), and 2.6 (SD+/−4.01), respectively. The average percentages of live/born, stillborn and mummies born to the sows of group D were 8.7 (SD+/−8.92), 10.7 (SD+/−11.39), and 81.9 (SD+/−17.18), respectively.

The results of this example demonstrated the stability of the MSV, JA-142, passage 200 after being passed in the host animal six times. There were no significant differences between the group of sows treated with the MSV (group A) and those sows that were exposed to the Backpassage 6 virus (group B) in the categories of farrowing performance, leukopenia, rectal temperatures, and the clinical observations of either the sows or the piglets. In addition, the results in these same categories for the groups A and B were comparable to those achieved by group C that had been treated with sterile diluent. Finally, the performance of the sows that had been exposed to the virulent parent virus of MSV, JA-142, passage 4, clearly illustrated the level of attenuation of the MSV and the lack of reversion to virulence by the Backpassage 6, JA-142 virus.

Example 4

Materials and Methods

This example evaluated the safety and level of attenuation of administering a 10× concentration of MSV, JA-142, passage 201. The study was performed on the pregnant sow model and monitored the effect of this dosage on reproductive performance. The study consisted of three groups, A, C, and D. Group A was inoculated intra-nasally with PRRS MSV, JA-142, passage 200. Group C was inoculated intra-nasally with sterile diluent, to act as a normal control group. Group D was inoculated intra-nasally with 10× JA-142, passage 201. All inoculations were given at about 93 days gestation. Body temperatures of the sows were monitored for the first seven days following inoculation (vaccination). Blood samples were collected from the sows once a week and at time of farrowing. Prior to and following inoculation, total white blood cell counts were determined as in Example 2. The health status of each animal was monitored daily for the duration of the study up to and following farrowing for 14 days. Clinical observations of the sows were made from −1 DPV through farrowing. The farrowing performance was evaluated by observing the health status of the piglets born. PRRSV ELISA assays were preformed following the exposures of the sows with the test article. Attempts to isolate PRRSV from serum samples were performed on MA-104 cells following exposure to the test article. Clinical observations of the piglets were made from farrowing until 14 days of age. Blood samples were collected from the piglets at birth, 7 and 14 days of age. PRRSV ELISA assays were performed on the piglet sera weekly following farrowing. Piglets were also weighed at birth, day 7 post farrowing, and at necropsy. At necropsy, the lungs of each piglet were scored for percent lung involvement.

Results and Discussion

There were no significant differences between groups given a 10× dose of MSV, JA-142, passage 201, groups given a regular dose of MSV, JA-142, passage 200, and groups given sterile diluent. Therefore, based on the safety and attenuation of MSV, JA-142, passage 200 and the lack of any significant difference in the results comparing these groups, a 10× dose of MSV, JA-142, passage 201 was shown to be safe, attenuated and effective in inducing antibodies against PRRSV.

Example 5

Materials and Methods

This example demonstrated that a minimal vaccine dose of PRRSV, JA-142, passage 205, representing MSV+5, is efficacious in an experimental respiratory challenge model in feeder pigs. Pigs were divided into three groups. Group 1 was inoculated intramuscularly with PRRS MSV, JA-142, passage 205 at a titer of 2.0 logs/dose. Group 2 was inoculated intramuscularly with sterile diluent. Group 3 acted as normal controls. Pigs from groups 1 and 2 were challenged with a PRRSV isolate with an RFLP pattern of 144 on day 28 post vaccination. Body temperatures of the pigs were monitored for the first seven days following vaccination and daily following challenge. Each animal was weighed at vaccination, challenge, weekly throughout the study, and necropsy. Blood samples were collected weekly following vaccination and every two days following challenge. The health status of each animal was monitored daily for the duration of the study. At necropsy, each animal was sacrificed and the lungs were scored for percent lung involvement as in Example 2. PRRSV ELISA assays were performed following the exposures of the pigs with the test articles and challenge. Following exposure to the test articles, attempts to isolate PRRSV from serum samples were performed on MA-104 cells. Virus isolation and ELISA results were analyzed using a Chi-square analysis which tests whether the percentage of positive animals is the same in each group. White blood cell counts were performed as in Example 2.

Results and Discussion

Pigs from group 1 (vaccinated pigs) fared better in all aspects of this example than did the pigs from group 2 (pigs given sterile diluent). Clinical scores, rectal temperatures, and percent lung involvement were all higher for the pigs given sterile diluent. Weight gain and white blood cell counts were lower for the pigs receiving the sterile diluent. There was also a significant reduction in viremia beginning on day 4 post-challenge in the group given vaccine. On days 10 and 11 post-challenge, the number of animals positive for viremia decreased further in the vaccinated group, but remained the same in the group receiving sterile diluent.

An ELISA was used to monitor anti-PRRSV serological status prior to and following vaccination and challenge. All pigs were negative (S/P ratio<0.4) at the time of vaccination. All pigs including the vaccinates were negative at 7 DPV (Days Post Vaccination). Seven days later, 21 of 22 vaccinated pigs were tested as positive for antibody to PRRSV. Two pigs of group 1 remained negative during the pre-challenge period and serological converted at 8 days post challenge (8 DPC). All of the pigs in group 2 were negative at trial day 0 and remained negative throughout the pre-challenge period. On trial day 39 (8 DPC) 17 of the 22 non-vaccinated challenged pigs (Group 2) tested as sero positive. All of the pigs in group 3 (normal controls) remained sero-negative throughout the study.

Virus isolations from sera were performed before and after vaccination. Of the 22 vaccinated pigs, 17 were positive by 2 DPV, 18 were positive by 4 DPV and 19 were positive by 7 DPV. Following vaccination, vaccine virus was not recovered at all from one pig and not until 0 DPC for another. These results correspond to the sero-negative status of these pigs during the post vaccination observation period. At the time of challenge, 55% of the vaccinated pigs were viremic positive. Following challenge, this percentage rose to 82% (at 2 DPC) and gradually decreased to 9% on 11 DPC. All pigs in group 2 were negative at 0 DPC and increased to 82% positive at 2 DPC and 91% at 4 DPC. On 6 and 10 DPC, group 2 was approximately 82% virus positive and 73% of this group was positive on 11 DPC. The normal controls, group 3, remained negative for the duration of the study.

Rectal temperature monitoring showed an overall group increase experienced by group 2. One-half of the pigs in this group experienced a rise of 1° F. over the pre-challenge average for 2 or more days during the 11 day observation period. In comparison, only four of the 22 pigs in the vaccinated group experienced temperatures of 1° F. over their pre-challenge average. The average duration of those animals experiencing elevated temperatures for two or more days was 2.2 days for group 1 and 4 days for group 2. None of the pigs in group 3 experienced increases of 1° F. over their pre-challenge average for two days or longer.

Weight gain was monitored over the 11 day observation period. Pigs in group 3 gained an average of 1.06 pounds/day, pigs in group 2 gained an average of 0.94 pounds/day and pigs in group 1 gained an average of 0.53 pounds/day. Therefore, non-vaccinated challenged pigs gained only about 57% as much weight as did vaccinated challenged pigs and only 50% as much weight as the control group.

Leukopenia (white blood cell counts) were monitored during the post challenge observation period. Group 3 experienced a 5% reduction in the group average on trial day 33 (2 DPC) when compared to the pre-challenge average. For group 2, white blood cell counts dropped an average of 41% and did not return to pre-challenge levels until 11 DPC. The vaccinated group experienced a group average drop of 12% on trial day 34 (3 DPC). The counts returned to pre-challenge level on the next day and remained equal to the pre-challenge level for the duration of the observation period.

Daily clinical observations were made from trial day 28 (−4 DPC) through trial day 42 (11 DPC). All pigs were free of any observable clinical signs during the pre-challenge period. Group 3 remained free of any clinical signs for the duration of the post challenge period. Five of the pigs in group 2 were observed to have post challenge clinical signs. These signs became evident at 6 DPC and were not considered to be severe. The vaccinated pigs had only 1 clinical sign observed during the 11 day post challenge observation period.

At the termination of the study, lungs were evaluated for observable lung lesions. Group 3 had normal lungs and a group average score of 0.02. The individual pig scores for group 2 ranged from a low of 33 to a high of 98 for a group average of 78.33. The scores of the vaccinated group ranged from 30 to a high of 90 with a group average of 53.20.

The data in this example demonstrated the efficacy of a modified live Atypical PRRS viral vaccine. The vaccine was administered at a minimal dose of 2.0 logs per dose containing the fifth passage beyond the MSV (JA-142, passage 205). Efficacy of the vaccine was demonstrated by significantly reducing the extent of lung lesions, the severity of post challenge leukopenia, and post challenge fever. Additionally, a normal growth rate was maintained in vaccinated/challenged pigs compared to that achieved by the normal control pigs and significantly better than that achieved by non-vaccinated/challenged pigs.

Example 6

Materials and Methods

This example compared four groups, groups 1, 2, and 3 having twenty pigs each, and group 4 having 10 pigs. Group 1 was inoculated intramuscularly (IM) with PRRS MSV, JA-142, passage 205, at a titer of about 2.5 logs/dose. Group 2 was inoculated intra-nasally with PRRS MSV, JA-142, passage 205, at a titer of about 5.0 logs/dose. Group 3 was inoculated IM with sterile diluent. Group 4 acted as strict controls. Pigs were challenged with a PRRSV isolate from South Dakota State University (SDSU) with an RFLP pattern of 144 on day 28 post-vaccination. Body temperatures of the pigs were monitored daily following challenge. Each animal was weighed at vaccination, challenge, weekly for the duration of the study, and necropsy. Blood samples were collected weekly following vaccination and every two days following challenge. The health status of each animal was monitored daily for the duration of the study. At the termination of the study, animals were sacrificed and their lungs scored for percent lung involvement.

PPRSV ELISA assays were performed following the exposures of the pigs with the test articles and challenge. Attempts to isolate PRRSV from serum samples were also performed on MA-104 cells following exposure to the test articles. WBC counts and clinical observations were determined post inoculation as in Example 2.

Results and Discussion

At zero days post vaccination (DPV), all pigs in this example were serologically negative to PRRSV as indicated by having a S/P ratio<0.4. At 14 DPV, 70% of the pigs in group 1 and 95% of the pigs in group 2 tested positive for the presence of anti-PRRSV antibody. Only one vaccinated pig of group 1, remained sero-negative throughout the pre-challenge period. This pig became sero-positive at seven days post challenge (DPC). All of the pigs in groups 3 and 4 remained negative throughout the pre-challenge period. At nine DPC, all of the pigs in group 3, the sterile diluent treated group, tested positive by ELISA for PRRSV antibody. The normal controls, group 4, remained negative for the duration of the study.

The virus isolation results correlated well with serological results. Only one pig remained negative for virus isolation from serum and this corresponded to the sero-negative status during the post vaccination period. These results indicate a relationship between post vaccination viremia and serological conversion with vaccine dosage. Group 2 was 100% sero-positive at 14 DPV as compared to 70% for group 1. The high dose group (group 2) was 85% and 90% viremia positive at 14 and 21 DPV, respectively. In comparison, the low dose group (group 1) was 55% and 85% positive for the same test days.

Following challenge, 89% of the animals in group 3 experienced temperatures that were one degree F. or greater than the pre-challenge values for two or more days. In group 1, 75% of the animals experienced temperatures of one degree or greater for two or more days. While only 45% of the animals of group 2 experienced elevated temperatures. In comparison, 30% of the animals in the normal control group (group 4) experienced elevated temperatures for two or more days during the 11 day observation period.

Treatment with either the high vaccine dose or the low vaccine dose appeared to have no detrimental effect on the growth performance during the post-vaccination period (−3 DPV to 28 DPV). The average daily weight gain for groups 1 and 2 was 0.77 lbs./day and 0.76 lbs./day, respectively. For comparison, groups 3 and 4 had average daily weight gains of 0.77 lbs. and 0.78 lbs., respectively. Following challenge, the vaccinated groups outperformed the sterile diluent group by 0.05 lbs./day (group 1) and 0.15 lbs./day (group 2). The normal controls outgained the vaccinates during the same time period by an average of 0.4 to 0.5 lbs./day.

Eighty-four percent (16 of 19) of group 3, the sterile diluent treatment group, experienced a 25% or greater drop in their WBC count for one or more days after challenge. The normal controls had 3 of 10 (30%) that had experienced similar decreases. Following challenge, the vaccinated groups, the low dose (group 1) and the high dose (group 2) had 11 of 20 (55%) and 3 of 20 (15%) experiencing leukopenia of 25% for one or more days.

The clinical observations made prior to the challenge indicated that the pigs were of good health status. Following challenge, the level of health status did not significantly change for those pigs that were challenged (groups 1, 2, & 3). Lethargy, respiratory signs, and lost appetite were the clinical signs observed and these were described as mild in severity. The clinical signs reported for one pig in group 2 could be attributed to the bacterial pneumonia (see discussion below on lung lesions) that it was experiencing. The normal control group (group 4) was free of any observable clinical signs during the 11 day observation period.

At the termination of the study, pigs were sacrificed and the lungs were observed for PRRS-like lesions to score the extent of lung involvement. The percent of involvement was scored for each lobe then multiplied by the percent the lung represented for the total lung capacity. For example, 50% lung involvement for a diaphragmatic lobe was then multiplied by 25% to equal 12.5% of the total lung capacity. The maximum score that could be obtained was 100. The group average lung score for the normal controls (group 4) was zero. The group average score for the sterile diluent treatment group (group 3) was 70.08. The vaccinated treatment groups average scores were 48.83 for the low dose (group 1) and 17.76 for the high dose (group 2). One pig was observed to have a lung score of 62.5, the highest score within group 2. The lesions noted on this pig's lungs were described to be associated with bacterial pneumonia.

From the results of this study, both dosage levels of the atypical PRRS MSV vaccine reduced the severity of the clinical signs associated with the respiratory disease caused by the PRRSV. A full field dose outperformed the minimal dose as indicated by the significant reduction in lung lesion scores.

Example 7

Materials and Methods

This example determined the sequence of the attenuated MSV, JA-142 from the 201st passage as well as the sequence of passage 3 of the field isolate virus, JA-142. The attenuated virus isolate was obtained from the master seed stock representing the 201st passage in MA-104 simian cells of a PRRSV isolated from swine affected with PRRS.

The virus was grown on 2621 cells, a monkey kidney cell line, also referred to as MA-104 and as USU-104 (Gravell et al., 181 Proc. Soc. Exp. Biol. Med. 112-119 (1986), Collins et al., Isolation of Swine Infertility and Respiratory Syndrome Virus (Isolate ATCC VR-2332) in North America and Experimental Reproduction of the Disease in Gnotobiotic Pigs, 4 J. Vet. Diagn. Invest. 117-126 (1992)) (the teachings of which are hereby incorporated by reference). Cells were cultured in 50 ml Dulbecco modified Eagle's MEM medium (Life Technologies, Inc., Gaithersburg, Md.), supplemented with 10% fetal calf serum and 50 µg/ml gentamicin (Sigma Chemical Co., St. Louis, Mo.) in a 5% humidified $CO_2$ atmosphere at 37° C. in 75 $cm^2$ plastic tissue culture flasks. Cells were maintained by passage at 5-7 day intervals. Cells were dislodged from the surface with trypsin-versene and split 1:4. To infect cells, media was decanted and 1 ml of cell supernatant containing virus at a titer of approximately $10^5$-$10^6$ tissue culture infective doses ($TCID_{50}$) was added for 30 min. Thirty ml fresh media containing 4% fetal calf serum was added. Cells were incubated as described above for 5 days, at which time cytopathic effect was evident in the culture. Culture medium containing virus was centrifuged at 2000 rpm in a Beckman TJ6 centrifuge to pellet cellular debris.

Viral genomic RNA was purified by adding 1120 µl of prepared Buffer AVL (QIAamp Viral RNA Isolation Kit, Qiagen)(QIAGEN, Inc. Valencia, Calif.)/carrier RNA to a 280 µl sample of virus-containing culture medium. The mixture was vortexed and incubated at room temperature for 10 min. 1120 µl ethanol was added and the mixture was inverted several times. RNA was absorbed to the matrix of a QIAamp spin column by repeated centrifugation of 630 µl aliquots at 6,000×g for 1 min. The column was washed with 500 µl buffer AW and centrifuged to remove all traces of wash solution. RNA was eluted from the column with 60 µl of diethylpyrocarbonate-treated water at room temperature. Purified RNA was stored at −70° C. or used immediately for synthesis of cDNA.

For cDNA synthesis, viral RNA was heated at 67° C. for 7 min, primed with random hexamers or PRRSV-specific primers, and reverse transcribed with Superscript II RNase H⁻ reverse transcriptase (RT) (Life Technologies, Inc.). Reactions contained 5 mM $MgCl_2$, 1× standard buffer II (Perkin Elmer Corp. Wellesley, Mass.), 1 mM each of dATP, dCTP, dGTP and dTTP, 1 unit/µl of RNase inhibitor, 2 units of RT, and 1 µl of RNA in a 40 µl reaction. Reaction mixtures were incubated for 15 min at 42° C., for 5 min at 99° C. and for 5 min at 5° C.

Polymerase chain reaction (PCR) was performed to obtained DNA fragments for sequencing as follows: 10 µl portions of cDNA reaction mixture were combined with the following reagents, resulting in a 25 µl reaction containing 2 mM $MgCl_2$, 1× standard buffer II (Perkin Elmer), 0.2 mM each of dATP, dCTP, dGTP and dTTP, 0.3 µM of 5'- and 3'-PRRSV-specific primer, and 0.375 units AmpliTaq Taq polymerase (Perkin Elmer). Reactions were prepared by heating for 4 min at 93° C. in a thermal cycler, then 35 cycles consisting of 50-59° C. for 30 sec, 72° C. for 30-60 sec, and 94° C. for 30 sec. Specific times and temperatures varied depending on the annealing temperatures of the primers in each reaction and the predicted length of the amplification product. A final incubation was performed for 10 min at 72° C. and reactions were placed at 4° C. PCR products were purified with a Microcon 100 kit (Amicon, Bedford, Mass.).

Rapid amplification of cDNA ends (RACE) PCR was performed to obtain the extreme 5'-end sequence of the genomic RNA, based on the method of Frohman, Mass., On Beyond Classic RACE (Rapid Amplification of cDNA Ends), 4 PCR Methods and Applications S40-S58 (1994) (the teachings of which are hereby incorporated by reference). Viral RNA was isolated and converted to cDNA as described above, with random hexamers as primers. Reaction products were purified on a Microcon 100 column (Amicon). A poly(dA) tail was added to the 3'-end by incubating 10 µl of cDNA in a 20 µl volume containing 1× buffer 4 (New England Biolabs, Beverly, Mass.), 2.5 mM $CoCl_2$, 0.5 mM dATP and 2 units terminal transferase (New England Biolabs), for 15 min at 37° C. The reaction was stopped by heating for 5 min at 65° C. and then was diluted to 200 µl with water.

PCR was performed using the Expand$^a$ Long Template PCR System (Boehringer Mannheim, Mannheim, Germany) in a 50 µl reaction volume containing 10 µl of diluted, poly (dA)-tailed cDNA, 1× buffer 3, 0.35 mM each of dATP, dCTP, dGTP and dTTP, 0.625 mM $MgCl_2$, 0.04 µM $Q_t$ primer (Frohman, 1994), 0.3 µM $Q_o$ primer (Frohman, 1994), 0.3 µM 5'-CGCCCTAATTGAATAGGTGAC-3' and 0.75 µl of enzyme mix. Reactions were heated at 93° C. for 2 min in a thermal cycler and cycled 25 times with each cycle consisting of 93° C. for 10 sec, 63° C. for 30 sec, and 68° C. for 12 min. After 25 cycles, the reaction was incubated at 68° C. for 7 min and held at 4° C. An aliquot of the reaction was diluted 100-fold and 5 µl of diluted product was added to a second PCR reaction containing, in 50 µl, 1× buffer 1, 0.35 mM each of dATP, dCTP, dGTP and dTTP, 0.3 µM primer Qi (Frohman, 1994), 0.3 µM 5'-CCTTCGGCAGGCGGGGAGTAGT-GTTTGAGGTGCTCAGC-3', and 0.75 µl enzyme mix. Reactions were heated at 93° C. for 2 min in a thermal cycler and cycled 25 times with each cycle consisting of 93° C. for 10 sec, 63° C. for 30 sec, and 68° C. for 4 min. After 25 cycles, the reaction was incubated at 68° C. for 7 min and held at 4° C. Reaction products were electrophoresed on a 1% agarose gel and the band of approximately 1500 bp was purified using the QIAgen QXII gel purification kit. Eluted DNA was cloned into the pGEM-T vector (Promega, Madison, Wis.) using standard procedures. Individual clones were isolated and grown for isolation of plasmid DNA using QIAgen plasmid isolation kits.

PCR products and plasmid DNA were combined with appropriate primers based on related PRRSV sequences in Genbank or derived from known sequences, and subjected to automated sequencing reactions with Taq DyeDeoxy terminator cycle sequencing kits (Applied Biosystems, Foster City, Calif.) and a PR 2400 Thermocycler (Perkin Elmer) at the University of Minnesota Advanced Genetic Analysis Center. Reactions were electrophoresed on an Applied Biosystems 3700 DNA sequencer. Sequence base calling and proofreading were performed primarily with the Phred program (University of Washington Genome Center) and fragment assembly was performed primarily with the Phrap program (University of Washington Genome Center). Additional computer software including the Lasergene Package (DNASTAR Inc., Madison, Wis.), Wisconsin package version 9.1 (Genetics Computer Group, Madison, Wis.), and EuGene (Molecular Biology Information Resource, Houston, Tex.) was used to analyze the sequence. The final viral genomic sequence was assembled from approximately 100 PCR reactions and 428 DNA sequencing reactions.

Results

The results of Example 7 are given as SEQ ID Nos. 1 and 2 wherein SEQ ID No. 1 represents the DNA sequence of the 201st passage of the Master Seed Virus, JA 142 and SEQ ID No. 2 represents the DNA sequence of the field-isolated virulent virus, JA 142 after three passages. Additionally, RNA sequences of the 201st passage JA-142 and the field isolated virulent virus, JA-142 are provided as SEQ ID Nos. 3 and 4, respectively. These RNA sequences vary slightly from the DNA sequences at the 5' end of the genome.

Example 8

Materials and Methods

This example demonstrated the presence or absence of a NspI restriction endonuclease site for differentiation between field strains of PRRSV and an attenuated strain of PRRSV. Thus, this example provides a diagnostic testing method using restriction fragment length polymorphism (RFLP) analysis. RFLP is useful as a diagnostic tool because the NspI site is present in most field strains of PRRSV. Samples, preferably of serum, should be gathered from a suspected infected individual for RT-PCR/RFLP based diagnostic testing. In this case, known virulent field strains were used for testing to provide known result standards for later diagnostic testing. While Qiagen products and specific method steps are disclosed, it is understood that other methods and products known in the art can be utilized.

For performance of the diagnostic test (and to obtain the standards disclosed below) viral genomic RNA was isolated using a QIAamp Viral RNA Isolation Kit (Qiagen, Inc. Valencia, Calif.) and following the mini spin protocol. The following steps were used:

1. Carrier RNA was added to Buffer AVL and placed at 80° C. for five minutes or until dissolution of the precipitate to form solution 1. Do not heat Buffer AVL over 5 minutes or more than 6 times. Frequent warming/extended incubation will cause degradation of carrier-RNA, leading to reduced recovery of Viral RNA and eventually false negative RT-PCR results.
2. 1120 µl of solution 1 was pipetted into a microfuge tube.
3. 280 µl of serum sample was added to the microfuge tube holding solution 1 and the resulting mixture was vortexed thoroughly to ensure that solution 1 and the sample were well mixed together. This is done to lyse the sample under highly denaturing conditions, inactivate RNases, and ensure isolation of intact viral RNA. Carrier-RNA improves binding of viral RNA to the QIAamp membrane, and limits possible degradation of the viral RNA due to any residual RNase activity.
4. This mixture was incubated at room temperature for 10 minutes. Viral particle lysis is substantially complete after lysis for 10 minutes at room temperature, although longer times may be used with little or no effect on the yield or quality of the purified RNA.
5. 1120 µl of ethanol (EtOH) (96-100%) was added to the incubated mixture and mixed thoroughly by inverting the tube several times.
6. A QIAamp spin column was placed in a 2 ml collection tube and 630 µl of the mixture obtained in step five was added. This mixture was then centrifuged at 6000×g for one minute.
7. The filtrate in the collection tube was discarded.
8. The QIAamp spin column was placed into a clean 2 ml collection tube and another 630 µl of the mixture obtained in step five was added to the spin column and centrifuged at 6000×g.
9. The filtrate in the collection tube was discarded.
10. The QIAamp spin column was placed into a clean 2 ml collection tube and another 630 µl of the mixture obtained in step five was added to the spin column and centrifuged at 6000×g.
11. 500 µl of Buffer AW1 was added to the spin column and centrifuged at 6000×g for one minute.
12. The tube containing the filtrate was discarded.
13. The spin column was placed into a clean 2 ml collection tube and 500 µl of Buffer AW2 was added and centrifuged at 18,500×g for three minutes. The filtrate was discarded.
14. The spin column was placed into a new 2 ml collection tube and centrifuged at 6000×g for one minute to remove the last traces of AW2. The filtrate was discarded.
15. The spin column was placed into a clean 1.5 ml microcentrifuge tube and 60 µl of Buffer AVE at room temperature. This mixture was incubated for one minute at room temperature before being centrifuged at 6000×g for one minute to elute the RNA.
16. The eluted RNA was pipetted into a 1.5 ml microfuge tube and stored at −70° C. if the RT-PCR is not able to be done immediately.

RT-PCR was performed on the eluted RNA obtained in the above method. A 20 µl "master mix" containing the following: 5 µl of 1×RT-PCR buffer, 1 µl of 0.4 mM DNTP mixture (containing equal amounts each of dATP, dCTP, dGTP and dUTP), 0.1 µl of 0.08 units/Rx RNAse inhibitor, 0.5 µl 500 nM BVDV forward primer, 0.5 µl 500 nM BVDV reverse primer, 11.9 µl RNAse/DNAse free water, and 1 µl Qiagen "secret" enzyme mix was added to a tube. 5 µl of the eluted RNA was then added to the tube.

Reactions were initially heated at 50° C. for 30 minutes followed by heating at 95° C. for 15 minutes in a thermal cycler and then cycled 35 times with each cycle consisting of 57° C. for 30 seconds, 72° C. for 45 seconds, and 94° C. for 45 seconds. After 35 cycles, the reaction was incubated at 57° C. for 30 seconds followed by 72° C. for 7 minutes and finally held at 4° C. To check the PCR on an agarose gel, 1 g of agarose was added to 100 ml of 1×TAE buffer before microwaving on high for two minutes. Next, 4 µl of 10 mg/ml EtBr was added to the heated gel before casting the gel and allowing it to solidify for 15-30 minutes. 4 µl of the PCR product was mixed with 1 µl loading dye. 3.5 µl of a 1 Kb ladder was added to 13.2 µl of water and 3.3 µl of loading dye for use as a marker. 4 µl of the marker mixture was electrophoresed on the gel, indicating a 1 Kb product. A band from the PCR product should be approximately 1 Kb in size. The gel was then run at 140 volts for 1 hour or 75 volts for two hours.

The band of approximately 1 Kb was purified using the QIAgen Qiaquick PCR Purification Kit (Qiagen, Inc. Valencia, Calif.). A column was placed in a collection tube and 20 µl PCR reaction sample and 100 µl PB buffer were added. This mixture was mixed thoroughly before spinning for 1 minute at full speed in an Eppendorf microfuge. The flow-through products were discarded and the column was replaced in the tube. The tube was spun for another full minute and allowed to stand for at least one minute at room temperature. The column was then spun a third time at full speed. The eluent remaining contains purified PCR product and water.

The PCR/water product from above was then digested with Nsp I, a restriction enzyme and then electrophoresed on a 1.5% agarose gel to determine fragment numbers and lengths.

Results

The results of Example 8 are used for diagnostic results. It was found that most of the field strains for the PRRS virus contain one Nsp I restriction site, therefore yielding digestion products of 549 and 476 bp from the 1 Kb RT-PCR product. The parent strain of the JA-142 passage 200 possesses this phenotype. Only one PRRS strain, BI-Vetmedica 142 passage 200 (+5), contains two Nsp I sites, yielding digestion products of 476, 380, and 173 bp from the 1 Kb RT-PCR product. Some field strains possess no Nsp I site within this RT-PCR product, and therefore exhibit no digestion and electrophoresis of one fragment of 1021 bp. Thus, the presence of the attenuated virus can be determined.

Example 9

Materials and Methods

This Example tested the degree of protective immunity against maternal reproductive failure of swine vaccinated by one or two attenuated strains of PRRSV.

Fifty gilts were separated into five experimental groups designated A-E and having ten gilts in each group. Gilts of group A were neither vaccinated nor challenged and were therefore used as strict controls. Gilts of group B were used as the challenge controls and therefore received no vaccinations but were challenged at or about day 90 of gestation. Gilts of groups C, D, and E were each vaccinated twice before conception with one month between vaccinations. These gilts were then challenged at or about day 90 of gestation. Two strains of vaccine virus (strains RespPRRS/Repro and JA-142) were used to challenge the gilts. The challenge consisted of oronasal exposure to virulent PRRSV. Gilts of group C were vaccinated twice with strain RespPRRS/Repro. Gilts of group D were vaccinated first with RespPRRS/Repro and then with JA-142. Gilts of group E were vaccinated twice with strain JA-142. Gilts and their progeny were observed at least twice daily for clinical signs and tested for both PRRSV and homologous antibody at selected intervals. The gilts of groups C, D, and E were bled just before their first vaccination and at selected times thereafter until they were necropsied, usually at or about 14 days after farrowing or sooner if they aborted. Gilts of group A and B were bled just before challenge and at identical selected times thereafter. Beginning one month after the second vaccination of groups C, D, and E, all gilts were bred as they came into estrus. All of the boars used for breeding purposes were free of antibody against PRRSV. Near the time of challenge, each gilt was moved to an isolation room and was kept in isolation until the experiment was ended for that gilt and her litter at two weeks after farrowing or sooner in the case of abortion or premature death of all progeny. All surviving pigs were weighed when they were two weeks old. Gilts that failed to conceive at their first, second, or third estrocycle were excluded from the experiment. This reduced the numbers of pregnant gilts for groups B, C, D, and E to 9, 8, 9, and 9, respectively. The same limitation did not apply to group A because for this group, there were more than ten nonvaccinated gilts available from which to make a random selection for inclusion in group A.

Results and Discussion:

All vaccinated gilts (groups C, D, and E) responded to vaccination with the production of antibodies against PRRSV. These results are provided in FIG. 1 which is a graph representing the ratio of the total number of samples to samples positive for PRRSV antibodies. Blood samples were collected from the gilts just before their first vaccination and at selected times thereafter during an interval of 196 days. Depending on when gilts conceived (breeding was started on day 60), they were progressively removed from this group. Beginning at or about 90 days of gestation, blood samples were collected just before they were challenged, seven days after challenge, fourteen days after challenge, at the time of delivery (which was at or about 24 days after challenge if the gilt farrowed normally, or sooner if the gilt aborted), and at the time of necropsy (which was at or about 38 days, i.e. 2 weeks after farrowing, or sooner if the gilt lost all of her live born pigs before 2 weeks after farrowing). These results are provided in FIG. 2.

Figure 2:
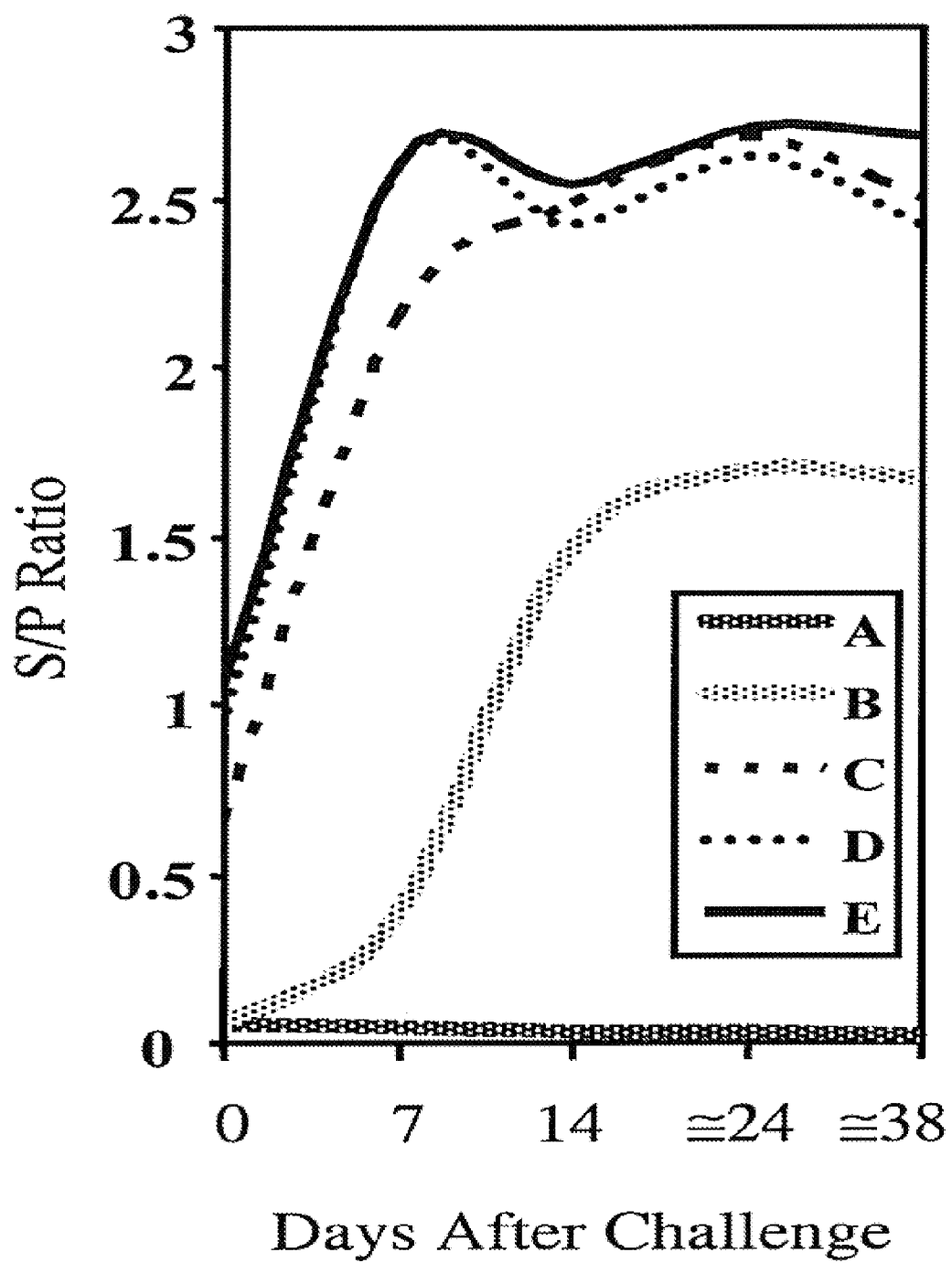
FIG. 2 is a graph illustrating the ratio of samples which tested positive for antibodies against PRRSV to the total number of samples over a 38 day testing period after challenge.

As shown in FIGS. 1 and 2, antibody levels increased after challenge for groups B, C, D, and E. For group B, the nonvaccinated group, these antibodies appeared only after challenge while they were present prior to challenge for groups C, D, and E. Gilts of group A and all boars used for breeding both vaccinated and nonvaccinated gilts remained free of antibody against PRRSV throughout the experiment. None of the vaccinated gilts had any obvious vaccine-related clinical signs after vaccination. Conversely, all of the gilts (both vaccinated and nonvaccinated) had moderate to severe clinical signs following challenge. A summary of the number of live born and still born pigs, the number of aborted, late term dead, and mummified fetuses, and the number and weight of pigs still alive 14 days after farrowing is presented in Table 4. All of the pigs of groups C, D, and E that survived through day 14 were robust and were judged to be in excellent health. None of these pigs yielded infectious virus from either serum or lung lavage samples. In contrast, all pigs of group B that survived through day 14 were unthrifty and were shown by virus isolation to be infected. A measure of the difference in general health is provided by the relative body weights of pigs of group B versus those of pigs of groups A, C, D, and E. The appearance of pigs of group B suggested that few, if any, would have recovered or would have recovered sufficiently to warrant any expectation of their continued survival under conditions of commercial swine production.

TABLE 4

Effect of Vaccination Against Porcine Reproductive and Respiratory Syndrome Virus (PRRSV) on the Health and Survival of Fetuses and Pigs of Gilts Subsequently Exposed to Highly Virulent PRRSV

| | | Day 0[1] | | | | | Day 14[2] | | Mean |
|---|---|---|---|---|---|---|---|---|---|
| Group | Gilts[3] | Liveborn pigs | Stillborn pigs | Late-term dead fetuses | Mummified fetuses | Aborted fetuses | Live pigs | Mean pig weight (lbs) | litter weight (lbs) |
| A | 10 | 102 | 17 | 1 | 2 | 0 | 95 | 9.8 | 93.1 |
| B | 9 | 24 | 3 | 62 | 5 | 0 | 16 | 5.6 | 10.0 |
| C | 8 | 37 | 8 | 31 | 4 | 13 | 27 | 11.1 | 37.5 |
| D | 9 | 47 | 10 | 14 | 0 | 39 | 38 | 8.7 | 36.7 |
| E | 9 | 50 | 13 | 38 | 3 | 0 | 33 | 10.4 | 38.1 |

[1]At the time of farrowing.
[2]On the day the experiment was ended.
[3]Pregnant gilts that aborted or farrowed.

Vaccination with either strain (RespPRRS/Repro and JA-142) of attenuated PRRSV provided a level of protective immunity that was demonstrated by challenge exposure. Although protection was incomplete regardless of the vaccine strain or method of vaccination, it was sufficient to recommend vaccination as an economically beneficial procedure. Whereas the loss of pigs of group B was essentially complete either due to death or ill health, about 40% of the pigs of litters of groups C, D, and E (on a per litter basis and using 100% as the value for litters of group A) would have survived to market. The excellent health status of the surviving pigs of groups C, D, and E is emphasized by the fact that the mean body weight of pigs of these groups (when calculated collectively) is the same as that of pigs of group A. The economic impact of saving about 3.6 pigs/litter through vaccination is difficult to project with certainty, however, if a reasonable assumption is made that each pig is worth about $20.00 in profit and reduced overhead through sharing of fixed costs, then two vaccinations at an estimated cost of about $1.00 each would return $72.00 for each $2.00 invested. On the basis of these assumptions, anything more than a prevalence of PRRSV-induced reproductive failure of one case for every 36 pregnancies (or a severe clinical epidemic once every 18 months assuming 2 pregnancies/year) would make vaccination cost effective. Moreover, it seems likely that the results of this study present the worst case scenario. Namely, the strain used for challenge was selected to represent the most virulent field strains of PRRSV currently present in North America and may not accurately reflect the majority of field strains against which vaccines are likely to be more protective.

We claim:

1. An isolated cDNA sequence that encodes an infectious RNA sequence of a PRRS virus, said cDNA having at least 95% sequence identity with a sequence selected from the group consisting of SEQ ID No. 1 or SEQ ID No. 2 but is subsequently attenuated by passage at least 200 times in serial culture.

2. The cDNA sequence of claim 1, wherein administration of PRRS virus RNA sequence complementary to said cDNA sequence to a host animal confers effective immunity against PRRS virus infection.

3. The cDNA sequence of claim 1, wherein said nucleic acid sequence has an RNA sequence encoded by a cDNA sequence selected from the group consisting of SEQ ID NO:1 and a cDNA sequence that initially corresponds to a cDNA sequence of SEQ ID NO:2 but is subsequently attenuated by passage at least 200 times in serial cell culture.

4. A method of vaccinating swine against reproductive or respiratory failure comprising the steps of: administering to said swine a vaccine, said vaccine comprising at least one attenuated strain of PRRSV having an RNA sequence that is encoded by a cDNA sequence having at least 95% sequence identity with a sequence selected from the group consisting of SEQ ID No. 1 or a PRRS virus having an RNA sequence that is initially encoded by the cDNA sequence of SEQ ID No. 2 but is subsequently attenuated by passage at least 200 times in serial cell culture.

5. The method of claim 4, said strain is a JA-142 PRRS virus strain comprising an RNA sequence that is encoded by the cDNA sequence of SEQ ID NO:2 but is subsequently attenuated by passage at least 200 times in serial cell culture.

6. The method of claim 4, said PRRSV strain being an attenuated JA-142 comprising an RNA sequence that is encoded by the cDNA sequence of SEQ ID NO:1.

7. The method of claim 4, said reproductive or respiratory failure resulting from infection by PRRSV.

8. The method of claim 4, said administering step occurring at least two times wherein the two administrations are separated by about 30 days.

9. The method of claim 4, said method vaccinates against incidence of abortion, incidence of stillborn pigs and decreased viability of liveborn pigs caused by infection with PRRSV.

10. The method of claim 4, said administering step is administered to a swine of farrowing age prior to said pig becoming pregnant.

* * * * *

SEQUENCE LISTING

<160> NUMBER OF SEQ ID NOS: 6

<210> SEQ ID NO 1
<211> LENGTH: 15424
<212> TYPE: DNA
<213> ORGANISM: Porcine reproductive and respiratory syndrome virus

<400> SEQUENCE: 1

```
tcgcccgggc aggtgttggc tctatgcctt ggcatttgta ttgtcaggag ctgcgaccat      60
tggcacagcc caaaactagc tgcacagaaa acgcccttct gtgacagccc tcttcagggg     120
agcttagggg tctgtcccta gcaccttgct tccggagttg cactgcttta cggtctctcc     180 aacccttaa ccatgtctgg gatacttgat cggtgcacgt gcaccccca tgccagggtg      240 tttatggcgg agggccaagt ctactgcaca cgatgtctca gtgcacggtc tctccttcct     300
ctgaatctcc aagttcctga gcttggagtg ctgggcctat tttacaggcc cgaagagcca     360
ctccggtgga cgttgccacg tgcattcccc actgttgagt gctcccccgc cggggcctgc     420
tggctttctg cgatctttcc aattgcacga atgaccagtg gaaacctgaa ctttcaacaa     480
agaatggtgc gggtcgcagc tgagatttac agagccggcc agctcacccc tgcagtcttg     540
aaggctctac aagtttatga acggggttgc cgctggtacc ctatagtcgg acctgtccct     600
ggagtggccg attttgccaa ctccctacat gtgagtgata aacctttccc gggagcaact     660
catgtgctaa ccaacctgcc actcccagag aggcctaagc ctgaagactt tgcccttct     720 gagtgtgcta tggctgacgt ctatgatatt ggccatggcg ccgtcatgta tgtggccaaa     780
gggaaagtct cctgggcccc tcgtggcggg gatgaggcga aatttgaacc tgtccctagg     840
gagttgaagt tgatcgcgaa ccaactccac atctccttcc cgccccacca cgcagtggac     900
atgtctaagt ttgtgttcat agcccctggg agtggtgtct ctatgcgggt cgagtgccca     960
cacggctgtc tccccgctaa tactgtccct gaaggtaact gctggtggcg cttgtttgac    1020
tcgctcccac tggacgttca gaacaaagaa attcgccgtg ccaaccaatt cggctatcaa    1080
accaagcatg gtgtcgctgg caagtaccta caacggaggc tgcaagctaa tggtctccga    1140
gcagtgactg atacagatgg acccattgtc gtacagtatt tctctgttag ggagagctgg    1200
atccgccact tcagactggc ggaagagcct agcctccctg ggtttgaaga cctcctcaga    1260
ataagggtag agcccaatac gtcgccattg agtgacaagg gtggaaaaat cttccggttt    1320
ggcagtcaca aatggtacgg tgctggaaag agagcaagga aagcacgctc tggtatgacc    1380
accacagtcg ctcaccgcgc cttgcccgct cgtgaaatcc agcaagccaa aaagcacgag    1440
```

-continued

```
gatgccggcg ctgataaggc tgtgcatctc aggcactatt ctccgcctgc cgacgggaac   1500
tgtggttggc actgcatttc cgccatcgcc aaccgaatgg tgaattccaa atttgaaact   1560
actcttcccg agagggtgag accttcagat gactgggcta ctgacgagga ccttgtgaac   1620
accatccaaa ttctcaagct ccctgcggcc ttggacagga acggtgcttg tgttggcgcc   1680
aaatacgtgc ttaagctgga aggcgagcat ggactgtct ctgtgaccct gggatgtcc    1740
ccttcttgc tccccttga atgtgttcag ggctgttgtg agcataagag cggacttggt    1800
cccccagatg cggtcgaagt tttcggattt gaccctgcct gccttgaccg actggctgag  1860
gtaatgcact tgcctagcag tgtcatccca gctgctctgg ccgaaatgtc cggcgacccc  1920
aaccgtccgg cttccccggt cactactgtg tggactgttt cacaattctt tgcccgccac  1980
agaggaggag agcaccctga tcaggtgcgc ttaggaaaaa tcatcagcct ttgtcaagtt  2040
gttgaggaat gctgttgcca tcagaataaa accaaccggg ccaccccgga agaggttgcg  2100
gcaaggattg atcagtacct ccatggtgca acaagtcttg aagaatgctt gattaggctt  2160
gagagggttt gcccgccgag cgctgcggac accttctttg attggaatgt tgtgctccct  2220
ggggttgggg cttcaactca gacaaccaaa cagctccatg tcaaccagtg ccgcgctctg  2280
gttcctgtcg tgactcaaga gcctttggac aaagacccag tccctctgac cgccttctcg  2340
ctgtccaatt gctactatcc tgcacaaggt gacgaggttc gtcaccgtga gaggctaaac  2400
tccgtactct ctaagctgga gggggttgtt cgtgaggaat atgggctcac gccaactgga  2460
cctggcccgc gacccgcact accgaacggg ctcgtcgaac ttaaagacca gatggaggag  2520
gatctgctaa aactagtcaa cgcccaggca acttcagaaa tgatggcctg ggcagccgag  2580
caggttgatc tgaaagcttg ggtcaaaaac tacccacggt ggacaccgtc accccctcca  2640
ccaagagttc agcctcgaaa acaaagcct gtcaagagct gccagggaa caaacctgtc   2700
cccgctccac gcaggaaggt cagatctgat tgtggcagcc cgatttcgat gggcgacaat  2760
gttcctgacg tcgggaaga tttgactgtt ggtggccccc ttgatctttc gacaccatcc   2820
gagccgatga cacctctgag tgagcctgca cctatgcccg cgttgcaata tatttctagg  2880
ccagtgacac ctttgagtgt gctggcccca gtacctgcac cgcgtagaac tgtgtcccga  2940
ccggtgacgc ccttgagtga gccaattttt gtgtctgcac cgcgacacaa atttcagcag  3000
gtggaagaag cgaatctggc ggcaacaatg ctgacgcacc aggacgaacc tctagatttg  3060
tctgcatcct cacagactga atatgaggct tctcccctaa caccactgca gaacatgggt  3120
attctggagg tggggggca agaagctgag gaagttctga gtgaaaactc ggatacactg  3180
aatgacatca accctgcacc tgtgtcatca agcagctccc tgtcaagtgt taagatcaca  3240
cgcccaaaac actctgctca agccatcatt gactcgggcg ggccctgcag tgggcatctc  3300
cgaaagggaa aagaagcatg cctcagcatc atgcgtgagg cttgtgatgc ggctaagctt  3360
agtgaccctg ccacgcagga atggctttct cgcatgtggg atagggttga tatgctgact  3420
tggcgcaaca cgtctgctta ccaggcgttc cgcatcttag atggtaggtt tgagtttctc  3480
ccaaagatga tactcgagac accgccgccc taccgtgtg gtttgtgat gctgcctcgc   3540
acgcctgcac cttccgtggg tgcagagagt gaccttacca ttggttcagt cgccactgaa  3600
gatgttccac gcatcctcgg gaaaatagaa aacgccggca agatgcccaa ccaggggctc  3660
ttgacatcct tcgggaaga accggtgtgc gaccaacctg tcaaggactc ctggatgtcg  3720
tcgcgggggt ttgacgagag cacaacggct ccgtccgctg gtacaggtgg tgctgactta  3780
cccaccgatt tgccacctc agatggtttg gatgcggacg agtgggggcc gttacggacg  3840
```

```
gtaagaaaga aagctgaaag gctcttcgac caattgagcc gtcaggtttt taacctcgtc    3900
tcccatctcc ctgttttctt ctcacacctc ttcaaatctg acagtggtta ttctccgggt    3960
gattggggtt ttgcagcttt tactttattt tgcctctttt tgtgttacag ctacccattc    4020
tttggttttg ttcccctctt gggtgttttt tctgggtctt ctcggcgtgt gcgcatgggg    4080
gttttttggct gttggttggc ttttgctgtt ggcctgttca agcctgtgtc cgacccagtc   4140
ggcactgctt gtgagtttga ctcgccagag tgtaggaacg tccttcattc ttttgagctt    4200
ctcaaacctt gggaccctgt tcgcagcctt gttgtgggcc ccgtcggtct cggccttgcc    4260
attcttggca ggtactgggc ggggcacgc tacatctggc attttttgct taggcttggc     4320
attgttgcag attgtatctt ggctggagct tatgtgcttt ctcaaggtag gtgtaaaaag    4380
tgctggggat cttgtgtaag aactgctcct aatgaaatcg ccttcaacgt gttccctttt    4440
acgcgtgcga ccaggtcgtc actcatcgac ctgtgcgatc ggttttgtgc gccaaaaggc    4500
atggaccccca ttttcctcgc tactgggtgg cgcgggtgct ggaacggccg aagtcccatt   4560
gagcaaccct ctgaaaaacc catcgcgttc gcccagttgg atgaaaagag gatcacggct    4620
agaactgtgg tcgctcagcc ttatgatcct aaccaagccg taaagtgctt gcgggtgtta    4680
caggcgggtg gggcgatagt ggccgaggca gtcccaaaag tggtcaaggt ttccgctatt    4740
ccattccgag ctccctttt tcccaccgga gtgaaggttg atcctgagtg caggatcgtg     4800
gtcgaccccg acacttttac tacagctctc cggtctggtt actccaccac aaacctcgtc    4860
cttggtgtag gggactttgc ccaactgaat ggattaaaaa tcaggcaaat ttccaagccc    4920
tcgggaggag gcccgcacct cattgctgcc ctgcatgttg cttgctcgat ggcgttgcac    4980
atgcttgctg gagtttatgt aactgcagtg gggtcttgcg gtaccggcac caacgatccg    5040
tggtgcacta acccattcgc cgtccctggc tacggacctg gctccctctg cacgtccaga    5100
ttgtgcatct cccaacatgg ccttaccctg cccttgacag cacttgtggc aggattcggt    5160
cttcaggaaa ttgccctagt cgttttgatt ttcgtttcca tcggaggcat ggctcatagg    5220
ttgagttgta aggctgatat gctgtgcgtc ttacttgcaa tcgccagcta tgtttgggta    5280
ccccttacct ggttgctctg tgtgtttcct tgctggttgc gctggttctc tttgcaccct    5340
ctcaccattc tatggttggt gttttttcttg atgtctgtaa atatgccttc gggaatctta    5400
accgtggtgt tattggttgc tctttggctt ctaggccgtt atactaatgt tgttggtctt    5460
gttacccct atgatattca ccattacacc aatggccccc gcggtgttgc cgccttggct    5520
accgcaccag atgggactta cttggccgct gtccgccgcg ctgcgttgac tggccgcacc    5580
gtgctgttta ccccgtctca gcttgggtcc cttcttgagg gcgctttcag aactcgaaag    5640
ccctcactga acaccgtcaa tgtggtcggg tcctccatgg gctctggcgg agtgttcact    5700
atcgatggga aaattaagtg cgtgactgcc gcacatgtcc ttacgggtaa ttcagccagg    5760
gtttccgggg tcggctttaa tcaaatgctt gactttgatg taaaggggga cttcgccata    5820
gctgactgcc cgaattggca agggctgct cctaagaccc aattctgcga ggatggatgg    5880
actgccgcg cctattggct gacatcctct ggcgtcgaac ccggtgtcat tgggaatgga    5940
ttcgccttct gcttcaccgc gtgcggcgat tccgggtccc cagtgatcac cgaagccggt    6000
gagcttgtcg gcgttcacac aggatcaaac aaacaaggag gaggcattgt tacgcgcccc    6060
tctggccagt tttgcaatgt ggcacccatc aagctgagcg aattaagtga gttctttgct    6120
ggacctaagg tcccgctcgg tgatgtgaag gttggcagcc acataattaa agacatatgc    6180
gaggtacctt cagatctttg cgccttgctt gctgccaaac ccgaactgga aggaggcctc    6240
```

-continued

```
tccaccgtcc aacttctgtg tgtgtttttc ctcctgtgga gaatgatggg acatgcctgg    6300
acgcccttgg ttgctgttgg ttttttatc ttgaatgagg ttctcccagc tgtactggtc     6360
cggagtgttt tctcctttgg aatgtttgtg ctatcttggc tcacaccatg gtctgcgcaa    6420
gttctgatga tcaggcttct aacagcagct cttaacagga acagattgtc actcgccttt    6480
tacagccttg gtgcagcgac cggttttgtc gcagatctgg cggcaactca agggcacccg    6540
ttgcaggcag taatgaattt aagtacctat gccttcctgc ctcggataat ggtcgtgacc    6600
tcaccagtcc cagtgattgc gtgtggtgtt gtgcacctcc ttgccataat tttgtacttg    6660
tttaagtacc gctgcctgca caatgtcctt gttggcgatg gtgcgttctc tgcggctttc    6720
ttcttgcgat actttgccga ggggaaattg agggaagggg tgtcgcaatc ctgcgggatg    6780
aatcatgagt cgctgactgg tgccctcgct atgagactta atgacgagga cttggatttt    6840
cttacgaaat ggactgattt taagtgtttt gtttctgcat ccaacatgag gaatgcggcg    6900
ggccagttca tcgaggctgc ctatgctaaa gcacttagaa ttgaacttgc ccagttggtg    6960
caggttgata aggttcgagg tactttggcc aaacttgaag cttttgctga taccgtggca    7020
ccccaactct cgcccggtga cattgttgtt gctcttggcc atacgcctgt tggcggtatc    7080
ttcgacctaa aggttggtag caccaagcat accctccaag ccattgagac cagagttctt    7140
gccgggtcca aaatgaccgt ggcgcgtgtc gttgatccaa cccccacacc cccacccgca    7200
cccgtgccta tccccttcc accgaaagtt ctggagaatg gtcccaacgc ctgggggat     7260 gaggatcgtt tgaataagaa gaagaggcgc aagatggaag ccgtcggcat ctttgttatg    7320
ggtggaaaga aatatcagaa attttgggac aagaactccg gtgatgtgtt ttatgaggag    7380
gtccatgata cacagacgc gtgggagtgc ctcagagttg acaaccctgc cgactttgac     7440
cctgagaagg gaactctgtg cggcatact accattgaag ataagactta cagtgtctac     7500
gcctccccat ctggcaagaa attcctggtc ccgcctacc cagagagcaa aaaaaaccaa     7560
tgggaagctg cgaagctttc cgtggaacag gcccttggca tgatgaatgt cgacggtgaa    7620
ctgacagcca agaagtgga gaaactgaaa agaataattg acaaactcca gggcctgact    7680
aaggagcagt gtttaaactg ctagccgcca gcggcttgac ccgctgtggt cgcggcggct    7740
tggttattac tgagacagcg gtaaaaatag tcaaatttca caaccggacc ttcacccctag   7800 gacctgtgaa tttaaaagtg gccagtgagg ttgagctaaa agacgcggtc gagcataacc    7860 aacaccggt tgcaagaccg gttgatggtg gtgttgtgct cctgcgctcc gcagttcctt     7920
cgcttataga cgtcttaatc tccggcgctg atgcatctcc caagttactc gcccgccacg    7980
ggccgggaaa cactgggatc gatggcacgc tttgggattt tgaggccgag gccactaaag    8040
aggaaattgc actcagtgcg caaataatac aggcttgtga cattaggcgc ggcgacgcac    8100
ctgaaattgg tcttccttat aagctgtacc ctgtcagggg caaccctgag cgggtaaaag    8160 gagtttttaca gaatacaagg tttggagata taccttataa aacccccagt gacactggaa    8220
gcccagtgca cgcggctgcc tgcctcacgc ccaatgccac tccggtgact gatgggcgct    8280
ccgtcttggc cacgactatg ccctccggtt ttgagttgta tgtaccgacc attccagcgt    8340
ctgtccttga ttatcttgat tctaggcctg actgccccaa acagttgaca gagcacggct    8400
gtgaggacgc cgcattaaga gacctctcca agtatgactt gtccacccaa ggctttgttt    8460
tacctggagt tcttcgcctt gtgcgtaagt acctgtttgc tcatgtgggt aagtgcccgc    8520
ccgttcatcg gccttccact taccctgcca agaattctat ggctggaata aatgggaaca    8580
ggtttccaac caaggacatc cagagcgtcc ctgaaatcga cgttctgtgc gcacaggccg    8640
```

```
ttcgggaaaa ctggcaaact gttacccctt gtaccctcaa gaaacagtat tgtgggaaga    8700
agaagactag gacaatactc ggcaccaata acttcattgc gctggctcac cgggcagcgt    8760
tgagtggtgt cacccagggc ttcatgaaaa aggcgtttaa ctcgcccatt gccctcggta    8820
aaaacaaatt taaagagctt cagactccgg tcttaggcag gtgccttgaa gctgatcttg    8880
catcctgcga tcgctccaca cctgcaattg tccgctggtt tgccgccaat cttctttatg    8940
aacttgcctg tgctgaagag caccagccgt cgtacgtgtt gaactgctgc cacgacctac    9000
tggtcacgca gtccggcgca gtaactaaga gaggtggcct gtcgtctggc gacccgatca    9060
cttctgtgtc caacaccatt tacagcttgg tgatatatgc acaacacatg gtgctcagtt    9120
actttaaaag tggtcaccct catggccttc tgtttctaca agaccagctg aagtttgagg    9180
acatgctcaa ggttcaaccc ctgatcgtct attcggacga cctcgtactg tatgccgagt    9240
ctcccaccat gccaaactac cactggtggg ttgaacatct gaacctgatg ctgggttttc    9300
agacggaccc aaagaagaca gccataacag actcgccatc atttctaggc tgtaggataa    9360
taaatggacg ccagctcgtc cctaaccgtg acaggattct cgcggccctc gcctaccata    9420
tgaaggcaag caatgtctct gaatactacg cctcggcggc tgcgatactc atggacagct    9480
gtgcttgttt agagtatgat cccgaatggt ttgaagagct tgtagttggg atagcgcagt    9540
gtgcccgcaa ggacggctac agttttcccg gcccgccgtt cttcttgtcc atgtgggaaa    9600
aactcagatc caatcatgag gggaagaagt ccagaatgtg cgggtactgc ggggccccgg    9660
ctccgtacgc cactgcctgt ggcctcgacg tctgtattta ccacacccac ttccaccagc    9720
attgtccagt catcatctgg tgtggccacc cggctggttc tggttcttgt agtgagtgca    9780 aacccccccct agggaaaggc acaagccctc tagatgaggt gttagaacaa gtcccgtata    9840
agcctccacg gactgtaatc atgcatgtgg agcagggtct caccccctctt gacccaggca    9900 gataccagac tcgccgcgga ttagtctccg ttaggcgtgg cattagagga atgaggttg    9960 atctaccaga cggtgattat gctagcaccg ccctactccc tacttgtaaa gagattaaca    10020
tggtcgctgt cgcctctaat gtgttgcgca gcaggttcat catcggcccg cctggtgctg    10080
ggaaaacata ctggctcctt caacaggtcc aggatggtga tgccatttac acgccaactc    10140
accagaccat gctcgatatg attagggctt tggggacgtg ccggttcaac gtcccagcag    10200
gtacgacgct gcaattccct gccccctccc gtaccggccc ttgggttcgc atcctagccg    10260
gcggttggtg tcctggcaag aattccttcc tggatgaagc agcgtattgt aatcaccttg    10320
atgtcttgag gcttcttagc aaaactaccc tcacctgtct gggagatttc aaacaactcc    10380
acccagtggg ttttgattct cattgctatg ttttttgacat catgcctcag actcaactga    10440
agaccatctg gagatttgga cagaatatct gtgaggccat tcagccagat tacagggaca    10500
aacttgtatc catggtcaac acaacccgtg taacctacgt ggaaaaacct gtcaagtatg    10560
ggcaagtcct cacccccttac cacagggacc gagaggacgg cgccatcaca attgactcca    10620
gtcaaggcgc cacatttgat gtggttacac tgcatttgcc cactaaagat tcactcaaca    10680
ggcaaagagc ccttgttgct attaccaggg caagacatgc tgtctttgtg tatgacccac    10740
acaggcaact gcagagcatg tttgatcttc ctgcgaaagg cacacccgtc aacctcgctg    10800
tgcaccgtga cgagcagctg atcgtgctag atagaaataa caagaatgc acggttgctc    10860 aggctctagg caatggggat aaattcaggg ccacagacaa gcgcgttgta gattctctcc    10920
gcgccatttg tgcagatctg gaagggtcga gctcccgct cccaaggtc gcacacaact    10980 tgggatttta tttctcgcct gatttgacac agtttgctaa actcccggta gaacttgcac    11040
```

```
cccactggcc cgtggtgaca acccagaaca atgaaaagtg gccagaccgg ttggttgcta    11100
gccttcgccc cgtccataag tatagccgcg cgtgcatcgg tgccggctac atggtgggcc    11160
cctcagtgtt tctgggcacc cctggggttg tgtcatacta tctcacaaaa tttgtcaggg    11220
gcgaggctca aatgcttccg gagacagtct tcagcaccgg ccgaattgag gtagattgcc    11280
gtgagtatct cgatgaccgg gagcgagaaa ttgctgagtc cctcccccat gctttcattg    11340
gcgacgtcaa aggcactacc gttggaggat gtcaccatgt cacctccaaa taccttccgc    11400
gcttccttcc caaggaatca gtcgcggtag tcggggtttc aagcccgggg aaagccgcaa    11460
aagcagtttg cacattaaca gatgtgtatc tcccagatct cgaagcttac ctccacccag    11520
agacccagtc caagtgctgg aaaatgatgt tggacttcaa ggaagttcga ctgatggtct    11580
ggaaggacaa gacggcctat tttcaacttg aaggccgcca tttcacctgg taccagcttg    11640
caagctatgc ctcgtacatc cgagttcctg ttaactctac ggtgtatttg gacccctgca    11700
tgggccctgc cctttgcaac agaagagttg tcgggtccac tcattgggga gctgacctcg    11760
cagtcacccc ttatgattac ggtgccaaaa tcatcctgtc tagtgcatac catggtgaaa    11820
tgcccctgg gtacaaaatc ctggcgtgcg cggagttctc gcttgacgat ccagtgaggt    11880
acaaacacac ctgggggttt gaatcggata cagcgtatct gtacgagttc accggaaacg    11940
gtgaggactg ggaggattac aatgatgcgt tcgtgcgcg ccagaaaggg aaaatttata    12000
aggccactgc caccagcatg aggtttcatt tcccccgggg ccctgtcatt gaaccaactt    12060
taggcctgaa ttgaaatgaa atggggtcca tgcaaagcct ctttgacaaa attggccaac    12120
ttttcgtgga tgctttcacg gaattttttgg tgtccattgt tgatatcatc atatttttgg    12180
ccattttgtt tggctttacc atcgctggct ggctggtggt cttctgcatc cgattggttt    12240
gctccgcggt actccgtgcg cgccctacca ttcaccctga gcaattacag aagatcctat    12300
gaggcctttc tttctcagtg ccaggtggat attcccacct ggggaactag acatcccctg    12360
gggatgcttt ggcaccataa ggtgtcaacc ctgattgatg aaatggtgtc gcgtcggatg    12420
taccgcacca tggaaaaagc aggacaggct gcctggaaac aggtggtgag cgaggccacg    12480
ctgtctcgca ttagtggttt ggatgtggtg gctcattttc agcatcttgc cgccattgaa    12540
gccgagacct gtaaatattt ggcctctcgg ctgcccatgc tacacaatct gcgcatgaca    12600
gggtcaaatg taaccatagt gtataatagt actttgaatc aggtgtttgc tattttttcca    12660
accccctggat cccggccaaa gcttcatgat tttcagcaat ggctaatagc tgtgcactcc    12720
tccatatttt cctccgttgc ggcttcttgt actctttttg ttgtgctgtg gttgcggatt    12780
ccaatgctac gtactgtttt tggtttccgc tggttagggg caattttttcc ttcgaactca    12840
cggtgaatta cacggtgtgt ccgccttgcc tcacccggca agcagccgct gaggtctacg    12900
aaccaggcag gtctctttgg tgcaggatag ggcatgaccg atgtagtgag gaagaccatg    12960
acgatctagg gttcatggtt ccgtctggcc tctccagcga aggccacttg accagtgttt    13020
acgcctggtt ggcgttcctg tccttcagct acacggccca gttccatccc gagatatttg    13080
ggatagggaa tgtgagtcaa gtttatgttg acatcaagca ccaattcatc tgcgccgttc    13140
acgacgggga gaacgccacc ttgcctcgtc atgacaatat ttcagccgta tatcagacct    13200
actaccaaca tcaagtcgac ggcggcaatt ggtttcacct agaatggctg cgccccttct    13260
tttcctcttg gttggtttta aatgtttctt ggtttctcag gcgttcgcct gcaagccatg    13320
tttcagttca agtctttcgg acatcaaaac caacacaacc gcagcatcag ctttgttgt    13380
cctccaggac atcagctgcc ttaggcatgg cgactcgtcc tctcagacga ttcgcaaaag    13440
```

```
ctctcagtgc cgcgcggcga tagggacgcc cgtgtacatc actgtcacag ccaatgtcac   13500
agatgagaat tatttacatt cttctgatct ccttatgctt tcttcttgcc ttttctatgc   13560
ttctgagatg agtgaaaagg gattcaaggt gatgtttggc aatgtgtcag gcatcgtggc   13620
tgtgtgtgtc aactttacca gctacgtcca acatgtcaag gagtttaccc aacgctcctt   13680
ggtggtcgat catgtgcggc tgctccattt catgacacct gagaccatga ggtgggcaac   13740
cgttttagcc tgttttcttg ccatcttact ggcaatttga atgttcaagt atgttgggga   13800
gatgcttgac cgcgggctgt tgctcgcgat tgctttcttt gtggtgtatc gtgccatttt   13860
gttttgctgc gctcgtcaac gccaacagca acagcagctc tcatcttcag ttaatttaca   13920
acttgacgct atgtgagctg aatggcacag attggctgaa agacaaattt gattgggcat   13980
tggagacttt tgtcatcttt cccgtgttga ctcacattgt ctcatatagt gcactcacca   14040
ctagccattt ccttgacaca gtcggtctgg ttactgtgtc tactgccggg ttctaccacg   14100
ggcggtatgt tctgagtagc atctacgcgg tctgcgctct ggccgcattg acttgcttcg   14160
tcattaggct tgcgaagaac tgcatgtcct ggcgctactc ttgtaccaga tatactaact   14220
tccttctgga cactaagggc agactctatc gctggcggtc gcccgttatc atagagaaag   14280
ggggtaaggt tgaggtcgaa ggtcacctga tcgacctcaa aagagttgtg cttgatggtt   14340
ccgtggcaac ccctttatac agagtttcag cggaacaatg gggtcgtctt tagacgactt   14400
ttgctatgat agcacggctc cacaaaaggt gcttttggcg ttttccatta cctacacgcc   14460
agtgatgata tatgctctaa aggtaagtcg cggccgactt ttagggcttc tgcacctttt   14520
gatctttctg aattgtactt ttaccttcgg gtacatgaca tgcgtgcact taatagcac   14580 aaataaggtc gcgctcacta tgggagcagt agttgcactt ctttgggggg tgtactcagc   14640
catagaaacc tggaagttca tcacctccag atgtcgtttg tgcttgctag gccgcaagta   14700
cattctggcc cccgcccacc acgtcgaaag tgccgcgggc tttcatccga tcgcggcaaa   14760
tgataaccac gcatttgtcg tccggcgtcc cggctccact acggttaacg gcacattggt   14820
gcccgggttg aaaagcctcg tgttgggtgg cagaaaagct gttaaacagg gagtggtaaa   14880
ccttgtcaaa tatgccaaat aacaacggca agcagcaaaa gaaaaagagg gggaatggcc   14940
agccagtcaa tcagctgtgc cagatgctgg gtaagatcat cgcccagcaa aaccagtcca   15000
gaggcaaggg accggggaag aaaattaaga ataaaacccc ggagaagccc cattttcctc   15060
tagcgactga agatgacgtc aggcatcact tcacccctag tgagcggcaa ttgtgtctgt   15120
cgtcgatcca gactgccttt aaccaggcg ctggaacctg taccctatca gattcaggta   15180
ggataagtta cactgtggag tttagtttgc cgacgcatca tactgtgcgc ctgatccgcg   15240
tcacagcgcc atcatcagcg taatgggctg gcattcctta agcacctcag tgttagaatt   15300
ggaagaatgt gtggtgaatg gcactgattg gcactgtgcc tctaagtcac ctattcaatt   15360
agggcgaccg tgtgggggtt aagtttaatt ggcgagaacc atgcggccga aattaaaaaa   15420
aaaa                                                                15424

<210> SEQ ID NO 2
<211> LENGTH: 15424
<212> TYPE: DNA
<213> ORGANISM: Porcine reproductive and respiratory syndrome virus

<400> SEQUENCE: 2
tcgcccgggc aggtgttggc tctatgcctt ggcatttgta ttgtcaggag ctgcgaccat     60
tggtacagcc caaaactagc tgcacagaaa acgcccttct gtgacagccc tcttcagggg    120
```

```
agcttagggg tctgtcccta gcaccttgct tccggagttg cactgcttta cggtctctcc      180
aacccttta  ccatgtctgg gatacttgat cggtgcacgt gcaccccaa  tgccagggtg      240
tttatggcgg agggccaagt ctactgcaca cgatgtctca gtgcacggtc tctccttcct      300
ctgaatctcc aagttcctga gcttggagtg ctgggcctat tttacaggcc cgaagagcca      360
ctccggtgga cgttgccacg tgcattcccc actgttgagt gctcccccgc cggggcctgc      420
tggctttctg cgatctttcc aattgcacga atgaccagtg gaaacctgaa ctttcaacaa      480
agaatggtgc gggtcgcagc tgagatttac agagccggcc agctcacccc tgcagtcttg      540
aaggctctac aagtttatga acggggttgc cgctggtacc ctatagtcgg acctgtccct      600
ggagtggccg ttttgccaa  ctccctacat gtgagtgata aaccttccc  gggagcaact      660
catgtgctaa ccaacctgcc actcccgcag aggcctaagc ctgaagactt ttgcccttt       720
gagtgtgcta tggctgacgt ctatgatatt ggtcatggcg ccgtcatgta tgtggccaaa      780
gggaaagtct cctgggcccc tcgtggcggg gatgaggcga aatttgaaac tgtccctagg      840
gagttgaagt tgatcgcgaa ccaactccac atctccttcc cgccccacca cgcagtggac      900
atgtctaagt ttgtgttcat agcccctggg agtggtgtct ctatgcgggt cgagtgccca      960
cacggctgtc tccccgctaa tactgtccct gaaggtaact gctggtggcg cttgtttgac     1020
tcgctcccac tggacgttca gaacaaagaa attcgccgtg ccaaccaatt cggctatcaa     1080
accaagcatg gtgtcgctgg caagtaccta caacggaggc tgcaagctaa tggtctccga     1140
gcagtgactg atacagatgg acccattgtc gtacagtatt tctctgttag ggagagctgg     1200
atccgccact tcagactggc ggaagagcct agcctccctg ggtttgaaga cctcctcaga     1260
ataagggtag agcccaatac gtcgccattg agtgacaagg gtggaaaaat cttccggttt     1320
ggcagtcaca aatggtacgg tgctggaaag agagcaagga aagcacgctc tggtatgacc     1380
accacagtcg ctcaccgcgc cttgcccgct cgtgaaatcc agcaagccaa aaagcacgag     1440
gatgccggcg ctgataaggc tgtgcatctc aggcactatt ctccgcctgc cgacgggaac     1500
tgtggttggc actgcatttc cgccatcgcc aaccgaatgg tgaattccaa atttgaaact     1560
actcttcccg agagggtgag accttcagat gactgggcta ctgacgagga ccttgtgaac     1620
accatccaaa ttctcaagct ccctgcggcc ttggacagga acggtgcttg tgttggcgcc     1680
aaatacgtgc ttaagctgga aggcgagcat tggactgtct ctgtgaccct ggggatgtcc     1740
ccttctttgc tccccttga  atgtgttcag ggctgttgtg agcataagag cggacttggt     1800
cccccagatg cggtcgaagt tttcggattt gaccctgcct gccttgaccg actggctgag     1860
gtaatgcact tgcctagcag tgtcatccca gctgctctgg ccgaaatgtc cggcgacccc     1920
aactgtccgg cttcccggt  cactactgtg tggactgttt cacaattctt tgcccgccac     1980
agaggaggag agcaccctga tcaggtgcgc ttaggaaaaa tcatcagcct ttgtcaagtt     2040
gttgaggaat gctgttgcca tcagaataaa accaaccggg ccaccccgga agaggttgcg     2100
gcaaggattg atcagtacct ccatggtgca acaagtcttg aagaatgctt gattaggctt     2160
gagagggttt gcccgccgag cgctgcggac accttctttg attggaatgt tgtgctccct     2220
ggggttgggg cttcaactca gacaaccaaa cagctccatg tcaaccagtg ccgcgctctg     2280
gttcctgtcg tgactcaaga gccttttggac aaagactcag tccctctgac cgccttctcg     2340
ctgtccaatt gctactatcc tgcacaaggt gacgaggttc gtcaccgtga gaggctaaac     2400
tccgtactct ctaagctgga gggggttgtt cgtgaggaat atgggctcac gccaactgaa     2460
cctggcccgc gacccgcact accgaacggg ctcgtcgaac ttaaagacca gatggaggag     2520
```

-continued

```
gatctgctga aactagtcaa cgcccaggca acttcagaaa tgatggcctg ggcagccgag       2580
caggttgatc tgaaagcttg ggtcaaaaac tacccacggt ggacaccgcc accccctcca       2640
ccaagagttc agcctcgaaa acaaagtct gtcaagagct tgccagggaa caaacctgtc        2700
cccgctccac gcaggaaggt cagatctgat tgtggcagcc cgattttgat gggcgacaat      2760
gttcctgacg gtcgggaaga tttgactgtt ggtggccccc ttgatctttc gacaccatcc      2820
gagccgatga cacctctgag tgagcctgca cttatgcccg cgttgcaata tatttctagg      2880
ccagtgacat cttgagtgt gctggcccca gttcctgcac cgcgtagaac tgtgtcccga        2940
ccggtgacgc ccttgagtga gccaattttt gtgtctgcac cgcgacacaa atttcagcag      3000
gtggaagaag cgaatctggc ggcaacaacg ctgacgcacc aggacgaacc tctagatttg      3060
tctgcatcct cacagactga atatgaggct ctcccctaa caccactgca gaacatgggt        3120
attctggagg tggggggca agaagctgag gaagttctga gtgaaatctc ggatacactg       3180
aatgacatca ccctgcacc tgtgtcatca agcagctccc tgtcaagtgt taagatcaca       3240
cgcccaaaac actctgctca agccatcatt gactcgggcg ggccctgcag tgggcatctc      3300
cgaagggaaa aagaagcatg cctcagcatc atgcgtgagg cttgtgatgc ggctaagctt       3360
agtgaccctg ccacgcagga atggctttct cgcatgtggg ataggttga catgctgact         3420 tggcgcaaca cgtctgctta ccaggcgttc cgcatcttag atggtaggtt tgagtttctc      3480
ccaaagatga tactcgagac accgccgccc tacccgtgtg ggtttgtgat gctgcctcac      3540
acgcctgcac cttccgtggg tgcagagagt gaccttacca ttggttcagt cgccactgaa      3600
gatgttccac gcatcctcgg gaaaatagaa aacgccggcg agatgcccaa ccaggggctc      3660
ttgacatcct tcggggaaga accggtgtgc gaccaacctg tcaaggactc ctggatgtcg      3720 tcgcggggt ttgacgagag cacaacggct ccgtccgctg gtacaggtgg tgctgactta       3780
cccaccgatt tgccaccttc agatggtttg gatgcggacg agtgggggcc gttacggacg      3840
gtaagaaaga aagctgaaag gctcttcgac caattgagcc gtcaggtttt taacctcgtc      3900
tcccatctcc ctgttttctt ctcacacctc ttcaaatctg acagtggtta ttctccgggt      3960
gattggggtt ttgcagcttt tactttattt tgcctctttt tgtgttacag ctacccattc      4020
tttggttttg ttcccctctt gggtgttttt tctgggtctt ctcggcgtgt gcgcatgggg      4080 gttttggct gttggttggc ttttgctgtt ggcctgttca agcctgtgtc cgacccagtc       4140
ggcactgctt gtgagtttga ctcgccagag tgtaggaacg tccttcattc ttttgagctt      4200
ctcaaacctt gggaccctgt tcgcagcctt gttgtgggcc ccgtcggtct cggccttgcc      4260
attcttggca ggttactggg cggggcacgc tacatctggc attttttgct taggcttggc      4320
attgttgcag attgtatctt ggctggagct tatgtgcttt tcaaggtag gtgtaaaaag       4380 tgctggggat cttgtgtaag aactgctcct aatgaaatcg ccttcaacgt gttcccttt       4440 acgcgtgcga ccaggtcgtc actcatcgac ctgtgcgatc ggttttgtgc gccaaaaggc      4500
atggacccca ttttcctcgc tactgggtgg cgcgggtgct ggaccggccg aagtcccatt      4560
gagcaaccct ctgaaaaacc catcgcgttc gcccagttgg atgaaaagag gattacggct      4620
agaactgtgg gcgctcagcc ttatgatcct aaccaagccg taaagtgctt gcgggtgtta      4680
caggcgggtg gggcgatagt ggccgaggca gtcccaaaag tggtcaaggt ttccgctatt      4740
ccattccgag ctccctttt tcccaccgga gtgaaggttg atcctgagtg caggatcgtg       4800
gtcgaccccg acactttac tacagctctc cggtctggtt actccaccac aaacctcgtc       4860
cttggtgtgg gggactttgc ccaactgaat ggattaaaaa tcaggcaaat ttccaagccc      4920
```

```
tcgggaggag gcccgcacct cattgctgcc ctgcatgttg cttgctcgat ggcgttgcac   4980
atgcttgctg gagtttatgt aactgcagtg gggtcttgcg gtaccggcac caacgatccg   5040
tggtgcacta acccattcgc cgtccctggc tacggacctg gctccctctg cacgtccaga   5100
ttgtgcatct cccaacatgg ccttaccctg cccttgacag cacttgtggc aggattcggt   5160
cttcaggaaa ttgccctagt cgttttgatt ttcgtttcca tcggaggcat ggctcatagg   5220
ttgagttgta aggctgatat gctgtgcgtc ttacttgcaa tcgccagcta tgtttgggta   5280
ccccttacct ggttgctctg tgtgtttcct tgctggttgc gctggttctc tttgcaccct   5340
ctcaccattc tatggttggt gttttctttg atgtctgtaa atatgccttc gggaatctta   5400
accgtggtgt tattggttgc tctttggctt ctaggccgtt atactaatgt tgttggtctt   5460
gttaccccct atgatattca tcattacacc aatggccccc gcgtgttgc cgccttggct   5520 accgcaccag atgggactta cttggccgct gtccgccgcg ctgcgttgac tggccgcacc   5580
gtgctgttta ccccgtctca gcttgggtcc cttcttgagg gcgctttcag aactcgaaag   5640
ccctcactga acaccgtcaa tgtggtcggg tcctccatgg gctctggcgg agtgttcact   5700
atcgatggga aaattaagtg cgtgactgcc gcacatgtcc ttacgggtaa ttcagccagg   5760
gtttccgggg tcggcttcaa tcaaatgctt gactttgatg taaaggggga cttcgccata   5820
gctgattgcc cgaattggca aggggctgct cctaagaccc aattctgcga ggatggatgg   5880
actggccgcg cctattggct gacatcctct ggcgtcgaac ccggtgtcat gggaatggaa   5940
ttcgccttct gcttcaccgc gtgcggcgat tccgggtccc cagtgatcac cgaagccggt   6000
gagcttgtcg gcgttcacac aggatcaaac aaacaaggag gaggcattgt tacgcgcccc   6060
tctggccagt tttgcaatgt ggcacccatc aagctgagcg aattaagtga gttcttgct   6120 ggacctaagg tcccgctcgg tgatgtgaag gttggcagcc acataattaa agacatatgc   6180
gaggtacctt cagatctttg cgccttgctt gctgccaaac ccgaactgga aggaggcctc   6240
tccaccgtcc aacttctgtg tgtgtttttc ctcctgtgga gaatgatggg acatgcctgg   6300
acgcccttgg ttgctgttgg gttttttatc ttgaatgagg ttctcccagc tgtactggtc   6360
cggagtgttt tctcctttgg aatgtttgtg ctatcttggc tcacaccatg gtctgcgcaa   6420
gttctgatga tcaggcttct aacagcagct cttaacagga acagattgtc actcgccttt   6480
tacagccttg gtgcagcgac cggttttgtc gcagatctgg cggcaactca agggcacccg   6540
ttgcaggcag taatgaattt aagtacctat gccttcctgc ctcggataat ggtcgtgacc   6600
tcaccagtcc cagtgattgc gtgtggtgtt gtgcacctcc ttgccataat tttgtacttg   6660
tttaagtacc gctgcctgca caatgtcctt gttggcgatg gtgcgttctc tgcggctttc   6720
ttcttgcgat actttgccga ggggaaattg agggaagggg tgtcgcaatc ctgcgggatg   6780
aatcatgagt cgctgactgg tgccctcgct atgagactta atgacgagga cttggatttt   6840
cttacgaaat ggactgattt taagtgtttt gtttctgcat ccaacatgag gaatgcggcg   6900
ggccagttca tcgaggctgc ctatgctaaa gcacttagaa ttgaacttgc ccagttggtg   6960
caggttgata aggttcgagg tacttttggcc aaacttgaag cttttgctga taccgtggca   7020
ccccaactct cgcccggtga cattgttgtt gctcttggcc atacgcctgt tggcggtatc   7080
ttcgacctaa aggttggtag caccaagcat accctccaag ccattgagac cagagttctt   7140
gccgggtcca aaatgaccgt ggcgcgtgtc gttgatccaa ccccacacc cccacccgca   7200 cccgtgccta tccccttcc accgaaagtt ctggagaatg gtcccaacgc ctgggggat   7260 gaggatcgtt tgaataagaa gaagaggcgc aggatggaag ccgtcggcat ctttgttatg   7320
```

```
ggtggaaaga aatatcagaa attttgggac aagaactccg gtgatgtgtt ttatgaggag    7380
gtccatgata acacagacgc gtgggagtgc ctcagagttg acaaccctgc cgactttgac    7440
cctgagaagg gaactctgtg cgggcatact accattgaag ataagactta cagtgtctac    7500
gcctccccat ctggcaagaa attcctggtc cccgtctacc cagagagcaa aaaaaaccaa    7560
tgggaagctg cgaagctttc cgtggaacag gcccttggca tgatgaatgt cgacggtgaa    7620
ctgacagcca aagaagtgga gaaactgaaa agaataattg acaaactcca gggcctgact    7680
aaggagcagt gtttaaactg ctagccgcca gcggcttgac ccgctgtggt cgcggcggct    7740
tggttgttac tgagacagcg gtaaaaatag tcaaatttca caaccggacc ttcaccctag    7800
gacctgtgaa tttaaaagtg gccagtgagg ttgagctaaa agacgcggtc gagcataacc    7860
aacacccggt tgcaagaccg gttgatggtg gtgttgtgct cctgcgctcc gcagttcctt    7920
cgcttataga cgtcttaatc tccggcgctg atgcatctcc caagttactc gcccgccacg    7980
ggccgggaaa cactgggatc gatggcacgc tttgggattt tgaggccgag gccactaaag    8040
aggaaattgc actcagtgcg caaataatac aggcttgtga cattaggcgc ggcgacgcac    8100
ctgaaattgg tcttccttat aagctgtacc ctgtcagggg caaccctgag cgggtaaaag    8160
gagttttaca gaatacaagg tttggagaca taccttataa aacccccagt gacactggaa    8220
gcccagtgca cgcggctgcc tgcctcacgc ccaatgccac tccggtgact gatgggcgct    8280
ccgtcttggc cacgactatg ccctccggtt ttgagttgta tgtaccgacc attccagcgt    8340
ctgtccttga ttatcttgat tctaggcctg actgccccaa acagttgaca gagcacggct    8400
gtgaggacgc cgcattaaga gacctctcca agtatgactt gtccacccaa ggctttgttt    8460
tacctggagt tcttcgcctt gtgcgtaagt acctgttttgc tcatgtgggt aagtgcccgc    8520
ccgttcatcg gccttccact tacccctgcca agaattctat ggctggaata aatgggaaca    8580
ggtttccaac caaggacatc cagagcgtcc ctgaaatcga cgttctgtgc gcacaggccg    8640
tgcgggaaaa ctggcaaact gttacccctt gtaccctcaa gaaacagtat tgtgggaaga    8700
agaagactag gacaatactc ggcaccaata acttcattgc gctggcccac cgggcagcgt    8760
tgagtggtgt cacccagggc ttcatgaaaa aggcgtttaa ctcgcccatt gccctcggta    8820
aaaacaaatt taaagagctt cagactccgg tcttaggcag gtgccttgaa gctgatcttg    8880
catcctgcga tcgctccaca cctgcaattg tccgctggtt tgccgccaat cttctttatg    8940
aacttgcctg tgctgaagag cacctgccgt cgtacgtgtt gaactgctgc cacgacctac    9000
tggtcacgca gtccggcgca gtaactaaga gaggtggcct gtcgtctggc gacccgatca    9060
cttctgtgtc caacaccatt tacagcttgg tgatatatgc acaacacatg gtgctcagtt    9120
actttaaaag tggtcaccct catggccttc tgtttctaca agaccagctg aagtttgagg    9180
acatgctcaa ggttcaaccc ctgatcgtct attcggacga cctcgtactg tatgccgagt    9240
ctcccaccat gccaaactac cactggtggg ttgaacatct gaacctgatg ctgggttttc    9300
agacggaccc aaagaagaca gccataacag actcgccatc atttctaggc tgtaggataa    9360
taaatggacg ccagctcgtc cctaaccgtg acaggattct cgcggccctc gcctaccata    9420
tgaaggcaag caatgtctct gaatactacg cctcggcggc tgcgatactc atggacagct    9480
gtgcttgttt agagtatgat cccgaatggt ttgaagagct tgtagttggg atagcgcagt    9540
gtgcccgcaa ggacggctac agttttcccg gcccgccgtt cttcttgtcc atgtgggaaa    9600
aactcagatc caatcatgag gggaagaagt ccagaatgtg cgggtactgc ggggcccgg    9660
ctccgtacgc cactgcctgt ggcctcgacg tctgtattta ccacacccac ttccaccagc    9720
```

```
attgtccagt catcatctgg tgtggccacc cggctggttc tggttcttgt agtgagtgca    9780
aaccccccct agggaaaggc acaagccctc tagatgaggt gttagaacaa gtcccgtata    9840
agcctccacg gactgtaatc atgcatgtgg agcagggtct caccctctt gacccaggca    9900
gataccagac tcgccgcgga ttagtctccg ttaggcgtgg cattagagga aatgaggttg    9960
atctaccaga cggtgattat gctagcaccg ccctactccc tacttgtaaa gagattaaca   10020
tggtcgctgt cgcctctaat gtgttgcgca gcaggttcat catcggcccg cctggtgctg   10080
ggaaaacata ctggctcctt caacaggtcc aggatggtga tgtcatttac acgccaactc   10140
accagaccat gctcgatatg attagggctt tggggacgtg ccggttcaac gtcccagcag   10200
gtacgacgct gcaattccct gcccctccc gtaccggccc ttgggttcgc atcctagccg    10260
gcggttggtg tcctggcaag aattccttcc tggatgaagc agcgtattgt aatcaccttg   10320
atgtcttgag gcttcttagc aaaactaccc tcacctgtct gggagatttc aaacaactcc   10380
acccagtggg ttttgattct cattgctatg tttttgacat catgcctcag actcaactga   10440
agaccatctg gagatttgga cagaatatct gtgatgccat tcagccagat tacagggaca   10500
aacttgtatc catggtcaac acaacccgtg taacctacgt ggaaaaacct gtcaagtatg   10560
ggcaagtcct cacccttac cacagggacc gagaggacgg cgccatcaca attgactcca    10620
gtcaaggcgc cacatttgat gtggttacac tgcatttgcc cactaaagat tcactcaaca   10680
ggcaaagagc ccttgttgct attaccaggg caagacatgc tatctttgtg tatgacccac   10740
acaggcaact gcagagcatg tttgatcttc ctgcgaaagg cacacccgtc aacctcgctg   10800
tgcaccgtga cgagcagctg atcgtgctag atagaaataa caaagaatgc acggttgctc   10860
aggctctagg caatggggat aaattcaggg ccacagacaa gcgcgttgta gattctctcc   10920
gcgccatttg tgcagatctg gaagggtcga gctccccgct ccccaaggtc gcacacaact   10980
tgggatttta tttctcgcct gatttgacac agtttgctaa actcccggta gaacttgcac   11040
cccactggcc cgtggtgaca acccagaaca atgaaaagtg ccagaccgg ttggttgcta    11100
gccttcgccc cgtccataag tatagccgcg cgtgcatcgg tgccggctac atggtgggcc   11160
cctcagtgtt tctgggcacc cctggggttg tgtcatacta tctcacaaaa tttgtcaggg   11220
gcgaggctca aatgcttccg gagacagtct tcagcaccgg ccgaattgag gtagattgcc   11280
gtgagtatct tgatgaccgg gagcgagaaa ttgctgagtc cctcccccat gctttcattg   11340
gcgacgtcaa aggcactacc gttggaggat gtcaccatgt cacctccaaa taccttccgc   11400
gcttccttcc caaggaatca gtcgcggtag tcggggtttc aagcccgggg aaagccgcaa   11460
aagcagtttg cacattaaca gatgtgtatc tcccagatct cgaagcttac ctccacccag   11520
agacccagtc caagtgctgg aaaatgatgt tggacttcaa ggaagttcga ctgatggtct   11580
ggaaggacaa gacggcctat tttcaacttg aaggccgcca tttcacctgg taccagcttg   11640
caagctatgc ctcgtacatc cgagttcctg ttaactctac ggtgtatttg gacccctgca   11700
tgggccctgc cctttgcaac agaagagttg tcgggtccac tcattgggga gctgacctcg   11760
cagtcacccc ttatgattac ggtgccaaaa tcatcctgtc tagtgcatac catggtgaaa   11820
tgccccctgg gtacaaaatc ctggcgtgcg cggagttctc gcttgacgat ccagtgaggt   11880
acaaacacac ctgggggttt gaatcggata cagcgtatct gtacgagttc accggaaacg   11940
gtgaggactg ggaggattac aatgatgcgt ttcgtgcgcg ccagaaaggg aaaatttata   12000
aggccactgc caccagcatg aggtttcatt ttccccgggg ccctgtcatt gaaccaactt   12060
taggcctgaa ttgaaatgaa atggggtcca tgcaaagcct ctttgacaaa attggccaac   12120
```

```
tttttgtgga tgctttcacg gaattttttgg tgtccattgt tgatatcatc atatttttgg    12180
ccattttgtt tggctttacc atcgctggct ggctggtggt cttctgcatc cgattggttt    12240
gctccgcggt actccgtgcg cgccctacca ttcaccctga gcaattacag aagatcctat    12300
gaggcctttc tttctcagtg ccaggtggat attcccacct ggggaactag acatcccctg    12360
gggatgtttt ggcaccataa ggtgtcaacc ctgattgatg aaatggtgtc gcgtcggatg    12420
taccgcacca tggaaaaagc aggacaggct gcctggaaac aggtggtgag cgaggccacg    12480
ctgtctcgca ttagtggttt ggatgtggtg gctcattttc agcatcttgc cgccattgaa    12540
gccgagacct gtaaatattt ggcctctcgg ctgcccatgc tacacaatct gcgcatgaca    12600
gggtcaaatg taaccatagt gtataatagt actttgaatc aggtgtttgc tattttttca    12660
acccctggat cccggccaaa gcttcatgat tttcagcaat ggctaatagc tgtgcactcc    12720
tccatatttt cctccgttgc ggcttcttgt actctttttg ttgtgctgtg gttgcggatt    12780
ccaatactac gtactgtttt tggtttccgc tggttagggg caattttttcc ttcgaactca    12840
cggtgaatta cacggtgtgt ccgccttgcc tcacccggca agcagccgct gaggtctacg    12900
aaccaggcag gtctctttgg tgcaggatag ggcatgaccg atgtagtgag gacgaccatg    12960
acgatctagg gttcatggtt ccgcctggcc tctccagcga aggccacttg accagtgttt    13020
acgcctggtt ggcgttcctg tccttcagct acacggccca gttccatccc gagatatttg    13080
ggatagggaa tgtgagtcaa gtttatgttg acatcaagca ccaattcatc tgcgccgttc    13140
acgacgggga gaacgccacc ttgcctcgtc atgacaatat ttcagccgta tttcagacct    13200
actaccaaca tcaagtcgac ggcggcaatt ggtttcacct agaatggctg cgccccttct    13260
tttcctcttg gttggtttta aatgtttctt ggtttctcag gcgttcgcct gcaagccatg    13320
tttcagttca agtctttcgg acatcaaaac caacactacc gcagcatcag gctttgttgt    13380
cctccaggac atcagctgcc ttaggcatgg cgactcgtcc tctcagacga ttcgcaaaag    13440
ctctcagtgc cgcgcggcga tagggacgcc cgtgtacatc actgtcacag ccaatgtcac    13500
agatgagaat tatttacatt cttctgatct ccttatgctt tcttcttgcc ttttctatgc    13560
ttctgagatg agtgaaaagg gattcaaggt gatatttggc aatgtgtcag gcatcgtggc    13620
tgtgtgtgtc aactttacca gctacgtcca acatgtcaag gagtttaccc aacgctcctt    13680
ggtggtcgat catgtgcggc tgctccattt catgacacct gagaccatga ggtgggcaac    13740
cgttttagcc tgttttttttg ccatcttact ggcaatttga atgttcaagt atgttgggga    13800
gatgcttgac cgcgggctgt tgctcgcgat tgctttcttt gtggtgtatc gtgccatttt    13860
gttttgctgc gctcgtcaac gccaacagca acagcagctc tcatcttcag ttgatttaca    13920
acttgacgct atgtgagctg aatggcacag attggctgaa agacaaattt gattgggcag    13980
tggagacttt tgtcatcttt cccgtgttga ctcacattgt ctcatatggt gcactcacca    14040
ctagccattt ccttgacaca gtcggtctgg ttactgtgtc taccgccggg ttctaccacg    14100
ggcggtatgt tctgagtagc atctacgcgg tctgcgctct ggccgcattg atttgcttcg    14160
tcattaggct tgcgaagaac tgcatgtcct ggcgctactc ttgtaccaga tatactaact    14220
tccttctgga cactaagggc agactctatc gctggcggtc gcccgttatc atagagaaag    14280
ggggtaaggt tgaggtcgaa ggtcacctga tcgacctcaa aagagttgtg cttgatggtt    14340
ccgtggcaac ccctttaacc agagtttcag cggaacaatg gggtcgtctt tagacgactt    14400
ttgctatgat agcacggctc cacaaaaggt gcttttggcg ttttccatta cctacacgcc    14460
agtgatgata tatgctctaa aggtaagtcg cggccgactt ttagggcttc tgcacctttt    14520
```

```
gatctttctg aattgtactt ttaccttcgg gtacatgaca ttcgtgcact ttaatagcac    14580
aaataaggtc gcgctcacta tgggagcagt agttgcactt ctttgggggg tgtactcagc    14640
catagaaacc tggaagttca tcacctccag atgccgtttg tgcttgctag ccgcaagta    14700
cattctggcc cccgcccacc acgtcgaaag tgccgcgggc tttcatccga tcgcggcaaa    14760
tgataaccac gcatttgtcg tccggcgtcc cggctccact acggttaacg gcacattggt    14820
gcccggggttg aaaagcctcg tgttgggtgg cagaaaagct gttaaacagg gagtggtaaa    14880
ccttgtcaaa tatgccaaat aacaacggca agcagcaaaa gaaaagagg gggaatggcc    14940
agccagtcaa tcagctgtgc cagatgctgg gtaagatcat cgcccagcaa aaccagtcca    15000
gaggcaaggg accggggaag aaaattaaga ataaaaaccc ggagaagccc catttttcctc    15060
tagcgactga agatgacgtc aggcatcact tcacccctag tgagcggcaa ttgtgtctgt    15120
cgtcgatcca gactgccttt aaccagggcg ctggaacctg taccctatca gattcaggta    15180
ggataagtta cactgtggag tttagtttgc cgacgcatca tactgtgcgc ctgatccgcg    15240
tcacagcgcc atcatcagcg taatgggctg gcattcctta agcacctcag tgttagaatt    15300
ggaagaatgt gtggtgaatg gcactgattg gcactgtgcc tctaagtcac ctattcaatt    15360
agggcgaccg tgtgggggtt aagtttaatt ggcgagaacc atgcggccga aattaaaaaa    15420
aaaa                                                                 15424

<210> SEQ ID NO 3
<211> LENGTH: 15413
<212> TYPE: RNA
<213> ORGANISM: Porcine reproductive and respiratory syndrome virus

<400> SEQUENCE: 3
augacguaua ggguguuggcu cuaugccuug gcauuuguau ugucaggagc ugcgaccauu       60
ggcacagccc aaaacuagcu gcacagaaaa cgcccuucug ugacagcccu cuucagggga      120
gcuuaggggu cuguccccuag caccuugcuu ccggagguugc acugcuuuac ggucucucca      180
acccuuuaac caugucuggg auacuugauc ggugcacgug cacccccaau gccagggugu      240
uuauggcgga gggccaaguc uacugcacac gaugucucag ugcacggucu cuccuuccuc      300
ugaaucucca aguccugag cuuggagugc uggggccuauu uuacaggccc gaagagccac      360
uccgguggac guugccacgu gcauucccca cuguugagug cuccccgccc ggggccugcu      420
ggcuuucugc gaucuuucca auugcacgaa ugaccagugg aaaccugaac uuucaacaaa      480
gaauggugcg ggcgcagcu gagauuuaca gagccggcca gcucacccu gcagucuuga      540
aggcucuaca aguuuaugaa cgggguugcc gcugguaccc uauagucgga ccuguccug      600
gaguggccga uuuugccaac ucccuacaug ugagugauaa accuuucccg ggagcaacuc      660
augugcuaac caaccugcca cucccagaga ggccuaagcc ugaagacuuu ugcccuucug      720
agugugcuau ggcugacguc uaugauauug ccauggcgc cgucauguau uggccaaag      780
ggaaagucuc cuggggccccu cguggcgggg augaggcgaa auuugaaccu gucccuaggg      840
aguugaaguu gaucgcgaac caacuccaca ucuccuuccc gccccaccac gcaguggaca      900
ugucuaaguu uguguucaua gcccugggga ugguguucuc uaugcggguc gagugcccac      960
acggcugucu cccgcuaau acugucccug aagguaacug cuggugggcgc uuguuugacu     1020
cgcucccacu ggacguucag aacaaagaaa uucgccgugc caaccaauuc ggcuaucaaa     1080
ccaagcaugg ugucgcuggc aaguaccuac acggaggcu gcaagcuaau ggucuccgag     1140
caguggacuga uacagaugga cccauugucg uacaguauuu cucuguuagg gagagcugga     1200
```

```
uccgccacuu cagacuggcg aagagccua gccucccugg guuugaagac cuccucagaa    1260 uaagggaga  gcccaauacg ucgccauuga gugacaaggg uggaaaaauc uuccgguuug    1320
gcagucacaa augguacggu gcuggaaaga gagcaaggaa agcacgcucu gguaugacca    1380
ccacagucgc ucaccgcgcc uugcccgcuc gugaaaucca gcaagccaaa aagcacgagg    1440
augccggcgc ugauaaggcu gugcaucuca ggcacuauuc uccgccugcc gacgggaacu    1500 guggguuggca cugcauuucc gccaucgcca accgaauggu gaauuccaaa uuugaaacua    1560
cucuucccga gagggugaga ccuucagaug acugggcuac ugacgaggac cuugugaaca    1620
ccauccaaau ucucaagcuc ccugcggccu uggacaggaa cggugcuugu guuggcgcca    1680
aauacgugcu uaagcuggaa ggcgagcauu ggacugucuc ugugacccuu gggauguccc    1740
cuucuuugcu cccccuugaa uguuucagg cuguuguga gcauaagagc ggacuugguc    1800
ccccagaugc ggucgaaguu uucggauuug acccugccug ccugaccga cuggcugagg    1860 uaaugcacuu gccagcagu gucaucccag cugcucuggc cgaaaugucc ggcgacccca    1920 accgucggc uuccccgguc acacugugu ggacuguuuc acaauucuuu gcccgccaca    1980
gaggaggaga gcaccugau caggugcgcu aaggaaaaau caucagcu ugucaaguug    2040 uugaggaaug cuguugccau cagaauaaaa ccaaccgggc caccccggaa gagguugcgg    2100
caaggauuga ucaguaccuc caugugcaa caagucuuga agaaugcuug auuaggcuug    2160 agagggnuuug cccgccgagc gcugcggaca ccuucuuuga uuggaauguu gugcucccug    2220
gggguugggc uucaacucag acaaccaaac agcuccaugu caaccagugc cgcgcucugg    2280
uuccugucgu gacucaagag ccuuuggaca aagacccagu cccucugacc gccuucucgc    2340
uguccaauug cuacuauccu gcacaaggug acgagguucg ucaccgugag aggcuaaaacu    2400 ccguacucuc uaagcuggag gggguuguuc gugaggaaua ugggcucacg ccaacuggac    2460
cuggcccgcg acccgcacua ccgaacgggc ucgucgaaacu uaaagaccag auggaggagg    2520 aucugcuaaaa acuagucaac gcccaggcaa cuucagaaau gauggccugg gcagccgagc    2580
agguugaucu gaaagcuugg gucaaaaacu cccacggug acaccguca ccccccucac    2640 caagaguuca gccucgaaaa acaaagccug ucaagagcuu gccagggaac aaaccugucc    2700
ccgcuccacg caggaagguc agaucugauu guggcagccc gauuucgaug ggcgacaaug    2760
uuccugacgg ucgggaagau uugacuguug guggcccccu ugaucuuucg acaccauccg    2820
agccgaugac accucugagu gagccugcac cuaugcccgc guugcaauau auuucuaggc    2880
cagugacacc uuugagugug cuggcccag uaccugcacc gcuagaacu gugcccgac    2940 cggugacgcc cuugagugag ccauuuuug ugucugcacc gcgacacaaa uuucagcagg    3000
uggaagaagc gaaucggcg gcaacaaugc ugacgcacca ggacgaaccu cuagauuugu    3060
cugcauccuc acagacugaa uaugaggcuu cuccccuaac accacugcag aacaugggua    3120
uucuggaggu gggggggcaa gaagcugagg aaguucugag ugaaaacucg gaucacacuga    3180 augacaucaa cccugcaccu gugucaucaa gcagcucccu gucaagUguu aagaucacac    3240
gcccaaaaca cucugcucaa gccaucauug acucgggcgg gcccgcagu gggcaucucc    3300 gaaagggaaa agaagcaugc cucagcauca ugcgugaggc uugugaugcg gcuaagcuua    3360
gugacccugc cacgcaggaa uggcuuucuc gcaugggga uagggguugau augcugacuu    3420 ggcgcaacac gucugcuuac caggcguucc gcaucuuaga ugguagguuu gaguuucccc    3480
caaagaugau acucgagaca ccgccgcccu acccgugugg guuugugaug cugccucgca    3540
cgccugcacc uuccgugggu gcagagagug accuuaccau ugguucaguc gccacugaag    3600
```

```
auguuccacg cauccucggg aaaauagaaa acgccggcaa gaugcccaac caggggcucu    3660
ugacauccuu cggggaagaa ccggugugcg accaaccugu caaggacucc uggaugucgu    3720
cgcggggguu ugacgagagc acaacggcuc cguccgcugg uacagguggu gcugacuuac    3780
ccaccgauuu gccaccuuca gauggeuugg augcggacga guggggccg uuacggacgg     3840 uaagaaagaa agcugaaagg cucuucgacc aauugagccg ucagguuuuu aaccucgucu    3900
cccaucsccc uguuucuuc ucacaccucu caaaucuga cagugguau ucuccgggug       3960 auuggggeuuu ugcagcuuuu acuuuauuuu gccucuuuu uguuacagc uacccauucu     4020 uugguuuugu uccccucuug ggugeuuuuu cugggucuuc ucggcgugug cgcaugggg     4080 uuuuggcug uggeuuggcu uugcuguug gccguucaa gccugugucc gacccagucg       4140
gcacugcuuu ugaguuugac ucgccagagu guaggaacgu ccuucauucu uugagcuuc     4200 ucaaaccuug ggacccuguu cgcagccuug uugugggccc cgucggcucuc ggccuugcca   4260 uucuuggcag guuacgggc ggggcacgcu acaucuggca uuuuugcuu aggcuuggca     4320 uuguugcaga uuguaucuug gcuggagcuu augugcuuuc caagguagg guaaaaagu     4380 gcuggggauc uuguguaaga acugucccua augaaaucgc cuucaacgug uccuuuua    4440 cgcgugcgac caggucguca cucaucgacc ugugcgaucg guuuugugcg ccaaaaggca   4500
uggaccccau uuccucgcu acuggguggc gcggugcug gaacggccga agucccauug   4560
agcaacccuc ugaaaacccc aucgcguucg cccaguugga ugaaaagagg aucacggcua 4620
gaacuguggu cgcucagccu uaugauccua accaagccgu aaagucuug cgggguguuac  4680 aggcggguggg ggcgauagug gccgaggcag ucccaaaagu gucaagguu uccgcuauuc  4740 cauuccgagc ucccuuuuuu cccaccggag ugaagguga uccugagugc aggaucgugg  4800
ucgaccccga cacuuuuacu acagcucucc ggucugguua uccaccaca aaccucgucc   4860 uugguguagg ggacuuugcc caacugaaug gauuaaaaau caggcaaauu uccaagcccu  4920 cggggaggagg cccgcaccuc auugcugccc ugcauguugc uugcucgaug gcguugcaca 4980
ugcuugcugg aguuuaugua acugcagugg ggucuugcgg uaccggcacc aacgauccgu  5040
ggugcacuaa cccauucgcc gucccuggcu acgaccuggg cucccucugc acguccagau  5100
ugugcaucuc ccaacauggc cuuacccugc ccuugacagc acuugggca ggauucgguc    5160 uucaggaaau ugccccuaguc guuuugauuu ucguuuccau cggaggcaug gcucauaggu 5220
ugaguuguaa ggcugauaug cugugcgucu acuugcaauu cgccagcuau guuugggauc 5280
cccuuaccug guugcucugu uguuuccuu gcuggeuugcg cugguucucu uugcaccuc    5340 ucaccauucu augguuggug uuuuucuuga ugucuguaaa uaugccuucg ggaaucuuaa   5400 ccguggugu auugguugcu cuuugcuuc uaggccguua acuaauguu guuggucuug     5460 uuaccccccua ugauauuucac cauuacacca augggccccg cggguguugcc gccuuggcua  5520 ccgcaccaga ugggacuuac uggccgcgcu ccgccgcgc ugcguugacu ggccgcaccg    5580
ugcuguuuac cccgucucag cuuggucccc uccuugaggg cgcuucaga acucgaaagc    5640 ccucacugaa caccgucaau guggucgggu ccccauggg cucuggcgga guguucacua   5700
ucgaugggaa aauuaagugc gugacugccg cacauguccu acgguaau ucagccaggg    5760 uuccggggu cggcuuuaau caaaugccuug acuugaugu aaaagggac uucgccauag    5820 cugacugccc gaauuggcaa ggggcugcuc cuaagaccca auucugcgag gaugauggga  5880
cuggccgcgc cuauuggcug acauccacug gcgucgaacc cggugucau gggaauggau   5940 ucgccuucug cuucaccgcg ucggcgauu ccggguccccc agugaucacc gaagccggug   6000
```

| | | | | |
|---|---|---|---|---|
| agcuugucgg | cguucacaca | ggaucaaaca | aacaaggagg | aggcauuguu | acgcgcccu | 6060 |
| cuggccaguu | uugcaaugug | gcacccauca | agcugagcga | auuaagugag | uucuuugcug | 6120 |
| gaccuaaggu | cccgcucggu | gaugugaagg | uuggcagcca | cauaauuaaa | gacauaugcg | 6180 |
| agguaccuuc | agaucuuugc | gccuugcuug | cugccaaacc | cgaacuggaa | ggaggccucu | 6240 |
| ccaccgucca | acuucugugu | guguuuuucc | uccugugag | aaugauggga | caugccugga | 6300 |
| cgcccuuggu | ugcuguuggg | uuuuuuaucu | ugaaugaggu | ucuccagcu | guacuggucc | 6360 |
| ggagguguuuu | cuccuuugga | auguuugugc | uaucuuggcu | cacaccaugg | ucugcgcaag | 6420 |
| uucugaugau | caggcuucua | acagcagcuc | uuaacaggaa | cagauuguca | cucgccuuuu | 6480 |
| acagccuugg | ugcagcgacc | gguuuugucg | cagaucuggc | ggcaacucaa | gggcacccgu | 6540 |
| ugcaggcagu | aaugaauuua | aguaccuaug | ccuuccugcc | ucggauaaug | ucgugaccu | 6600 |
| caccagucc | agugauugcg | ugguguguug | ugcaccuccu | ugccauaauu | uuguacuugu | 6660 |
| uuaaguaccg | cugccugcac | aaugccuug | uggcgaugg | ugcguucucu | gcggcuuucu | 6720 |
| ucuugcgaua | cuuugccgag | gggaaauuga | gggaagggu | gucgcaaucc | ugcgggauga | 6780 |
| aucaugaguc | gcugacuggu | gcccucgcua | ugagacuuaa | ugacgaggac | uuggauuuuc | 6840 |
| uuacgaaaug | gacugauuuu | aaguguuuug | uuucugcauc | caacaugagg | aaugcggcgg | 6900 |
| gccaguucau | cgaggcugcc | uaugcuaaag | cacuuagaau | ugaacuugcc | caguggugc | 6960 |
| agguugauaa | gguucgaggu | acuuggcca | aacuugaagc | uuuugcugau | accgguggcac | 7020 |
| cccaacucuc | gccggugac | auuguguug | cucuuggcca | uacgccuguu | ggcgguaucu | 7080 |
| ucgaccuaaa | gguuggguagc | accaagcaua | cccuccaagc | cauugagacc | agaguucuug | 7140 |
| ccgggguccaa | aaugaccgug | gcgcgugucg | uugauccaac | ccccacacccc | ccaccccgcac | 7200 |
| ccgugccuau | cccccuucca | ccgaaaaguuc | uggagaaugg | uccaacgcc | ugggggaug | 7260 |
| aggaucguuu | gaauaagaag | aagaggcgca | agauggaagc | cgucggcauc | uuuguuaugg | 7320 |
| guggaaagaa | auaucagaaa | uuuugggaca | agaacuccgg | ugauguguuu | auaggaggag | 7380 |
| uccaugauaa | cacagacgcg | ugggagugcc | ucagaguuga | caaccccugcc | gacuuugacc | 7440 |
| cugagaaggg | aacucugugc | gggcauacua | ccauugaaga | uaagacuuac | agugucuacg | 7500 |
| ccucccaccc | uggcaagaaa | uuccuggucc | ccgccuaccc | agagagcaaa | aaaaaccaau | 7560 |
| gggaagcugc | gaagcuuucc | guggaacagg | cccuuggcau | gaugaugcuc | gacggugaac | 7620 |
| ugacagccaa | agaaguggag | aaacugaaaa | gaauaauuga | caaacuccag | ggccugacua | 7680 |
| aggagcagug | uuuaaacgc | uagccgcgcag | cggcuugacc | cgcuggguc | gcggcggcuu | 7740 |
| gguuauuacu | gagacagcgg | uaaaaauagu | caaauuucac | aaccggaccu | ucacccuagg | 7800 |
| accugugaau | uuaaagugg | ccagagggu | ugagcuaaaa | gacgcggucg | agcauaacca | 7860 |
| acacccggu | gcaagaccgg | uugauggugg | uguugugcuc | cugcgcuccg | caguccuuc | 7920 |
| gcuuauagac | gucuuaaucu | ccggcgcuga | ugcaucccc | aaguuacucg | cccgccacgg | 7980 |
| gccgggaaac | acugggaucg | auggcacgcu | uugggauuuu | gaggccgagg | ccacuaaaga | 8040 |
| ggaaauugca | cucagugcgc | aaauaauaca | ggcuugugac | auuaggcgcg | gcgacgcacc | 8100 |
| ugaaauuggu | cuuccuuaua | agcuguaccc | ugucagggcc | aacccugagc | ggguaaaagg | 8160 |
| aguuuuacag | aauacaaggu | uuggagauau | accuuauaaa | acccccagug | acacuggaag | 8220 |
| cccagugcac | gcggcugccu | gccucacgcc | caaugccacu | ccggugacug | augggcgcuc | 8280 |
| cgucuuggcc | acgacuaugc | ccuccgguuu | ugaguuguau | guaccgacca | uuccagcguc | 8340 |
| ugccuugau | uaucuugauu | cuaggccuga | cugccccaaa | caguugacag | agcacggcug | 8400 |

```
ugaggacgcc gcauuaagag accucuccaa guaugacuug uccacccaag gcuuuguuuu    8460
accuggaguu cuucgccuug ugcguaagua ccuguuugcu caugugggua agugcccgcc    8520
cguucaucgg ccuuccacuu acccugccaa gaauucuaug gcuggaauaa augggaacag    8580
guuuccaacc aaggacaucc agagcguccc ugaaaucgac guucugugcg cacaggccgu    8640
ucgggaaaac uggcaaacug uuaccccuug uacccucaag aaacaguauu gugggaagaa    8700
gaagacuagg acaauacucg gcaccaauaa cuucauugcg cuggcucacc gggcagcguu    8760
gagugguguc acccagggcu ucaugaaaaa ggcguuuaac ucgcccauug cccucgguaa    8820
aaacaaauuu aaagagcuuc agacuccggu cuuaggcagg gccuugaag cugaucuugc     8880 auccugcgau cgcuccacac cugcaauugu ccgcugguuu gccgccaauc uucuuuauga    8940
acuugccugu gcugaagagc accagccguc guacguguu aacugcugcc acgaccuacu     9000
ggucacgcag uccggcgcag uaacuaagag aagguggccug ucgucuggcg acccgaucac   9060
uucugugucc aacaccauuu acagcuuggu gauauaugca caacacaugg ugcucaguua    9120
cuuuaaaagu ggucacccuc auggccuucu guuucuacaa gaccagcuga aguuugagga    9180
caugcucaag guucacccccc ugaucgucua uccggacgac cucguacugu augccgaguc   9240
ucccaccaug ccaaacuacc acugguggu ugaacaucug aaccugaugc ugggguuuuca    9300 gacggaccca aagaagacag ccauaacaga cucgccauca uuucuaggcu guaggauaau    9360
aaauggacgc cagcucgucc cuaaccguga caggauucuc gcggcccucg ccuaccauau    9420
gaaggcaagc aaugcucucug aauacuacgc cucggcggcu gcgauacuca uggacagcug   9480
ugcuuguuua gaguaugauc ccgaaugguu ugaagagcuu guaguuggga uagcgcagug    9540
ugcccgcaag gacggcuaca guuuccccgg cccgccguuc uucuugucca uguggaaaa    9600 acucagaucc aaucaugagg ggaagaaguc cagaaugugc gggcuacgcg ggcccccggc    9660
uccguacgcc acugccugug gcgucgacgu cuguauuuac cacacccacu uccaccagca    9720
uuguccaguc aucaucuggu guggccaccc ggcugguucu gguucuugua gugagugcaa    9780 accccccccua gggaaaggca aagcccucu agaugaggug uuagaacaag ucccguauaa    9840
gccuccacgg acuguaauca ugcauggga gcagggucuc accccucuug acccaggcag    9900
auaccagacu cgccgcggau uagcuccgu uaggcguggc auuagaggaa augagguuga    9960
ucuaccagac ggugauuaug cuagcaccgc ccuacucccu acuuguaaag agauuaacau   10020
ggucgcuguc gccucuaaug uguugcgcag cagguucauc aucggcccgc cugguugcugg 10080 gaaaacauac uggcucccuuc aacaggucca ggaggugau gccauuuaca cgccaacuca    10140
ccagaccaug cucgauauga uuagggcuuu ggggacgugc cgguucaacg ucccagcagg    10200
uacgacgcug caauucccug cccccucccg uaccggccu uggguucgca ccuagccgg     10260 cgguuggugu ccuggcaaga auuccuuccu ggaugaagca gcguauugua aucaccuuga    10320
ugucuugagg cuucuuagca aaacuacccu caccugucu ggagauuuca aacaaccuca    10380
cccagugggu uuugauucuc auugcuaugu uuuugacauc augccucaga cucaacugaa    10440
gaccaucugg agauuuggac agaauaucug ugaggccauu cagccagauu acagggacaa    10500
acuuguaucc auggucaaca caacccgugu aaccuacgug gaaaaccugu caaguaugg     10560 gcaagcccuc accccuuacc acagggaccg agaggacgg ccaucacaa uugacuccag      10620 ucaaggcgcc acauuugaug ugguuacacu gcauuugccc acuaaagauu cacucaacag    10680
gcaaagagcc cuuguugcua uuaccagggc aagacaugcu gucuugugu augcccaca      10740 caggcaacug cagagcaugu uugaucuucc ugcgaaaggc acacccgucu accucgcugu    10800
```

| | |
|---|---|
| gcaccgugac gagcagcuga ucgugcuaga uagaaauaac aaagaaugca cgguugcuca | 10860 |
| ggcucuaggc aauggggaua aauucagggc cacagacaag cgcguuguag auucucuccg | 10920 |
| cgccauuugu gcagaucugg aagggucgag cuccccgcuc cccaaggucg cacacaacuu | 10980 |
| gggauuuuau uucucgccug auuugacaca guuugcuaaa cucccgguag aacuugcacc | 11040 |
| ccacuggccc guggugacaa cccagaacaa ugaaagugg ccagaccggu ugguugcuag | 11100 |
| ccuucgcccc guccauaagu auagccgcgc gugcaucggu gccggcuaca ugguggggccc | 11160 |
| cucaguguuu cugggcaccc cuggggduugu gucauacuau cucacaaaau uguceagggg | 11220 |
| cgaggcucaa augcuuccgg agacagucuu cagcaccggc cgaauugagg uagauugccg | 11280 |
| ugaguaucuc gaugaccggg agcgagaaau ugcugagucc cuccccccaug cuucauugg | 11340 |
| cgacgucaaa ggcacuaccg uuggaggaug ucaccauguc accuccaaau accuccgcg | 11400 |
| cuuccuuccc aaggaaucag ucgcgguagu cggggguuuca agccccggga aagccgcaaa | 11460 |
| agcaguuugc acauuaacag augug uaucu cccagaucuc gaagcuuacc uccacccaga | 11520 |
| gacccagucc aagugcugga aaaugauguu ggacuucaag gaaguucgac ugauggucug | 11580 |
| gaaggacaag acggccuauu uucaacuuga aggccgccau uucaccuggu accagcuugc | 11640 |
| aagcuaugcc ucguacaucc gaguuccugu uaacucuacg guguauuugg accccugcau | 11700 |
| gggcccugcc cuuugcaaca aagagguugu cggguccacu cauuggggag cugaccucgc | 11760 |
| agucaccccu uaugauuacg gugccaaaau cauccugucu agugcauacc augugaaau | 11820 |
| gcccccuggg uacaaaaucc uggcgugcgc ggaguucucg cuugacgauc cagugaggua | 11880 |
| caaacacacc uggggguuug aaucggauac agcguaucug uacgaguuca ccggaaacgg | 11940 |
| ugaggacugg gaggauuaca augaugcguu ucgugcgcgc cagaaaggga aaauuuauaa | 12000 |
| ggccacugcc accagcauga gguuucauuu ucccccgggc ccugucauug aaccaacuuu | 12060 |
| aggccugaau ugaaaugaaa uggggguccau gcaaagccuc uuugacaaaa uuggccaacu | 12120 |
| uuucguggau gcuuucacgg aauuuuuggu guccauuguu gauaucauca uauuuuuggc | 12180 |
| cauuuuguuu ggcuuuacca ucgcuggcug gcuggugguc uucugcaucc gauugguuug | 12240 |
| cuccgcggua cuccgugcgc gcccuaccau ucacccugag caauuacaga agauccuaug | 12300 |
| aggccuuucu uucucagugc caggugggaua uucccaccug ggaacuaga cauccccugg | 12360 |
| ggaugcuuug gcaccauaag gugucaaccc ugauugauga aaugguguucg cgucggaugu | 12420 |
| accgcaccau ggaaaaagca ggacaggcug ccuggaaaca ggguggugagc gaggccacgc | 12480 |
| ugucucgcau uaguguuug gaugguggug ucauuuuuca gcaucuugcc gccauugaag | 12540 |
| ccgagaccug uaaauauuug gccucucggc ugcccaugcu acacaaucug cgcaugacag | 12600 |
| ggucaaaugu aaccauagug uauaauagua cuuugaauca ggugu uugcu auuuuuccaa | 12660 |
| ccccuggauc ccggccaaag cuucaugauu ucagcaaug gcuaauagcu gugcacuccu | 12720 |
| ccauauuuuc cuccguugcg gcuucuugua cucuuuugu ugcugug ugg uugcggauuc | 12780 |
| caaugcuacg uacuguuuuu gguuuccgcu gguuaggggc aauuuuuccu ucgaacucac | 12840 |
| ggugaauuac acggugugue cgccuugccu cacccgcaa gcagccgcug aggucuacga | 12900 |
| accaggcagg ucucuuuggu gcaggauagg gcaugaccga uguagugagg aagaccauga | 12960 |
| cgaucuaggg uucaugguuc cgucuggccu ccuagcgaa ggccacuuga ccaguguuua | 13020 |
| cgccugguug gcguuccugu ccuucagcua cacggcccag uuccaucccg agauauuugg | 13080 |
| gauagggaau gugagucaag uuuauguuga caucaagcac caauucaucu gcgccguuca | 13140 |
| cgacgggagg aacgccaccu ugccucguca ugacaauauu ucagccguau aucagaccua | 13200 |

```
cuaccaacau caagucgacg gcggcaauug guuucaccua gaauggcugc gccccuucuu    13260
uuccucuugg uugguuuuaa auguuucuug guuucucagg cguucgccug caagccaugu    13320
uucaguucaa gucuuucgga caucaaaacc aacacaaccg cagcaucagg cuuguuguc     13380 cuccaggaca ucagcugccu uaggcauggc gacucgugccu ucagacgau ucgcaaaagc    13440 ucucagugcc gcgcggcgau agggacgccc guguacauca cugucacagc caaugucaca    13500
gaugagaauu auuuacauuc uucgaucuc cuuaugcuuu cuucuugccu uuucuaugcu     13560
ucugagauga gugaaaaggg auucaaggug auguuuggca augugucagg caucguggcu    13620
guguguguca acuuuaccag cuacguccaa caugucaagg aguuuaccca acgcuccuug    13680
guggucgauc augugcggcu gcuccauuuc augacaccug agaccaugag gugggcaacc    13740 guuuagccu guuuucuugc caucuuacug gcaauugaa uguucaagua guuggggag      13800 augcuugacc gcgggcuguu gcucgcgauu gcuuucuuug ugguguaucg ugccauuuug   13860
uuuugcugcg cucgucaacg ccaacagcaa cagcagcucu caucuucagu uaauuuacaa    13920
cuugacgcua ugugagcuga auggcacaga uuggcugaaa gacaaauuug auugggcauu    13980
ggagacuuuu gucaucuuuc ccguguugac ucacauugac ucauauagug cacucaccac    14040
uagccauuuc cuugacacag ucggucuggu uacuguqucu acugccgggu cuaccacgg    14100 gcgguauguu cugaguagca ucuacgcggu cugcgcucug gccgcauuga cuugcuucgu    14160
cauuaggcuu gcgaagaacu gcaugccug gcgcuacucu uguaccagau auacuaacuu    14220
ccuucuggac acuaagggca gacucuaucg cuggcggucg cccguuauca uagagaaagg    14280
ggguaagguu gaggucgaag gucaccugau cgaccucaaa agaguugugc uugaugguuc    14340
cguggcaacc ccuuuaacca gaguuucagc ggaacaaugg ggucgucuuu agacgacuuu    14400
ugcuaugaua gcacggcucc acaaaaggug cuuuuggcgu uuuccauuac cuacgccca    14460 gugaugauau augcucuaaa gguaagucgc ggccgacuuu uagggcuucu gcaccuuuug    14520
aucuuucuga auuguacuuu uaccuucggg uacaugacau gcgugcacuu uaauagcaca    14580
aauaaggucg cgcucacuau gggagcagua guugcacuuc uuuggggggu guacucagcc    14640
auagaaaccu ggaaguucau caccuccaga ugucguuugu gcuugcuagg ccgcaaguac    14700
auucuggccc ccgcccacca cgucgaaagu gccgcgggcu ucauccgau cgcggcaaau    14760 gauaaccacg cauuugucgu ccggcgucc ggcuccacua cgguuaacgg cacauuggug    14820
cccggguuga aaagccucgu guugggugge agaaaagcug uuaaacaggg aguggguaaac   14880 cuugucaaau augccaaaua acaacggcaa gcagcaaaag aaaagagggg gaauggcca     14940 gccagucaau cagcugugcc agaugcuggg uaagaucauc gcccagcaaa accaguccag    15000 aggcaagggga ccggggaaga aaauuaagaa uaaaaacccg gagaagcccc auuuccucu    15060 agcgacugaa gaugacguca ggcaucacuu cacccccuagu gagcggcaau ugugucuguc   15120
gucgauccag acugccuuua accagggcgc uggaaccugu acccuaucag auucaggug     15180 gauaaguuac acgguggagu uuaguuugcc gacgcaucau acugugcgcc ugauccgcgu    15240
cacagcgcca ucaucagcgu aaugggcugg cauuccuuaa gcaccucagu guuagaauug    15300
gaagaaugug uggugaaugg cacugauggg cacugugccu cuaagucacc uauucaauua    15360
gggcgaccgu gggggguua aguuuaauug gcgagaacca ugcggccgaa auu           15413
```

<210> SEQ ID NO 4  
<211> LENGTH: 15413  
<212> TYPE: RNA  
<213> ORGANISM: Porcine reproductive and respiratory syndrome virus

```
<400> SEQUENCE: 4
augacguaua ggucuuggcu cuaugccuug gcauuuguau ugucaggagc ugcgaccauu      60
ggnacagccc aaaacuagcu gcacagaaaa cgcccuucug ugacagcccu cuucagggga     120
gcuuaggggu cugucccuag caccuugcuu ccggaguugc acugcuuuac ggucucucca     180
acccuuuaac caugucuggg auacuugauc ggugcacgug caccccccaau gccagggugu    240 uuauggcgga gggccaaguc uacugcacac gaugucucag gcacggucu cuccuuccuc      300 ugaaucucca aguccugag cuggagugc ugggccuauu uuacaggccc gaagagccac       360
uccgguggac guugccacgu gcauucccca cuguugagug cuccccgcc ggggccugcu      420 ggcuuucugc gaucuuucca auugcacgaa ugaccagugg aaaccugaac uuucaacaaa     480
gaauggugcg ggucgcagcu gagauuuaca gagccggcca gcucacccccu gcagucuuga    540 aggcucuaca aguuuaugaa cggggguugcc gcugguaccc uauagucgga ccuguccccug   600 gagugggccgu uuuugccaac ucccuacaug ugagugauaa accuuucccg ggagcaacuc    660
augugcuaac caaccugcca cucccgcaga ggccuaagcc ugaagacuuu gcccuuuug      720 agugugcuau ggcugacguc uaugauauug gucauggcgc cgucauguau uggccaaag     780 ggaaagucuc cugggccccu cguggcgggg augaggcgaa auuugaaacu gucccuaggg    840
aguugaaguu gaucgcgaac caacuccaca ucuccuuccc gccccaccac gcaguggaca   900
uguucaaguu uguguucaua gcccccuggga gugggugucuc uaugcggguc gagugcccac 960
acggcugucu ccccgcuaau acugucccug aagguaacug cuggguggcgc uuguuugacu  1020 cgcucccacu ggacguucag aacaaagaaa uucgccgugc caaccaauuc ggcuaucaaa   1080
ccaagcaugg ugucgcuggc aaguaccuac aacggaggcu gcaagcuaau ggucuccgag   1140
cagugacuga uacagaugga cccauugucg uacaguauuu cucuguuagg gagagcugga   1200
uccgccacuu cagacuggcg gaagagccua gccucccugg guuugaagac cuccucagaa   1260 uaagggguaga gcccaauacg ucgccauuga gugacaaggg uggaaaaauc uuccgguuug  1320
gcagucacaa augguacggu gcuggaaaga gagcaaggaa agcacgcucu gguaugacca  1380
ccacagucgc ucaccgcgcc uugcccgcuc ugaaauccca gcaagccaaa aagcacgagg  1440
augccggcgc ugauaaggcu gugcaucuca ggcacuauuc uccgccugcc gacgggaacu  1500
guguuuggca cugcauuucc gccaucgcca accgaauggu gaauuccaaa uuugaaacua  1560 cucuuucccga gagggugaga ccuucagaug acugggcuac ugacgaggac cuugugaaca  1620
ccauccaaau ucucaagcuc ccugcggccu uggacaggaa cggugcuugu guuggcgcca  1680
aauacgugcu uaagcuggaa ggcgagcauu ggacugucuc ugugacccuu gggaugucc   1740 cuucuuugcu cccccuugaa uguguucagg cuguuguga cauaagagc ggacuuggu     1800 ccccagaugc ggucgaaguu ucggauuug acccugccug ccuugaccga cuggcugagg   1860
uaaugcacuu gccuagcagu gucaucccag cugcucuggc cgaaauugcc ggcgacccca   1920
acuguccggc uuccccggu cuacugugu ggacuguuuc acaauucuuu gcccgccaca    1980
gaggaggaga gcaccccgau caggugcgcu uaggaaaaau caucagccuu gucaaguug   2040 uugaggaaug cuguugccau cagaauaaaa ccaaccgggc caccccggaa gagguugcgg  2100
caaggauuga ucaguaccuc cauggugcaa caagucuuga agaaugcuug auuaggcuug  2160 agagggguuug cccgccgagc gcugcggaca ccuucuuuga uuggaauguu gugcucccug  2220 gggugggggca uucaacucag acaaccaaac agccccaugu caaccagugc cgcgcucugg  2280
uuccugucgu gacucaagag ccuuuggaca aagacucagu cccucugacc gccuucucgc   2340
```

```
uguccaauug cuacuauccu gcacaaggug acgagguucg ucaccgugag aggcuaaacu    2400
ccguacucuc uaagcuggag ggggucuuc gugaggaaua ugggcucacg ccaacugaac    2460
cuggcccgcg acccgcacua ccgaacgggc ucgucgaacu aaagaccag auggaggagg    2520 aucugcugaa acuagucaac gcccaggcaa cuucagaaau gauggccugg gcagccgagc    2580
agguugaucu gaaagcuugg gucaaaaacu acccacggug gacaccgcca cccccuccac    2640
caagaguuca gccucgaaaa acaaagucug ucaagagcuu gccagggaac aaaccugucc    2700
ccgcuccacg caggaagguc agaucugauu guggcagccc gauuugaug ggcgacaaug    2760 uuccugacgg ucgggaagau uugacuguug guggccccu ugaucuuucg acaccauccg    2820
agccgaugac accucugagu gagccugcac uuaugcccgc guugcaauau auuucuaggc    2880
cagugacauc uuugagugug cuggcccccag uccugcacc gcuagaaacu gucccgac    2940 cggugacgcc cuugagugag ccaauuuuug ugucugcacc gcgacacaaa uuucagcagg    3000
uggaagaagc gaaucggcg gcaacaacgc ugacgcacca ggacgaaccu cuagauuugu    3060
cugcauccuc acagacugaa uaugaggcuu cucccccuaac accacugcag aacaugggua    3120
uucuggaggu ggggggcaa gaagcugagg aaguucugag ugaaaucucg gauacugaa    3180 augacaucaa cccugcaccu gugucaucaa gcagcucccu gucaagguu aagaucacac    3240 gcccaaaaca cucugcucaa gccaucauug acucgggcgg gcccugcagu gggcaucucc    3300
gaagggaaaa agaagcaugc cucagcauca ugcgugaggc uugugaugcg gcuaagcuua    3360
gugacccugc cacgcaggaa uggcuuucuc gcaugggga uagggucac augcugacuu    3420 ggcgcaacac gucugcuuac caggcguucc gcaucuuaga ugguagguu gaguuucucc    3480 caaagaugau acucgagaca ccgcgcccu acccgugugg guuugugaug cugccucaca    3540
cgccugcacc uuccgugggu gcagagagug accuuaccau ugguucaguc gccacugaag    3600 auguccacg cauucucggg aaaauagaaa acgccggcga gaugcccaac caggggcucu    3660
ugacauccuu cggggaagaa ccggugugcg accaaccugu caaggacucc uggaugucgu    3720 cgcgggguu ugacgagagc acaacggcuc cguccgcugg uacagguggu gcugacuuac    3780
ccaccgauuu gccaccuuca gaugguuugg augcggacga gugggggccg uuacggacgg    3840
uaagaaagaa agcugaaagg cucuucgacc aauugagccg ucagguuuuu aaccucgucu    3900
cccaucuccc uguuuucuuc ucacaccucu ucaaaucuga cagugguau ucuccgggug    3960 auuggggcuuu ugcagcuuuu acuuuauuuu gccucuuuuu guguuacagc uacccauucu    4020
uugguuuugu uccccucuug ggguguuuuu cugggcuuc ucggcgugug cgcauggggg    4080 uuuuggcug uuggcuggcu uuugcuguug gccuguucaa gccugugucc gacccagucg    4140
gcacugcuuu ugaguuugac ucgccagagu guaggaacgu ccuucauucu uuugagcuuc    4200
ucaaaccuug ggaccccuguu cgcagccuug uugugggccc cgucggucuc ggccuugcca    4260
uucuuggcag guuacugggc gggcacgcu acaucuggca uuuuuugcuu aggcuuggca    4320
uuguugcaga uuguaucuug gcuggagcuu augugcuuuc ucaagguagg guaaaaagu    4380 gcugggauc uuguguaaga acugcuccua augaaaucgc cuucaacgug uucccuuuua    4440
cgcgugcgac cagguccuca cucaucgacc ugugcgaucg guuugugcg ccaaaaggca    4500 uggaccccau uuuccucgcu acuggggcc gcgggugcug gaccggccga agucccauug    4560
agcaacccuc ugaaaaccc aucgcguucg cccaguugga ugaaagagg auuacggcua    4620 gaacuguggg cgcucagccu uaugauccua accaagccgu aaagugcuug cggugguuac    4680
aggcgggugg ggcgauagug gccgaggcag ucccaaaagu ggucaagguu ccgcuauuc    4740
```

| | | | | |
|---|---|---|---|---|
| cauuccgagc | ucccuuuuuu | cccaccgagu | gaagguuga | uccugagugc | aggaucgugg | 4800 |
| ucgaccccga | cacuuuuacu | acagcucucc | ggucugguua | cuccaccaca | aaccucgucc | 4860 |
| uuggguguggg | ggacuuugcc | caacugaaug | gauuaaaaau | caggcaaauu | uccaagcccu | 4920 |
| cgggaggagg | cccgcaccuc | auugcugccc | ugcauguugc | uugcucgaug | gcguugcaca | 4980 |
| ugcuugcugg | aguuuaugua | acugcagugg | ggucuugcgg | uaccggcacc | aacgauccgu | 5040 |
| ggugcacuaa | cccauucgcc | gucccuggcu | acggaccugg | ucccucugc | acguccagau | 5100 |
| ugugcaucuc | ccaacauggc | cuuacccugc | ccuugacagc | acuugggca | ggauucgguc | 5160 |
| uucaggaaau | ugcccuaguc | guuuugauuu | ucguuuccau | cggaggcaug | gcucauaggu | 5220 |
| ugaguuguaa | ggcugauaug | cugugcgucu | uacuugcaau | cgccagcuau | guuuggguac | 5280 |
| cccuuaccug | guugcucugu | uguuuccuu | gcugguugcg | cugguucucu | uugcacccuc | 5340 |
| ucaccauucu | augguuggug | uuuucuuga | ugucuguaaa | uaugccuucg | ggaaucuuaa | 5400 |
| ccgguguguu | auugguugcu | cuuugcuuc | uaggccguua | uacuaauguu | guuggucuug | 5460 |
| uuaccccua | ugauauucau | cauuacacca | auggcccccg | cggugüugcc | gccuuggcua | 5520 |
| ccgcaccaga | ugggacuuac | uuggccgcug | uccgccgcgc | ugcguugacu | ggccgcaccg | 5580 |
| ugcuguuuac | cccgucucag | cuugggucc | ucuugaggg | cgcuuucaga | acucgaaagc | 5640 |
| ccucacugaa | caccgucaau | ggguucgggu | ccccauggg | cucuggcgga | guguucacua | 5700 |
| ucgaugggaa | aauuaagugc | gugacugccg | cacauguccu | uacggguaau | ucagccaggg | 5760 |
| uuuccggggu | cggcuucaau | caaaugcuug | acuuugaugu | aaagggggac | uucgccauag | 5820 |
| cugauugccc | gaauuggcaa | ggggcugcuc | cuaagaccca | auucugcgag | gauggaugga | 5880 |
| cuggccgcgc | cuauuggcug | acauccucug | gcgucgaacc | cggugucauu | gggaauggau | 5940 |
| ucgccuucug | cuucaccgcg | ugcggcgauu | ccggguccc | agugaucacc | gaagccggug | 6000 |
| agcuugucgg | cguucacaca | ggaucaaaca | aacaaggagg | aggcauugu | uacgcgcccu | 6060 |
| cuggccaguu | uugcaauguug | gcacccauca | agcugagcga | auuaagugag | uucuugcug | 6120 |
| gaccuaaggu | cccgcucggu | gaugugaagg | uugcagcca | cauaauuaaa | gacauaugcg | 6180 |
| agguaccuuc | agaucuuugc | gccuugcuug | cugccaaacc | cgaacggaa | ggaggccucu | 6240 |
| ccaccgucca | acuucugugu | guguuuuucc | uccugggag | aaugauggga | caugccugga | 6300 |
| cgcccuuggu | ugcuguuggg | uuuuuuaucu | ugaaugaggu | ucucccagcu | guacugguce | 6360 |
| ggaguguuuu | cuccuuugga | auguuugugc | uaucuuggcu | cacaccaugg | ucugcgcaag | 6420 |
| uucugaugau | caggcuuucua | acagcagcuc | uuaacaggaa | cagauugca | cucgcccuuuu | 6480 |
| acagccuugg | ugcagcgacc | gguuuugucg | cagaucuggc | ggcaacucaa | gggcacccgu | 6540 |
| ugcaggcagu | aaugaauuua | aguaccuaug | ccuuccugcc | ucgauaaug | gucgugaccu | 6600 |
| caccaguccc | agugauugcg | ugggguguug | ugcaccuccu | ugccauaauu | uuguacuugu | 6660 |
| uuaaguaccg | cugccugcac | aaugccuug | uggcgaugg | ugcguucucu | gcggcuuucu | 6720 |
| ucuugcgaua | cuuugccgag | gggaaauuga | ggggaagggu | gucgcaaucc | ugcgggauga | 6780 |
| aucaugaguc | gcugacuggu | gcccucgcua | ugagacuuaa | ugacgaggac | uuggauuuuc | 6840 |
| uuacgaaaug | gacugauuuu | aaguguuuug | uucugcauc | caacaugagg | aaugcggcgg | 6900 |
| gccaguucau | cgaggcugcc | uaugcuaaag | cacuuagaau | ugaacuugcc | caguggugc | 6960 |
| agguugauaa | gguucgaggu | acuuuggcca | aacuugaagc | uuuugcugau | accgggcac | 7020 |
| cccaacucuc | gccccggugac | auuguguug | ucuuggcca | uacgccuguu | ggcguaucu | 7080 |
| ucgaccuaaa | gguugguagc | accaagcaua | cccuccaagc | cauugagacc | agaguucuug | 7140 |

-continued

| | | | | |
|---|---|---|---|---|
| ccggguccaa | aaugaccgug | gcgcgugucg | uugauccaac | ccccacaccc ccacccgcac | 7200 |
| ccgugccuau | cccccuucca | ccgaaaguuc | uggagaaugg | ucccaacgcc uggggggaug | 7260 |
| aggaucguuu | gaauaagaag | aagaggcgca | ggauggaagc | cgucggcauc uuuguuaugg | 7320 |
| guggaaagaa | auaucagaaa | uuugggaca | agaacuccgg | ugauguguuu uaugaggagg | 7380 |
| uccaugauaa | cacagacgcg | ugggagugcc | ucagaguuga | caacccugcc gacuuugacc | 7440 |
| cugagaaggg | aacucugugc | gggcauacua | ccauugaaga | uaagacuuac agugucuacg | 7500 |
| ccucccauc | uggcaagaaa | uuccggaucc | ccgucuaccc | agagagcaaa aaaaaccaau | 7560 |
| gggaagcugc | gaagcuuucc | guggaacagg | cccuuggcau | gaugaaugac gacgugaac | 7620 |
| ugacagccaa | agaaguggag | aaacugaaaa | gaauaauuga | caaacuccag ggccugacua | 7680 |
| aggagcagug | uuuaaacugc | uagccgccag | cggcuugacc | cgcuguggauc gcggcggcuu | 7740 |
| gguuguuacu | gagacagcgg | uaaaaauagu | caaauuucac | aaccggaccu ucacccuagg | 7800 |
| accugugaau | uuaaaagugg | ccagugaggu | ugagcuaaaa | gacgcggucg agcauaacca | 7860 |
| acacccgguu | gcaagaccgg | uugauggugg | uguugugcuc | cugcgcuccg caguccuuc | 7920 |
| gcuuauagac | gucuuaaucu | ccggcgcuga | ugcaucuccc | aaguuacucg cccgccacgg | 7980 |
| gccgggaaac | acugggaucg | auggcacgcu | uugggauuuu | gaggccgagg ccacuaaaga | 8040 |
| ggaaauugca | cucagugcgc | aaauaauaca | ggcuugugac | auuaggcgcg gcgacgcacc | 8100 |
| ugaaauuggu | cuuccuuaua | agcuguaccc | ugucaggggc | aacccugagc ggguaaaagg | 8160 |
| aguuuuacag | aauacaaggu | uuggagacau | accuuauaaa | accccagug acacuggaag | 8220 |
| cccagugcac | gcggcugccu | gccucacgcc | caaugccacu | ccggugacug augggcgcuc | 8280 |
| cgucuuggcc | acgacuaugc | ccuccgguuu | ugaguuguau | guaccgacca uuccagcguc | 8340 |
| ugccuugau | uaucuugauu | cuaggccuga | cugccccaaa | caguugacag agcacggcug | 8400 |
| ugaggacgcc | gcauuaagag | accucuccaa | guaugacuug | uccacccaag gcuuuguuu | 8460 |
| accuggaguu | cuucgccuug | ugcguaagua | ccguuugcu | caugugggua agugcccgcc | 8520 |
| cguucaucgg | ccuuccacuu | acccugccaa | gaauucuaug | gcuggaauaa augggaacag | 8580 |
| guuuccaacc | aaggacaucc | agagcguccc | ugaaaucgac | guucugugcg cacaggccgu | 8640 |
| gcgggaaaac | uggcaaacug | uuacccccuug | uacccucaag | aaacaguauu gugggaagaa | 8700 |
| gaagacuagg | acaauacucg | gcaccaauaa | cuucauugcg | cuggcccacc gggcagcguu | 8760 |
| gagugguguc | acccagggcu | ucaugaaaaa | ggcguuuaac | ucgcccauug cccucgguaa | 8820 |
| aaacaaauuu | aaagagcuuc | agacuccggu | cuuaggcagg | ugccuugaag cugaucuugc | 8880 |
| auccugcgau | cgcuccacac | cugcaauugu | ccgcuggutu | gccgccaauc uucuuauga | 8940 |
| acuugccugu | gcugaagagc | accugccguc | guacgcguug | aacugcugcc acgaccuacu | 9000 |
| ggucacgcag | uccggcgcag | uaacuaagag | agguggccug | ucgucuggcg acccgaucac | 9060 |
| uucugugucc | aacaccauuu | acagcuuggu | gauauaugca | caaacauggu ugcucaguua | 9120 |
| cuuuaaaagu | ggucacccuc | auggccuucu | guuucuacaa | gaccagcuga aguuugagga | 9180 |
| caugcucaag | guucaacccc | ugaucgcuua | uucggacgac | cucguacugu augccgaguc | 9240 |
| ucccaccaug | ccaaacuacc | acugguggu | ugaacaucug | aaccgaugc uggguuuuca | 9300 |
| gacgacccca | aagaagacag | ccauaacaga | cucgccauca | uuucuaggcu guaggauaau | 9360 |
| aaauggacgc | cagcucgucc | cuaaccguga | caggauucuc | gcggcccucg ccuaccauau | 9420 |
| gaaggcaagc | aaugucucug | aaucuacgcg | cucggcggcu | gcgauacuca uggacagcug | 9480 |
| ugcuuguuua | gaguaugauc | ccgaaugguu | ugaagagcuu | guaguuggga uagcgcagug | 9540 |

| | |
|---|---|
| ugcccgcaag gacggcuaca guuuucccgg cccgccguuc uucuugucca uguggaaaa | 9600 |
| acucagaucc aaucaugagg ggaagaaguc cagaaugugc ggguacugcg gggcccggc | 9660 |
| uccguacgcc acugccugug gccucgacgu cuguauuuac cacacccacu uccaccagca | 9720 |
| uuguccaguc aucaucuggu guggccaccc ggcugguucu gguucuugua gugagugcaa | 9780 |
| acccccccua gggaaaggca caagcccucu agaugaggug uuagaacaag ucccguauaa | 9840 |
| gccuccacgg acuguaauca ugcaugugga gcagggucuc accccucuug acccaggcag | 9900 |
| auaccagacu cgccgcggau uagucuccgu uaggcguggc auuagaggaa ugagguuga | 9960 |
| ucuaccagac ggugauuaug cuagcaccgc ccuacucccu acuuguaaag agauuaacau | 10020 |
| ggucgcuguc gccucuaaug uguugcgcag cagguucauc aucggcccgc cuggugcugg | 10080 |
| gaaaacauac uggcuccuuc aacaggucca ggauggugau gucauuuaca cgccaacuca | 10140 |
| ccagaccaug cucgauauga uuagggcuuu ggggacgugc cgguucaacg ucccagcagg | 10200 |
| uacgacgcug caauucccug cccccucccg uaccggcccu ugggucgca uccuagccgg | 10260 |
| cgguuggugu ccuggcaaga auuccuuccu ggaugaagca gcguauugua aucaccuuga | 10320 |
| ugucuugagg cuucuuagca aaacuacccu caccugucug ggagauuuca aacaauccca | 10380 |
| cccagugggu uuugauucuc auugcuaugu uuuugacauc augccucaga cucaacugaa | 10440 |
| gaccaucugg agauuuggac agaauaucug ugaugccauu cagccagauu acagggacaa | 10500 |
| acuuguaucc auggucaaca caacccgugu aaccuacgug gaaaaaccug ucaaguaugg | 10560 |
| gcaaguccuc accccuuacc acagggaccg agaggacggc gccaucacaa uugacuccag | 10620 |
| ucaaggcgcc acauugaug ugguuacacu gcauugccc acuaaagauu cacucaacag | 10680 |
| gcaaagagcc cuuguugcua uuaccagggc aagacaugcu aucuugugu augacccaca | 10740 |
| caggcaacug cagagcaugu uugaucuucc ugcgaaaggc acacccguca accucgcugu | 10800 |
| gcaccgugac gagcagcuga ucugcuaga uagaaauaac aaagaaugca cgguugcuca | 10860 |
| ggcucuaggc aauggggaua aauucagggc cacagacaag cgcguuguag auucucuccg | 10920 |
| cgccauuugu gcagaucugg aagggucgag cuccccgcuc cccaaggucg cacacaaucuu | 10980 |
| gggauuuuau uucucgccug auuugacaca guuugcuaaa cucccgguag aacuugcacc | 11040 |
| ccacuggccc guggugacaa cccagaacaa ugaaaagugg ccagaccggu ugguugcuag | 11100 |
| ccuucgcccc guccauaagu auagccgcgc gugcaucggu gccggcuaca ggugugggccc | 11160 |
| cucaguguuu cugggcaccc cuggggguugu gucauacuau cucacaaaau ugucagggg | 11220 |
| cgaggcucaa augcuuccgg agacagucuu cagcaccggc cgaauugagg uagauugccgc | 11280 |
| ugaguaucuu gaugaccggg agcgagaaau ugcugaguccc cuccccaug cuuucauugg | 11340 |
| cgacgucaaa ggcacuaccg uuggaggaug ucaccaugucc accucaaau accuuccgcg | 11400 |
| cuuccuuccc aaggaaucag ucgcgguagu cggggguuuca gcccggga aagccgcaaa | 11460 |
| agcaguuugc acauuaacag auguguaucu cccagaucuc gaagcuuacc uccacccaga | 11520 |
| gacccaugucc aagugcugga aaaugauguu ggacuucaag gaaguucgac ugauggucug | 11580 |
| gaaggacaag acggcuauuu ucaacauuga aggccgccau ucaccuggu accagcuugc | 11640 |
| aagcuaugcc ucguacaucc gaguccugu uaacucuacg guguauuugg accccugcau | 11700 |
| gggcccugcc cuuugcaaca gaagaguugu cgggucacu cauuggggag cugaccucgc | 11760 |
| agucacccu uaugauuacg gugccaaaau caucccugucu agugcauacc auggugaaau | 11820 |
| gccccuggu uacaaaauccc uggcgugcgc ggaguucucg cuugacgauc cagugaggua | 11880 |
| caaacacacc uggggguuug aaucggauac agcguaucug uacgaguuca ccggaaacgg | 11940 |

```
ugaggacugg gaggauuaca augaugcguu ucgugcgcgc cagaaaggga aaauuuauaa   12000
ggccacugcc accagcauga gguuucauuu uccccgggc ccugucauug aaccaacuuu    12060
aggccugaau ugaaaugaaa uggggaccau gcaaagccuc uuugacaaaa uuggccaacu   12120
uuuuguggau gcuuucacgg aauuuuuggu guccauuguu gauaucauca uauuuuuggc   12180
cauuuuguuu ggcuuuacca ucgcuggcug gcuggugguc uucugcaucc gauugguuug   12240
cuccgcggua uccgugcgc gcccuaccau ucaccugag caauuacaga gauccuaug     12300 aggccuuucu uucucagugc cagguggaua uucccaccug gggaacuaga cauccccugg   12360
ggauguuuug gcaccauaag gugucaaccc ugauugauga aauggugucg cgucggaugu   12420
accgcaccau ggaaaaagca ggacaggcug ccuggaaaca gguggugagc gaggccacgc   12480
ugucucgcau uagugguuug gaugguggug ucauuuuuca gcaucuugcc gccauugaag   12540
ccgagaccug uaaauauuug gccucucggc ugcccaugcu acacaaucug cgcaugacag   12600
ggucaaaugu aaccauagug uauaauagua cuuugaauca ggguguugcu auuuuuccaa   12660
ccccuggauc ccggccaaag cuucaugauu ucagcaaug gcuaauagcu gugcacuccu    12720
ccauauuuuc uccguugcg gcuucuugua ucuuuuugu ugugcugugg uugcggauuc     12780
caauacuacg uacuguuuuu gguuuccgcu gguuaggggc aauuuuuccu ucgaacucac   12840
ggugaauuac acggugucuc cgccuugccu caccccggcaa gcagccgcug aggucuacga  12900
accaggcagg ucucuuuggu gcaggauagg gcaugaccga uguagugagg acgaccauga   12960
cgaucuaggg uucaugguuc cgccuggccu uccagcgaa ggccacuuga ccaguguuua   13020
cgccugguug gcguuccugu ccuucagcua cacggcccag uuccaucccg agauauuugg   13080
gauagggaau gugagucaag uuuauguuga caucaagcac caauucaucu cgccguuca    13140 cgacggggag aacgccaccu ugccucguca ugacaauauu ucagccguau uucagaccua   13200
cuaccaacau caagucgacg gcggcaauug guuucaccua gaauggcugc gcccuucu    13260 uuccucuugg uugguuuuaa auguuucuug guuucucagg cguucccug caagccaugu    13320 uucaguucaa gucuuucgga caucaaaacc aacacuaccg cagcaucagg cuuuguugu    13380 cuccaggaca ucagcugccu uaggcauggc gacucguccu cucagacgau ucgcaaaagc   13440
ucucagugcc gcgcggcgau agggacgccc guguacauca cugucacagc caaugucaca   13500
gaugagaauu auuuacauuc uucgauccuc cuuaugcuuu cuucuugccu uucuaugcu    13560 ucugagauga gugaaaaggg auucaaggug auauuuggca augugucagg caucguggcu   13620 gugugugca acuuuaccag cuacguccaa caugucaagg aguuacccca acgcuccuug    13680
guggucgauc augugcggcu gcuccauuuc augacaccug agaccaugag gugggcaacc   13740 guuuagccu guuuuuugc caucuuacug gcaauugaa uguucaagua guugggag       13800 augcuugacc gcgggcuguu gcucgcgauu gcuuucuuug ugguguaucg ugccauuuug   13860 uuugcugcg cucgucaacg ccaacagcaa cagcagcucu caucuucagu ugauuuacaa   13920
cuugacgcua ugugagcuga auggcacaga uuggcugaaa gacaaauuug auugggcagu   13980
ggagacuuuu gucaucuuuc ccguguugac ucacauuguc ucauaugug cacucaccac   14040 uagccauuuc cuugacacag ucggucuggu uacuguguc accgccgggu cuaccacgg    14100 gcgguauguu cugagucagca cuacgcgguu cugcgcucug gccgcauuga uuugcuucgu   14160 cauuaggccuu gcgaagaacu gcaugcccug gcgcuacucu uguaccagau auacuaacuu  14220
ccuucuggac acuaagggca gacucuaucg cuggcggucg cccguuauca uagagaaagg   14280
ggguaagguu gaggucgaag gucaccugau cgaccucaaa agaguugugc uugaugguuc   14340
```

-continued

```
cguggcaacc ccuuuaacca gaguuucagc ggaacaaugg ggucgucuuu agacgacuuu    14400
ugcuaugaua gcacggcucc acaaaaggug cuuuuggcgu uuuccauuac cuacacgcca    14460
gugaugauau augcucuaaa gguaagucgc ggccgacuuu uagggcuucu gcaccuuuug    14520
aucuuucuga auuguacuuu uaccuucggg uacaugacau ucgugcacuu uaauagcaca    14580
aauaaggucg cgcucacuau gggagcagua guugcacuuc uuuggggggu guacucagcc    14640
auagaaaccu ggaaguucau caccuccaga ugccguuugu gcuugcuagg ccgcaaguac    14700
auucuggccc ccgcccacca cgucgaaagu gccgcgggcu uucauccgau cgcggcaaau    14760
gauaaccacg cauuugucgu ccggcguccc ggcuccacua cgguuaacgg cacauuggug    14820
cccggguuga aaagccucgu guuggguggc agaaaagcug uuaaacaggg aguguaaac     14880 cuugucaaau augccaaaua acaacggcaa gcagcaaaag aaaaagaggg ggaauggcca    14940
gccagucaau cagcugugcc agaugcuggg uaagaucauc gcccagcaaa accaguccag    15000
aggcaaggga ccggggaaga aaauuaagaa uaaaaacccg gagaagcccc auuuuccucu    15060
agcgacugaa gaugacguca ggcaucacuu cacccuagu gagcggcaau uguguccuguc    15120 gucgauccag acugccuuua accagggcgc uggaaccugu acccuaucag auucagguag    15180
gauaaguuac acuguggagu uuaguuugcc gacgcaucau acugugcgcc ugauccgcgu    15240
cacagcgcca ucaucagcgu aaugggcugg cauuccuuaa gcaccucagu guuagaauug    15300
gaagaaugug uggugaaugg cacugauugg cacugugccu cuaagucacc uauucaauua    15360
gggcgaccgu gugggguua aguuuaauug gcgagaacca ugcggccgaa auu            15413
```

<210> SEQ ID NO 5
<211> LENGTH: 21
<212> TYPE: DNA
<213> ORGANISM: Artificial Sequence
<220> FEATURE:
<223> OTHER INFORMATION: Artificial Primer

<400> SEQUENCE: 5
cgccctaatt gaataggtga c                                              21

<210> SEQ ID NO 6
<211> LENGTH: 38
<212> TYPE: DNA
<213> ORGANISM: Artificial Sequence
<220> FEATURE:
<223> OTHER INFORMATION: Artificial Primer

<400> SEQUENCE: 6
ccttcggcag gcggggagta gtgtttgagg tgctcagc                             38